United States Patent
Kobayashi

(10) Patent No.: US 12,016,722 B2
(45) Date of Patent: Jun. 25, 2024

(54) MEDICAL INFORMATION PROCESSING SYSTEM AND MEDICAL INFORMATION PROCESSING METHOD

(71) Applicant: Canon Medical Systems Corporation, Otawara (JP)

(72) Inventor: Yoshimasa Kobayashi, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 24 days.

(21) Appl. No.: 17/078,301

(22) Filed: Oct. 23, 2020

(65) Prior Publication Data

US 2021/0052247 A1    Feb. 25, 2021

Related U.S. Application Data

(63) Continuation of application No. PCT/JP2019/018051, filed on Apr. 26, 2019.

(30) Foreign Application Priority Data

| Apr. 27, 2018 | (JP) | 2018-086998 |
| Apr. 25, 2019 | (JP) | 2019-084733 |

(51) Int. Cl.
*A61B 8/08* (2006.01)
*A61B 5/00* (2006.01)
(Continued)

(52) U.S. Cl.
CPC ............ *A61B 8/0825* (2013.01); *A61B 5/004* (2013.01); *A61B 5/055* (2013.01); *A61B 6/032* (2013.01);
(Continued)

(58) Field of Classification Search
CPC ....... A61B 5/055; A61B 6/032; A61B 8/0825; A61B 6/502; A61B 5/4312; A61B 8/5261; G16H 50/20
See application file for complete search history.

(56) References Cited

U.S. PATENT DOCUMENTS

| 2002/0097902 A1* | 7/2002 | Roehrig ............... G06T 7/0012 382/132 |
| 2015/0178925 A1* | 6/2015 | Jo ........................ A61B 6/5247 382/131 |

(Continued)

FOREIGN PATENT DOCUMENTS

| JP | 2003-000575 A | 1/2003 |
| JP | 2004-097830 A | 4/2004 |

(Continued)

OTHER PUBLICATIONS

International Search Report dated Jul. 16, 2019 in PCT/JP2019/018051 filed on Apr. 26, 2019, 1 page.

*Primary Examiner* — Patrick Fernandes
*Assistant Examiner* — Nicholas A Robinson
(74) *Attorney, Agent, or Firm* — Oblon, McClelland, Maier & Neustadt, L.L.P.

(57) ABSTRACT

According to one embodiment, a medical information processing system includes processing circuitry. The processing circuitry acquires an ultrasound image of a subject. The processing circuitry acquires a first modality image of the subject, the first modality image differing from the ultrasound image. The processing circuitry acquires an imaging position for the ultrasound image. The processing circuitry generates diagnosis support information for the subject based on the ultrasound image, the imaging position for the ultrasound image, and the first modality image.

4 Claims, 46 Drawing Sheets

(51) Int. Cl.
  *A61B 5/055*    (2006.01)
  *A61B 6/03*     (2006.01)
  *A61B 6/50*     (2024.01)
(52) U.S. Cl.
  CPC .............. *A61B 6/037* (2013.01); *A61B 6/502* (2013.01); *A61B 8/5261* (2013.01)

(56) References Cited

U.S. PATENT DOCUMENTS

2017/0024903 A1   1/2017   Razzaque
2019/0035094 A1   1/2019   Ishikawa et al.

FOREIGN PATENT DOCUMENTS

JP      2015-173899 A       10/2015
JP      2017-136354 A        8/2017
WO      WO-0243801 A2 *      6/2002   ............. A61B 6/463

* cited by examiner

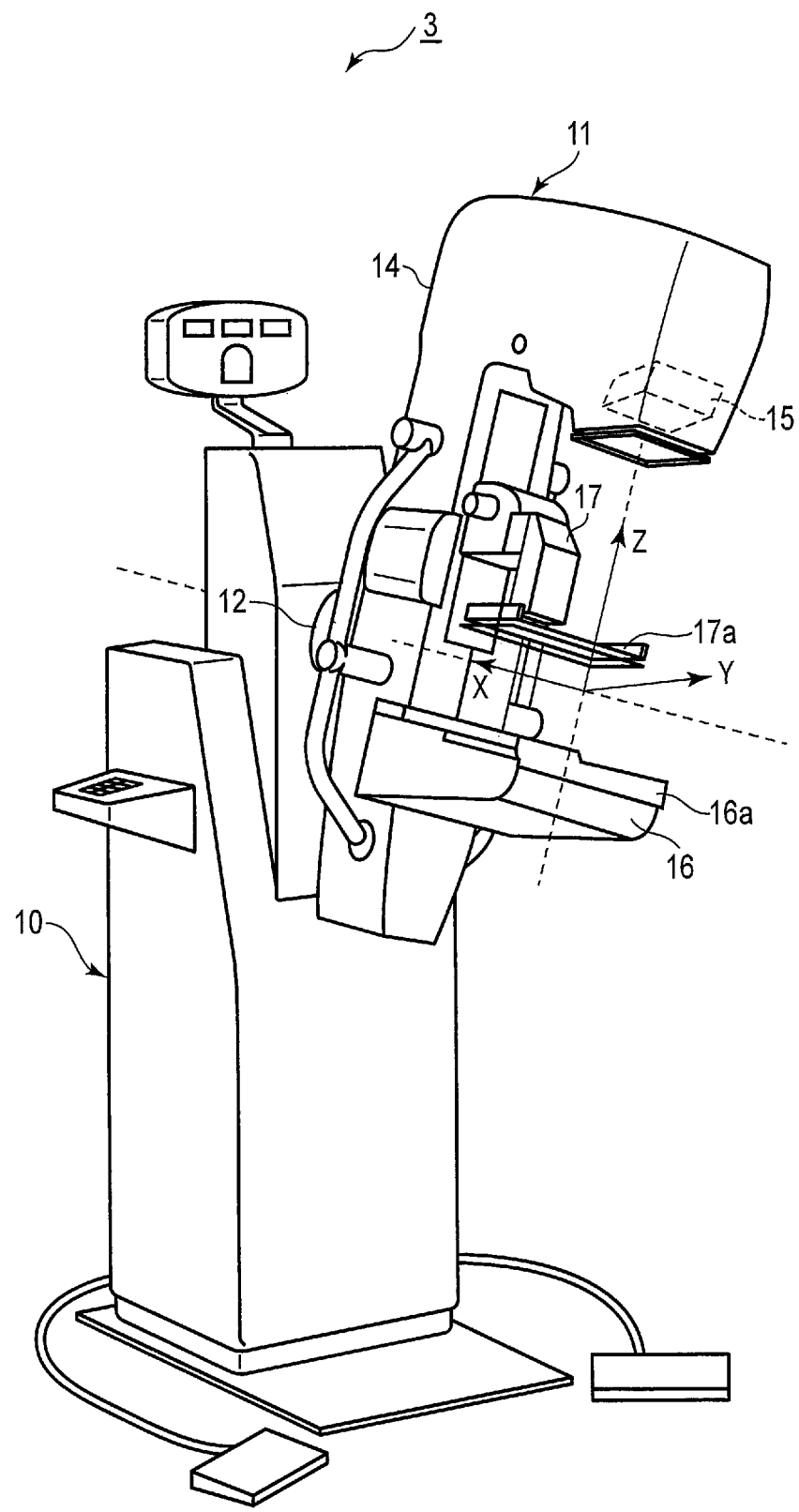
F I G. 3

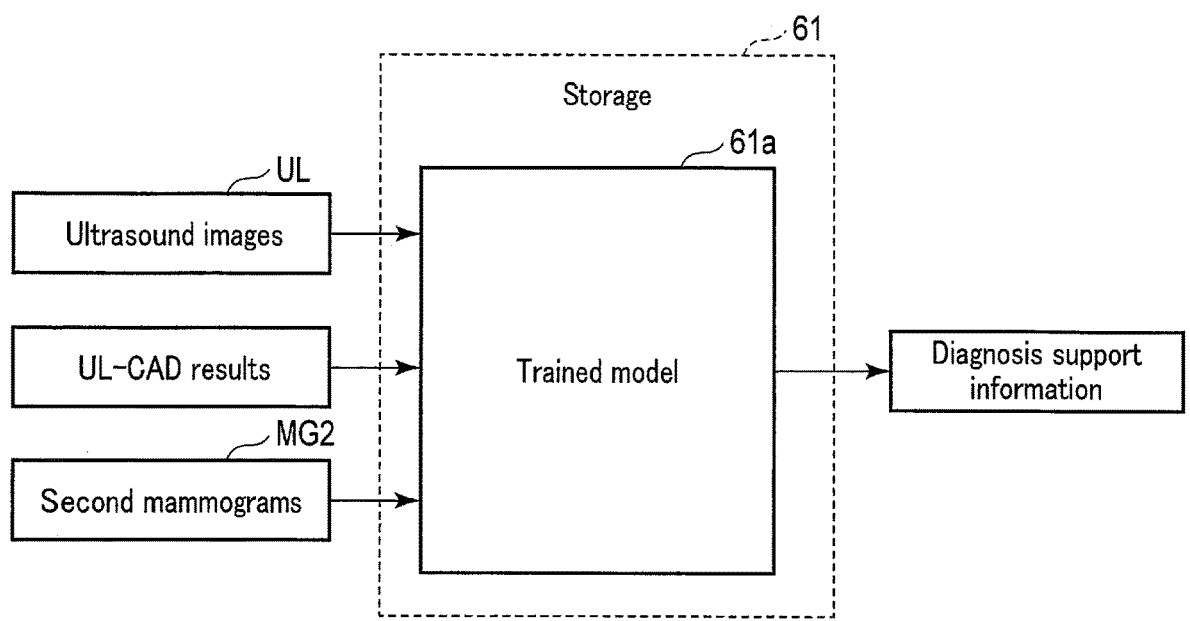
F I G. 10

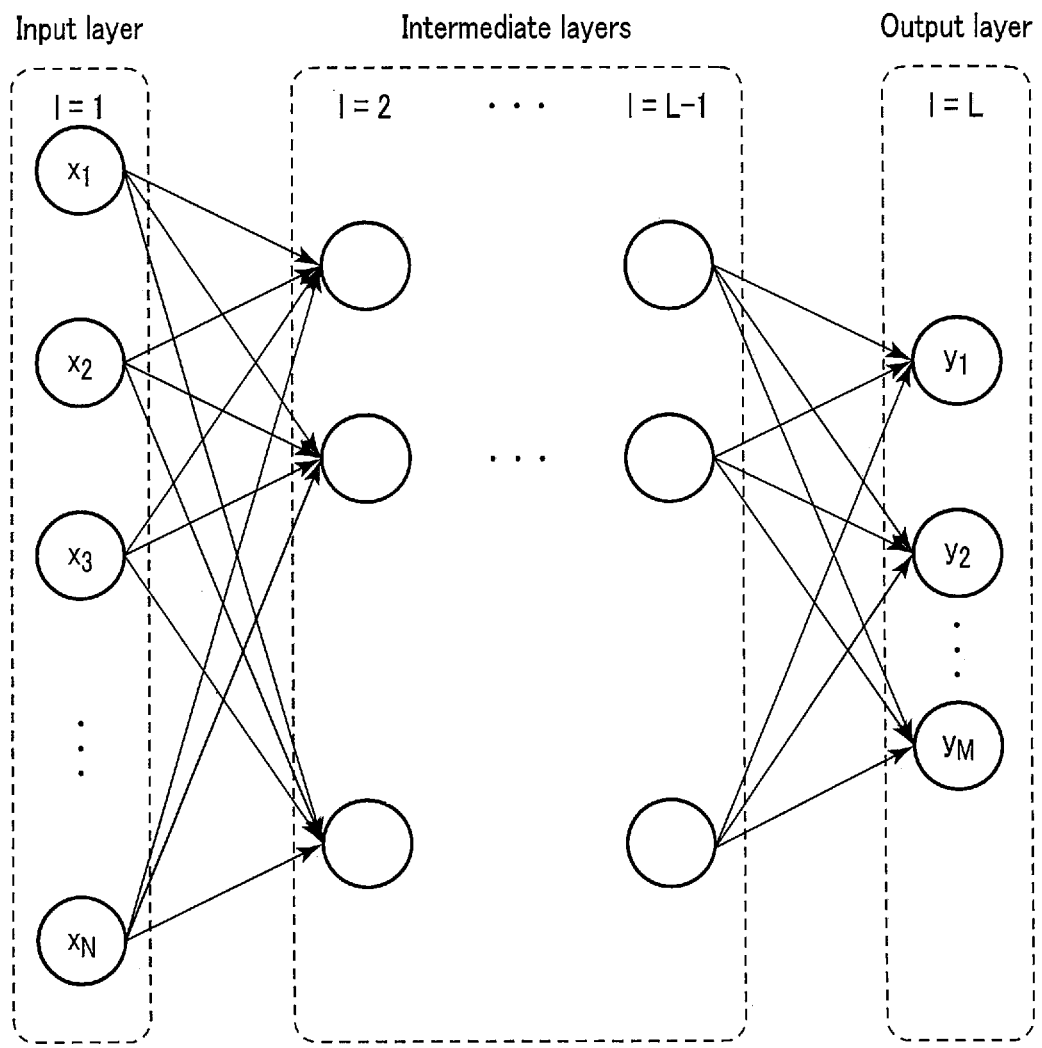
F I G. 11

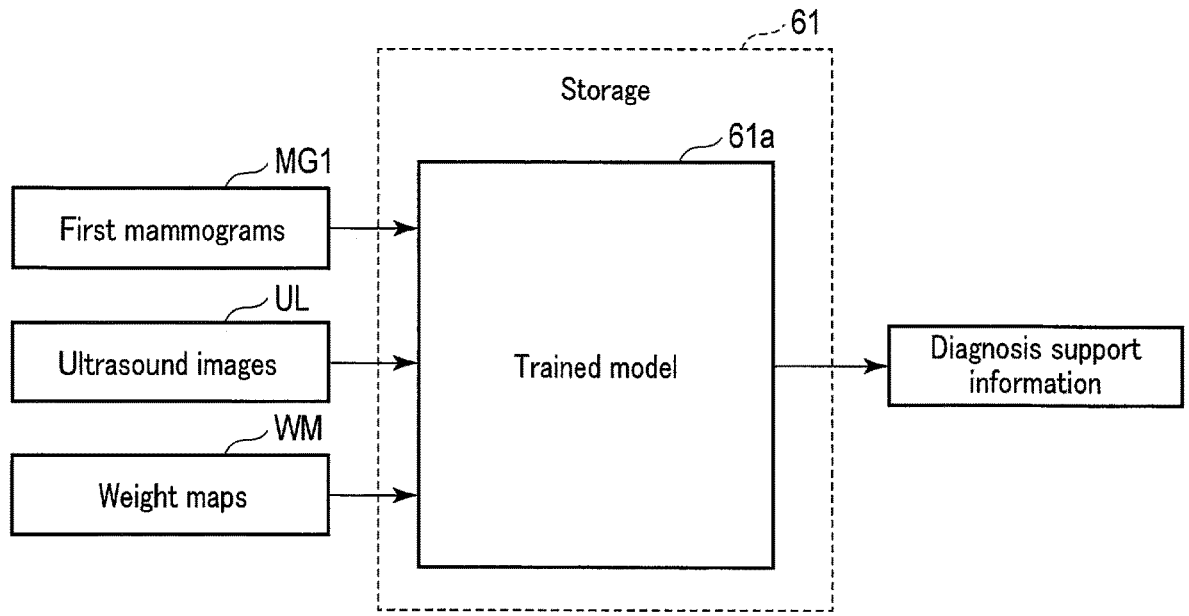
F I G. 14
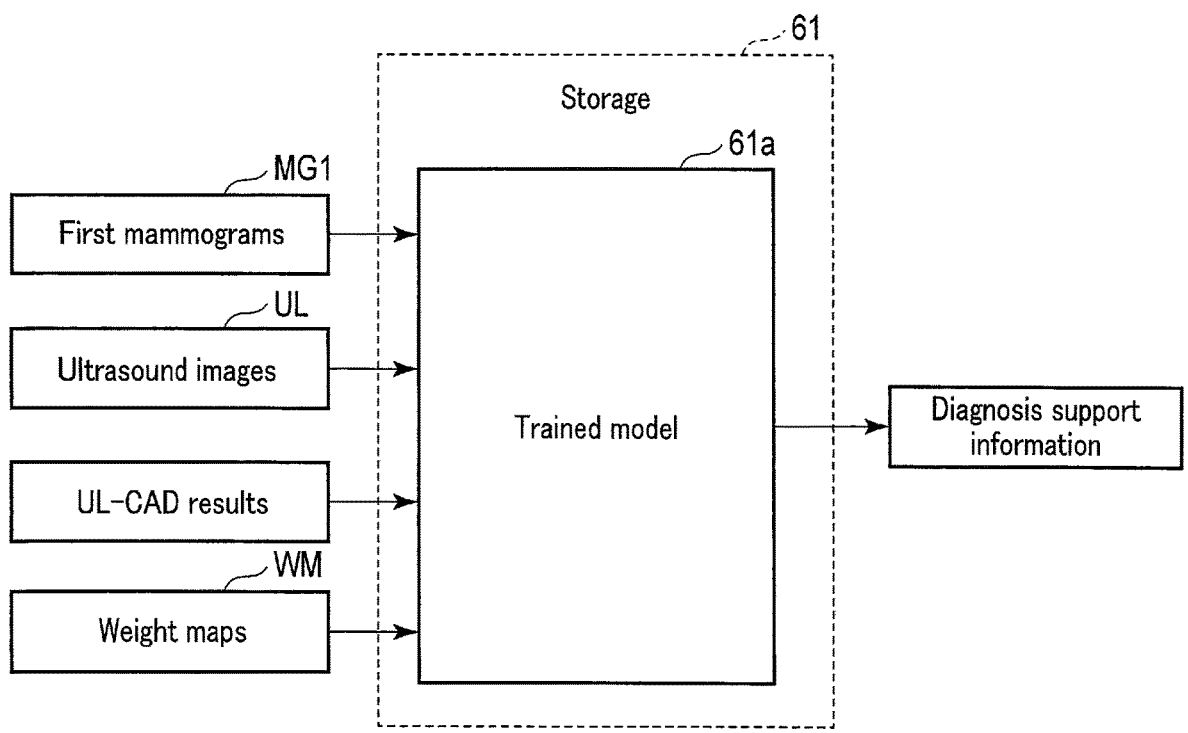
F I G. 15

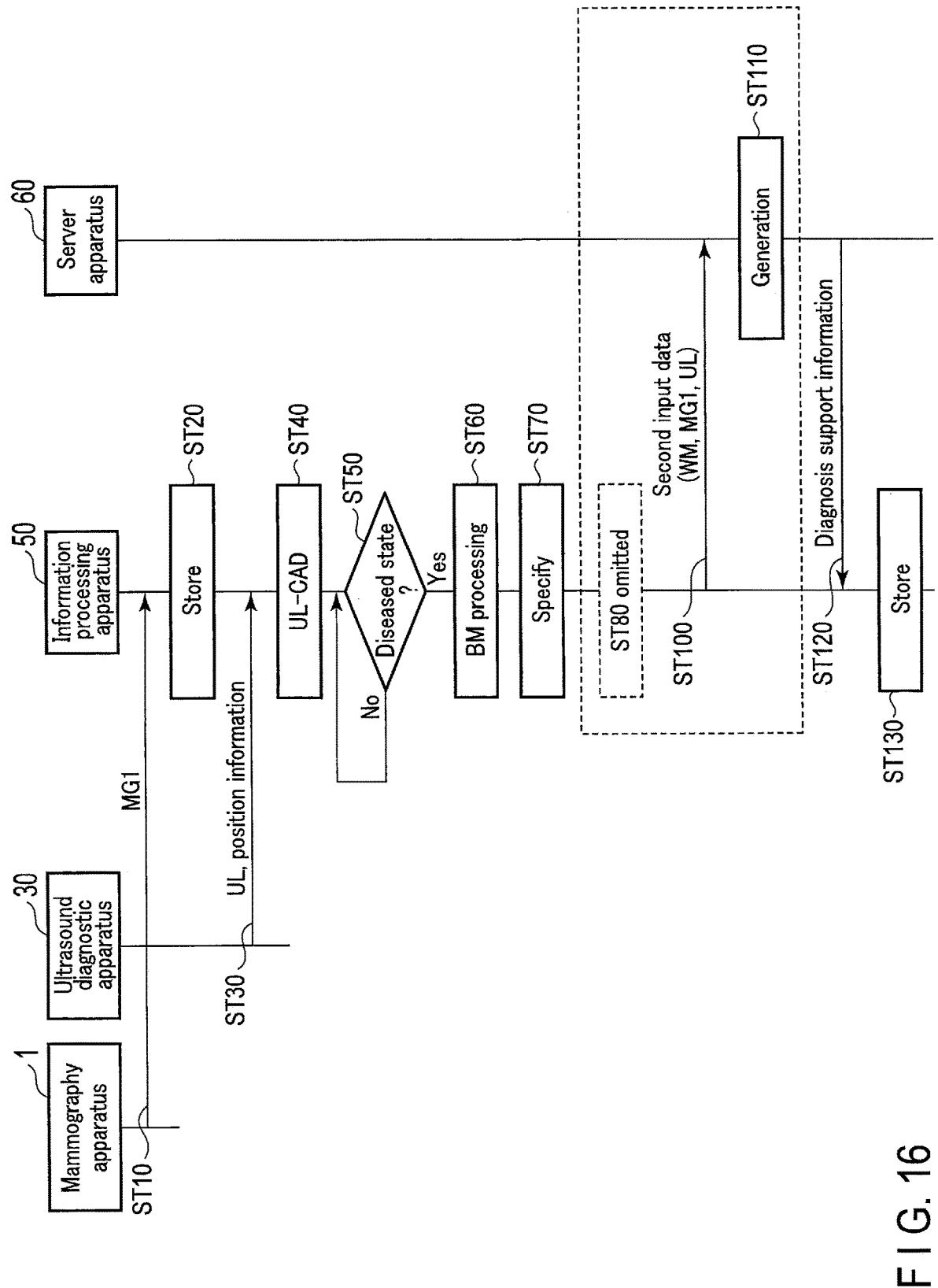
F I G. 16

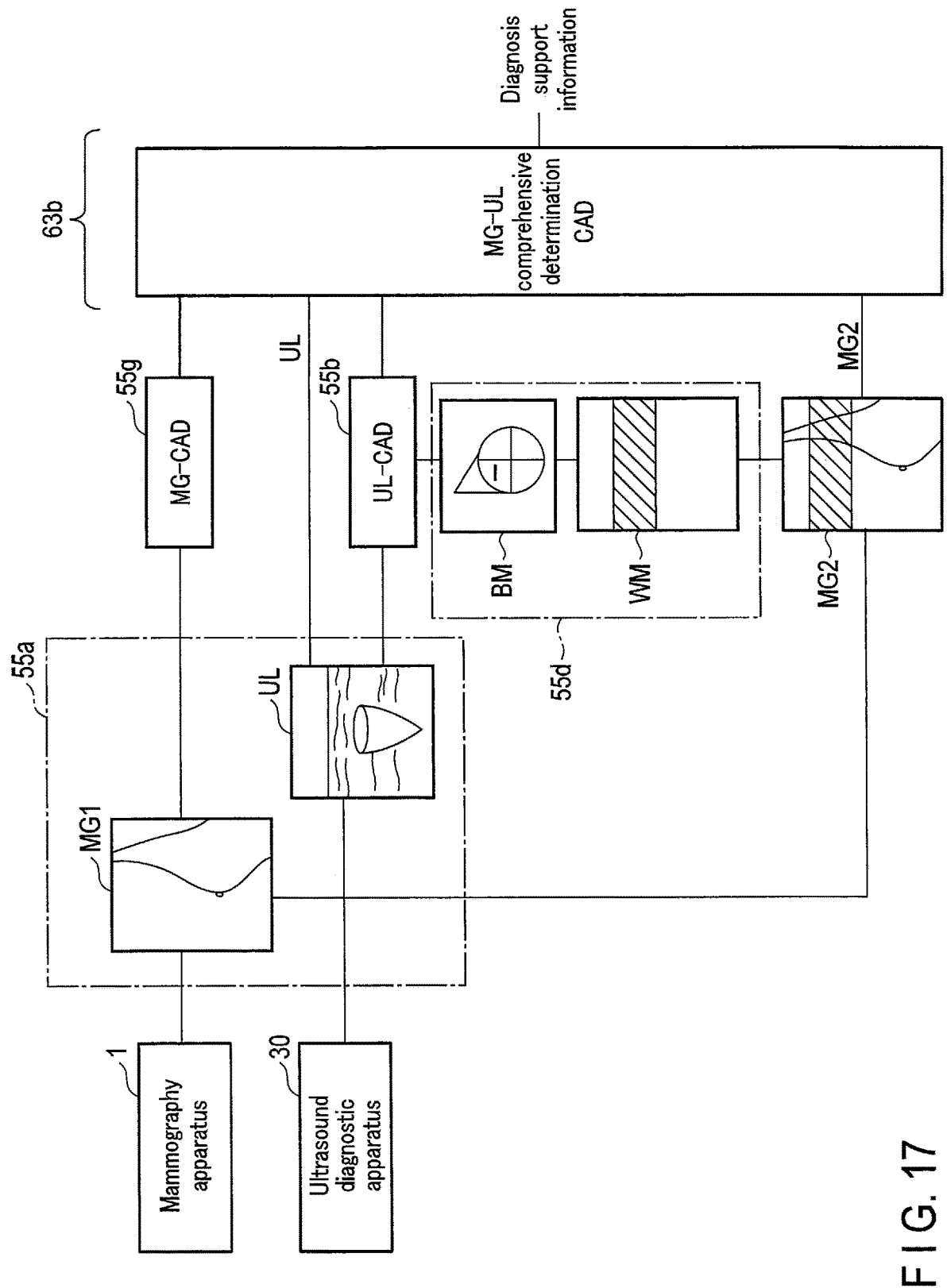
F I G. 17

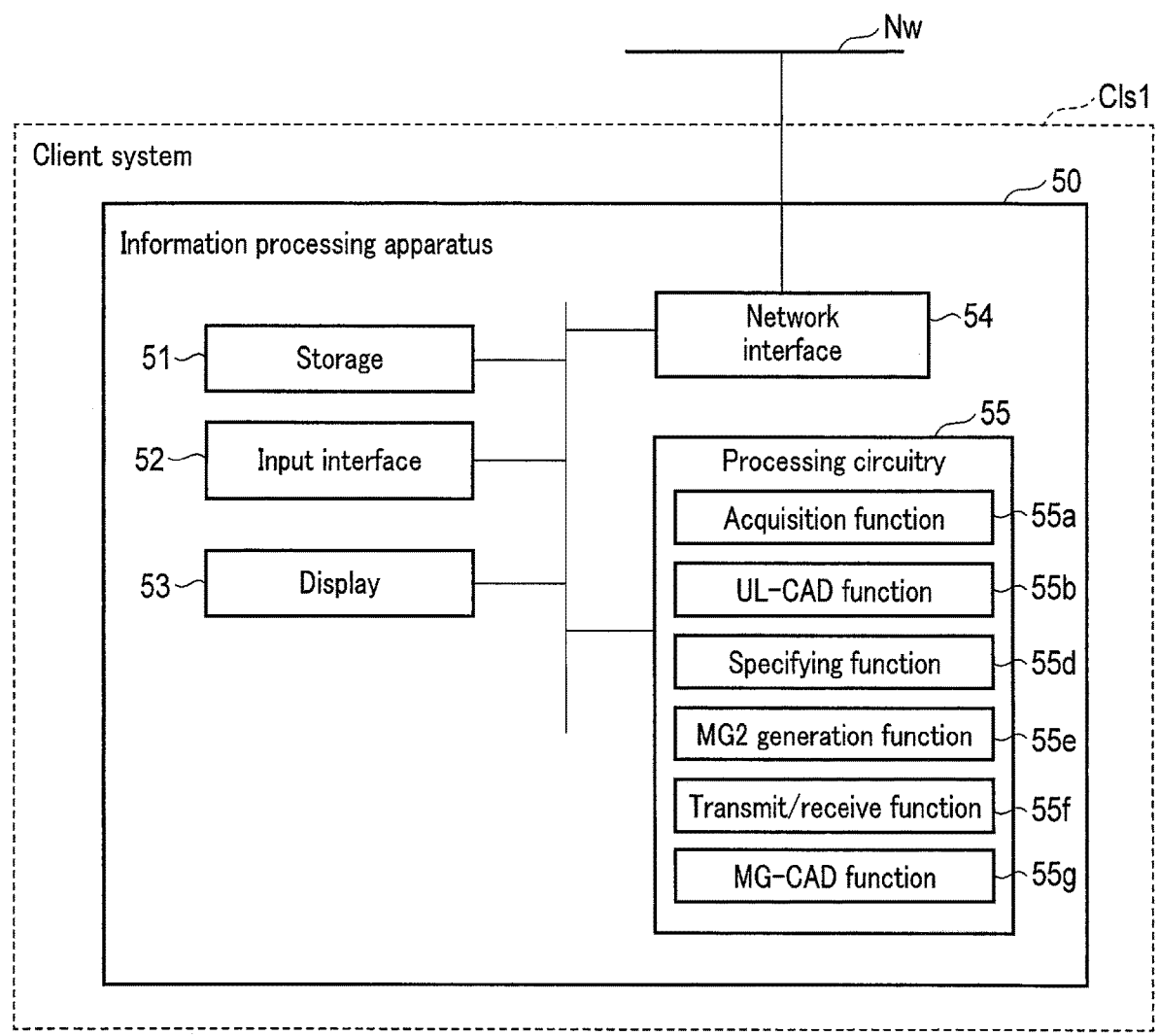
F I G. 18

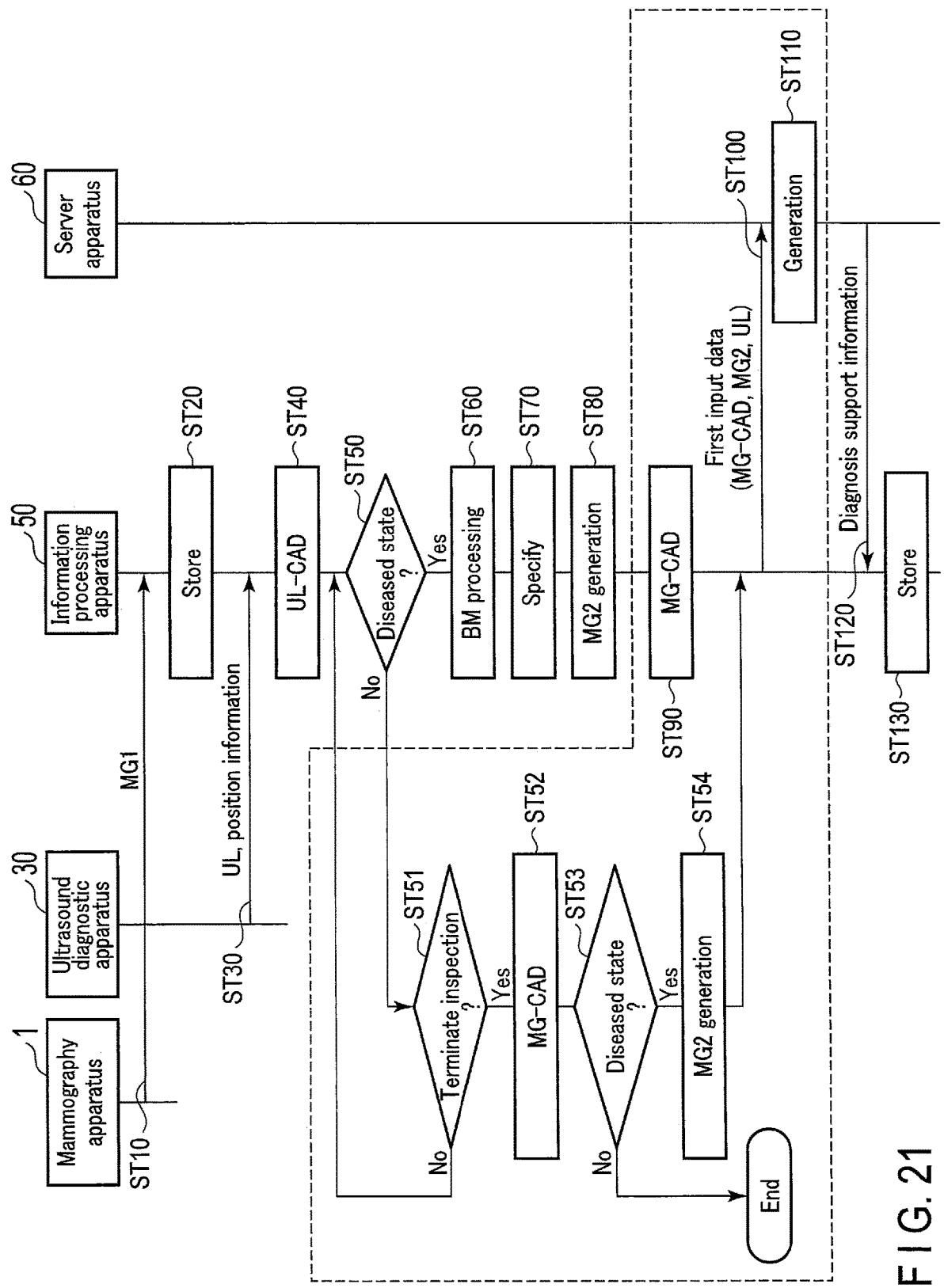
F I G. 21

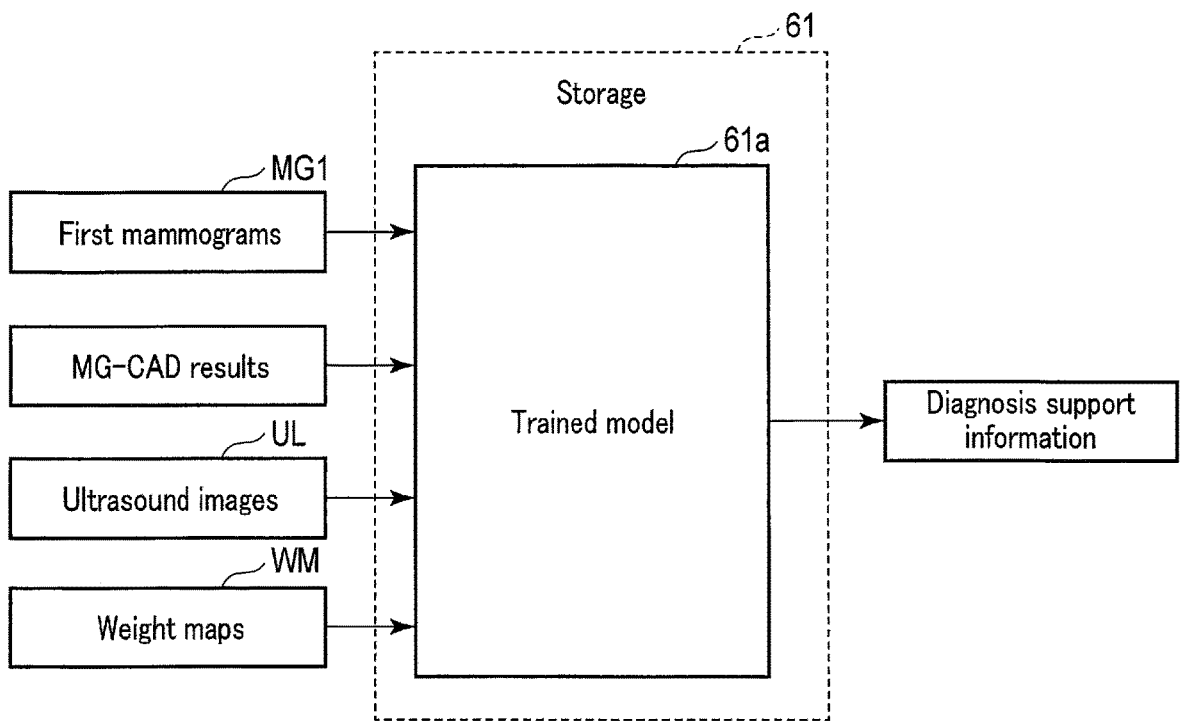
F I G. 23
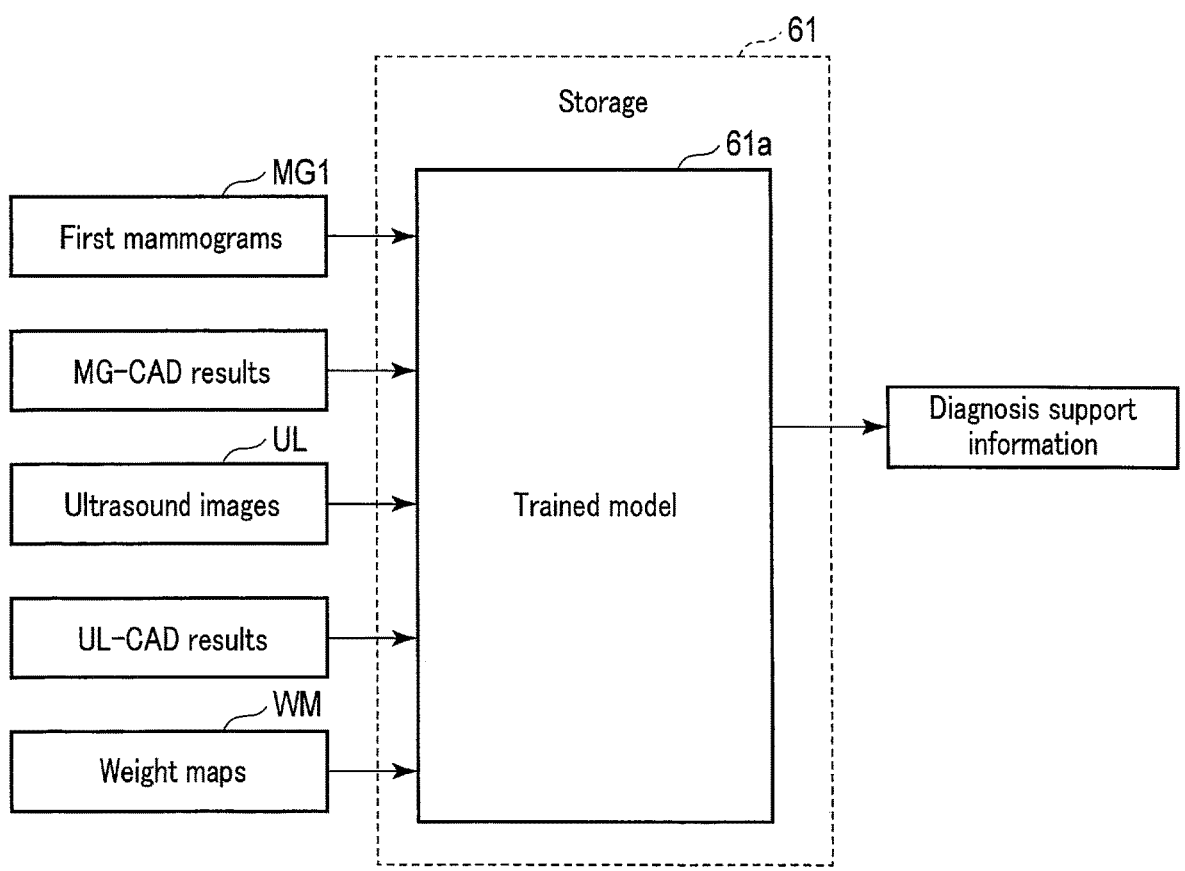
F I G. 24

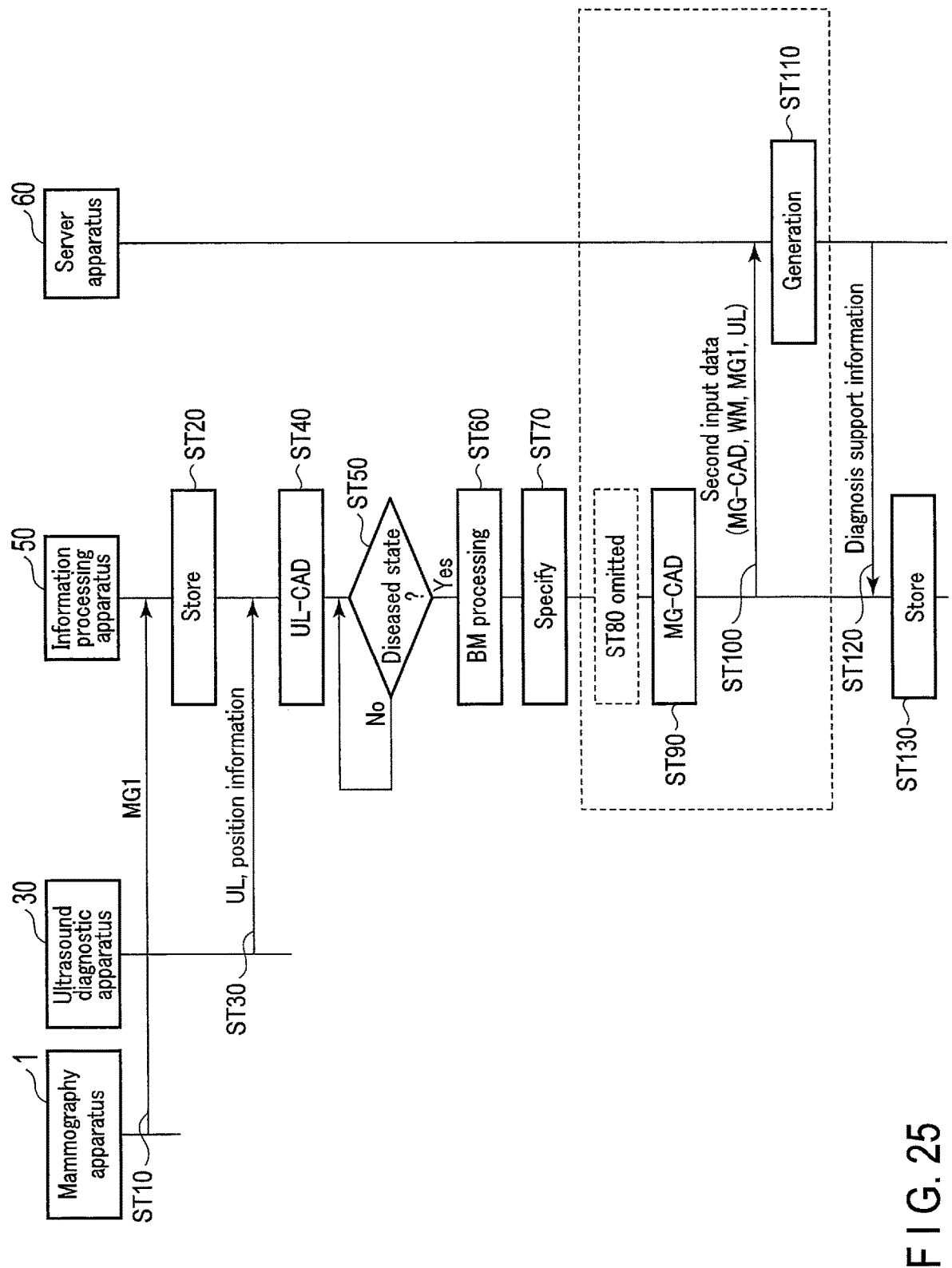
F I G. 25

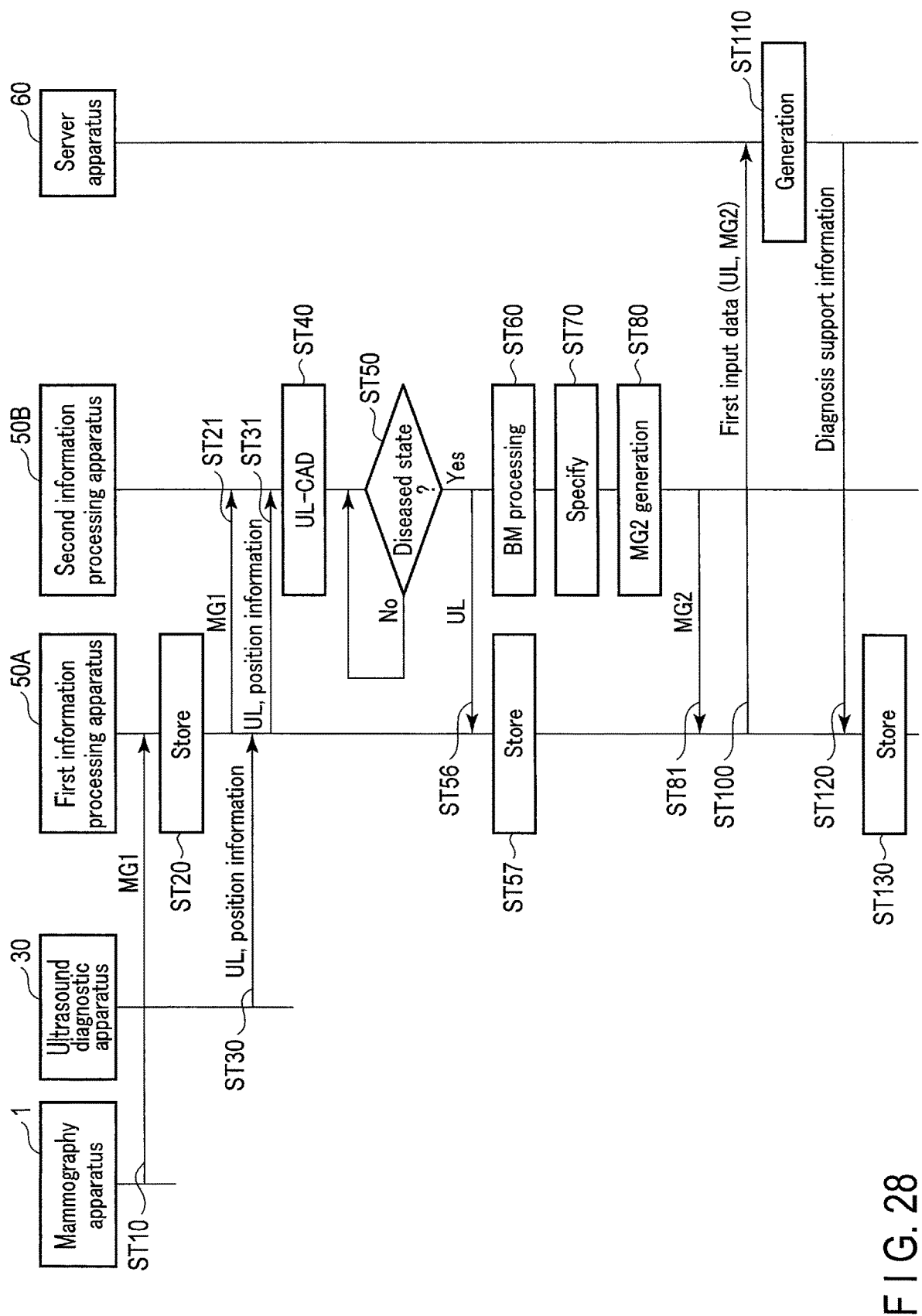
F I G. 28

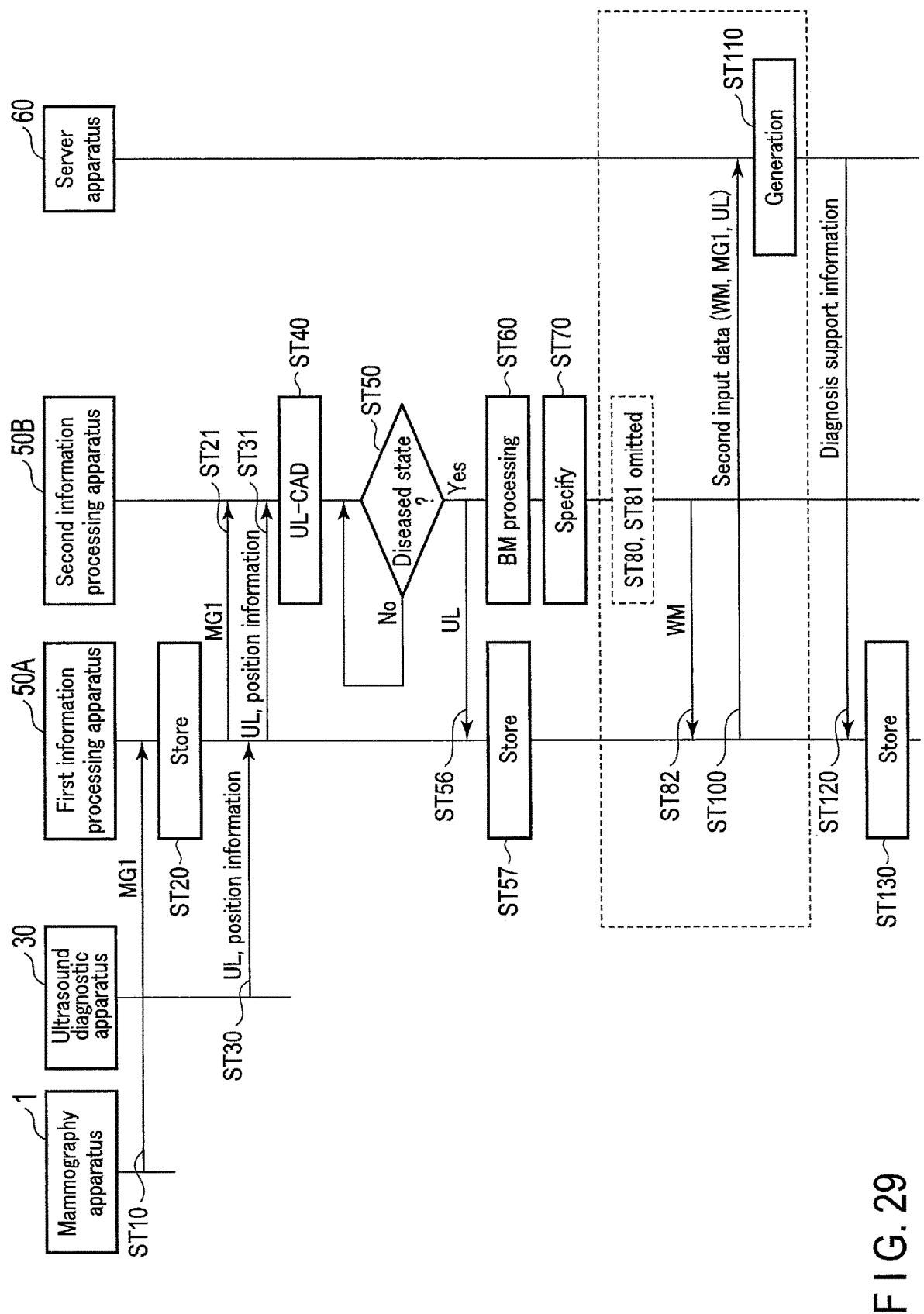
F I G. 29

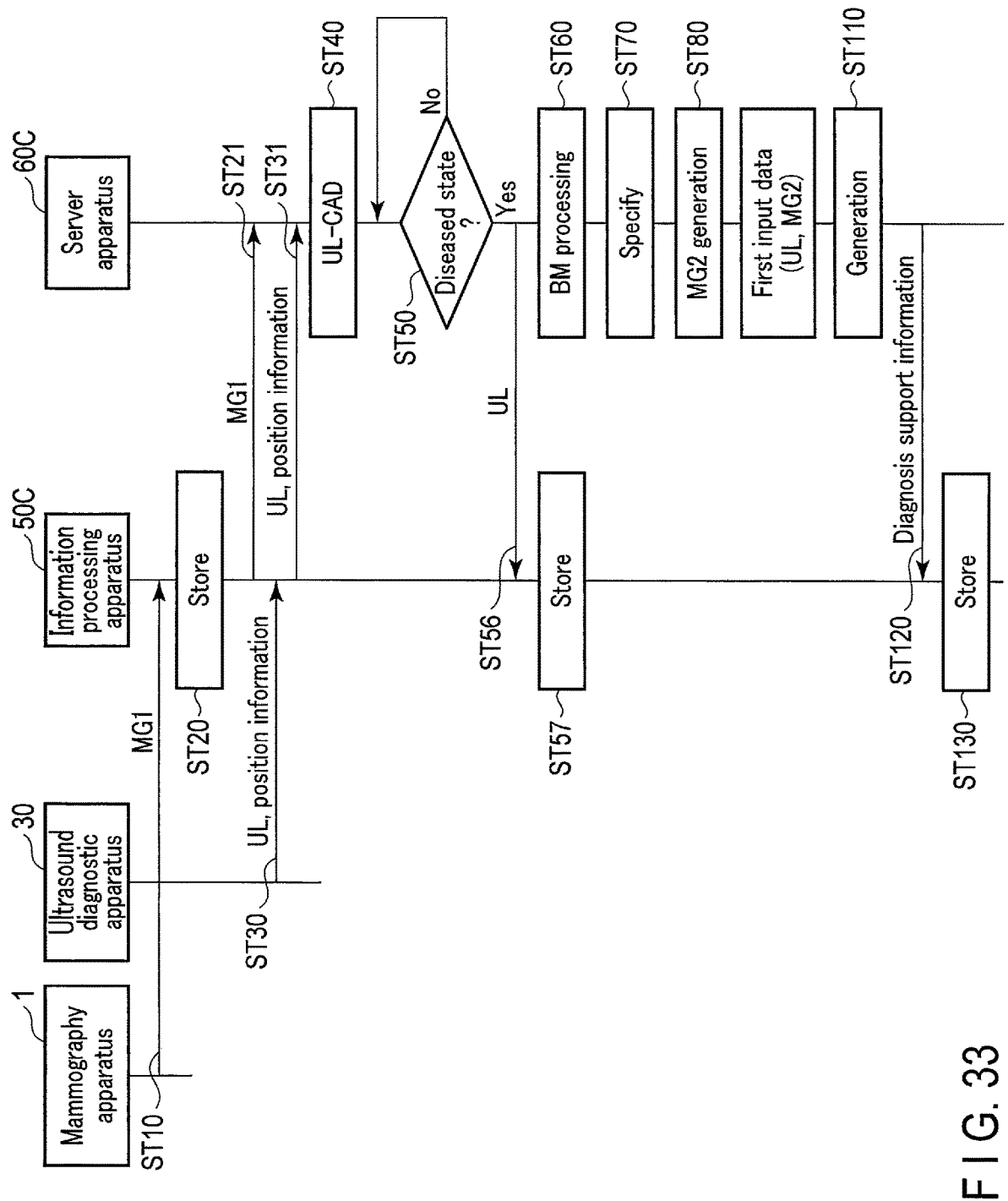
F I G. 33

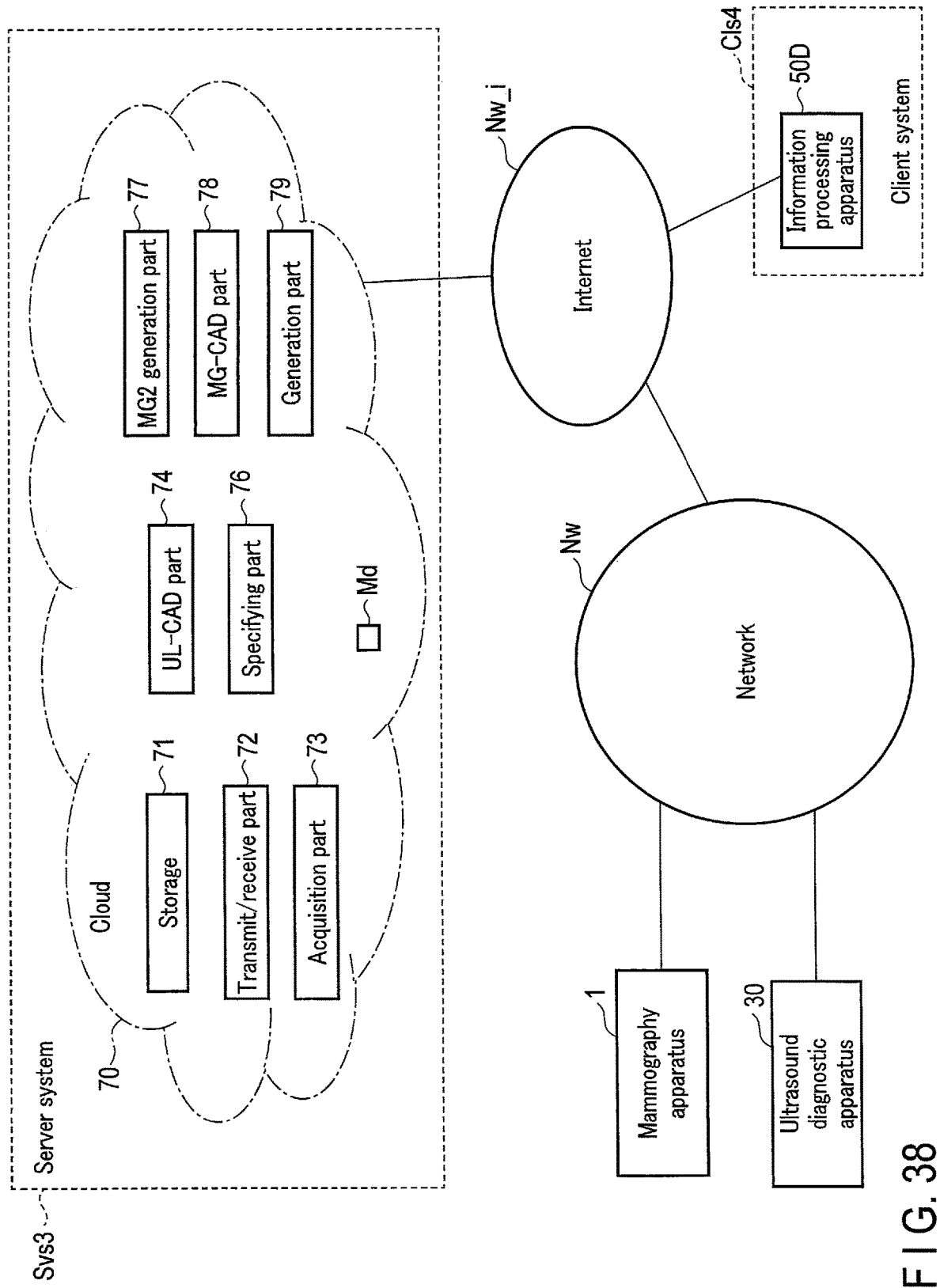
F I G. 38

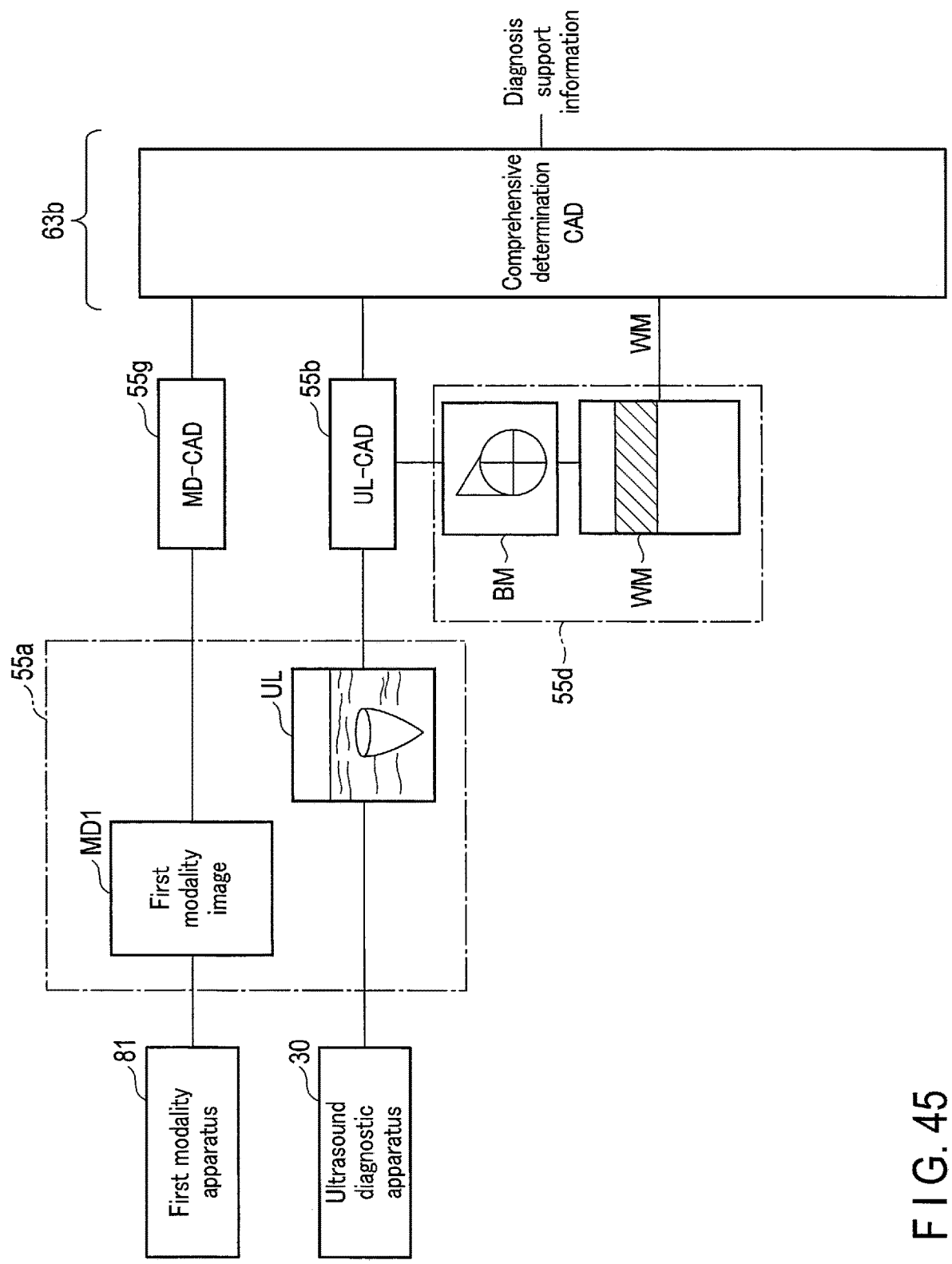
F I G. 45

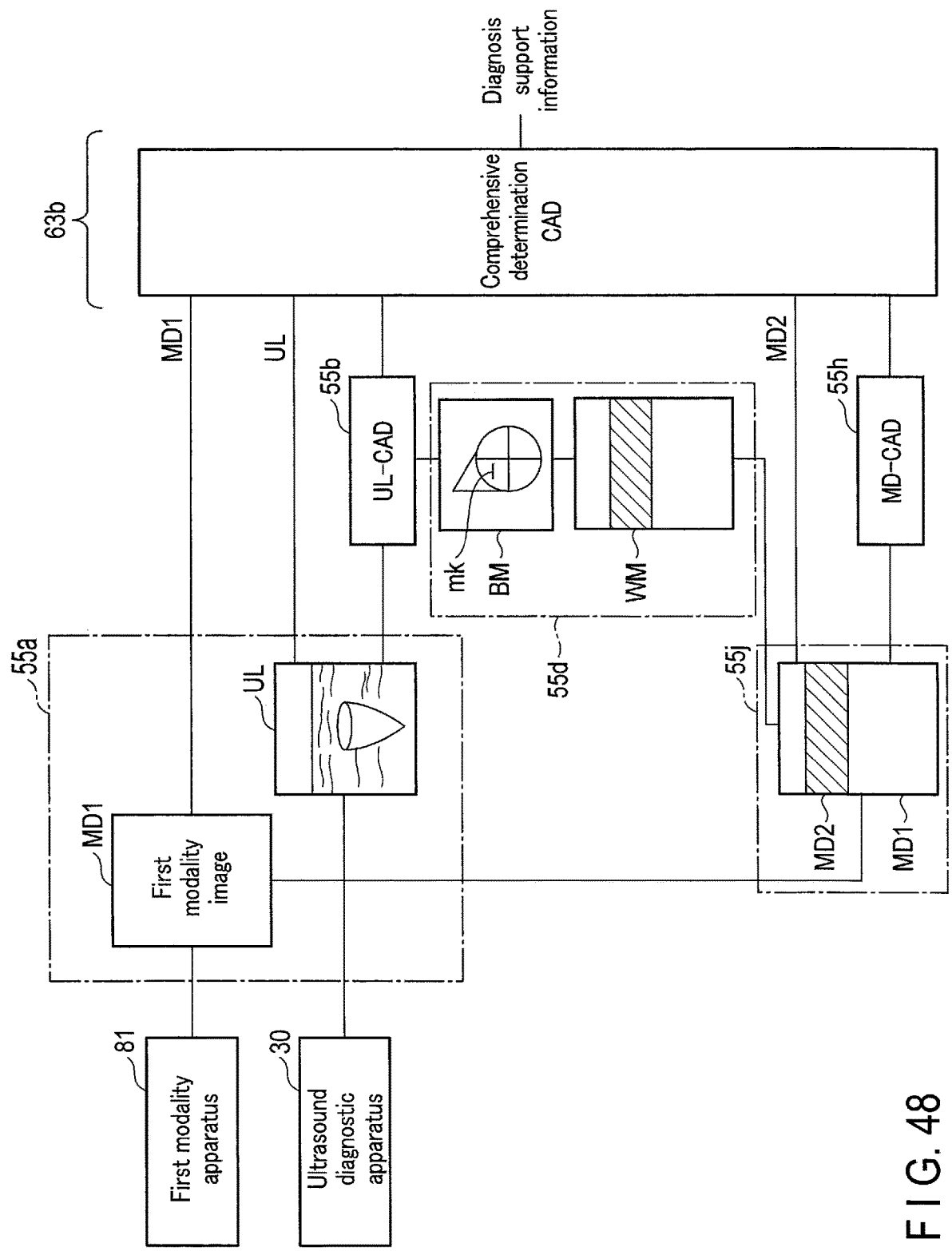
F I G. 48

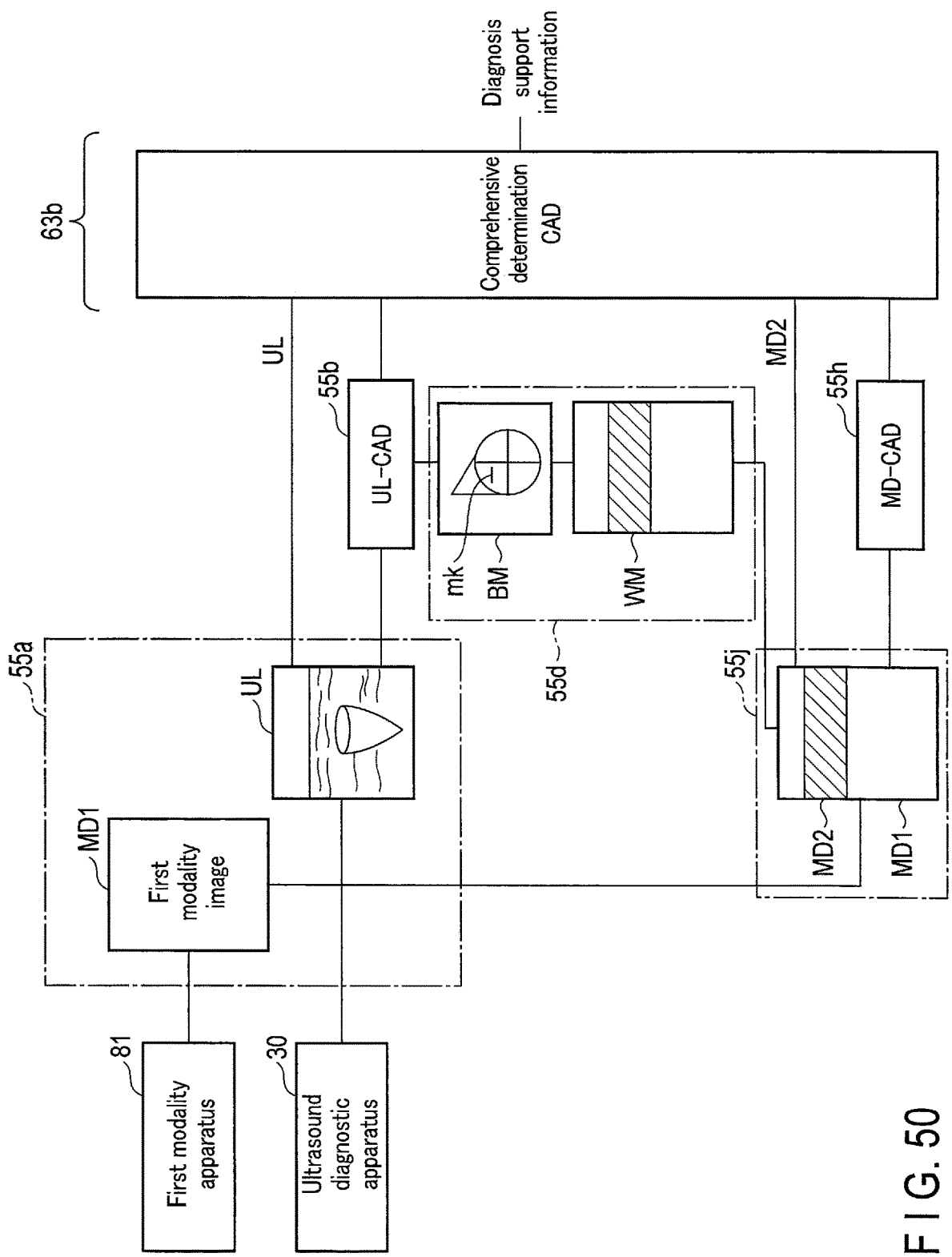
F I G. 50

MEDICAL INFORMATION PROCESSING SYSTEM AND MEDICAL INFORMATION PROCESSING METHOD

CROSS-REFERENCE TO RELATED APPLICATIONS

This is a Continuation Application of PCT application No. PCT/JP2019/18051, filed on Apr. 26, 2019, which was published under PCT Article 21(2) in Japanese.

This application is based upon and claims the benefit of priority from prior Japanese Patent Applications No. 2018-86998, filed Apr. 27, 2018, and No. 2019-84733, filed Apr. 25, 2019, the entire contents of all of which are incorporated herein by reference.

FIELD

Embodiments described herein relate generally to a medical information processing system and a medical information processing program.

BACKGROUND

In breast cancer screening, attempts have been made to comprehensively interpret mammography images and ultrasound images. However, providing a comprehensive interpretation for the same lesion at the same location in a mammogram and an ultrasound image is difficult, because a mammogram is an image of entire breast while an ultrasound image is an image of a slice of the breast. A similar difficulty is involved in cases between a modality image different from a mammogram and an ultrasound image as well.

BRIEF DESCRIPTION OF THE DRAWINGS

FIG. 3 is a perspective view showing an appearance of the mammography apparatus according to the first embodiment.

FIG. 10 is a schematic diagram for explaining a trained model according to the first embodiment.

FIG. 11 is a schematic diagram for explaining a multilayer network of a machine learning model according to the first embodiment.

FIG. 14 is a schematic diagram for explaining a trained model according to the modification of the first embodiment.

FIG. 15 is a schematic diagram for explaining a trained model according to the modification of the first embodiment.

FIG. 16 is a sequence diagram for explaining operations according to the modification of the first embodiment.

FIG. 17 is a schematic diagram showing a process according to a second embodiment, from acquisition of a first mammogram and an ultrasound image up to generation of diagnosis support information.

FIG. 18 is a block diagram showing a configuration of an information processing apparatus in a client system according to the second embodiment.

FIG. 21 is a sequence diagram for explaining operations according to the second embodiment.

FIG. 23 is a schematic diagram for explaining a trained model according to the modification of the second embodiment.

FIG. 24 is a schematic diagram for explaining a trained model according to the modification of the second embodiment.

FIG. 25 is a sequence diagram for explaining operations according to the modification of the second embodiment.

FIG. 28 is a sequence diagram for explaining operations according to the third embodiment.

FIG. 29 is a sequence diagram for explaining operations according to a modification of the third embodiment.

FIG. 33 is a sequence diagram for explaining operations according to the fourth embodiment.

FIG. 38 is a block diagram showing a configuration of a medical information processing system according to a sixth embodiment.

FIG. 45 is a schematic diagram showing, as one modification applicable to the further modification of the second embodiment, a process from acquisition of a first modality image and an ultrasound image up to generation of diagnosis support information.

FIG. 48 is a schematic diagram showing, as one modification applicable to each of the foregoing embodiments and modifications, a process from acquisition of a first modality image and an ultrasound image up to generation of diagnosis support information.

FIG. 50 is a schematic diagram showing, as one modification applicable to each of the foregoing embodiments and modifications, a process from acquisition of a first modality image and an ultrasound image up to generation of diagnosis support information.

DETAILED DESCRIPTION

According to one embodiment, a medical information processing system includes processing circuitry. The processing circuitry is configured to acquire an ultrasound image of a subject. The processing circuitry is configured to acquire a first modality image of the subject, the first modality image differing from the ultrasound image. The processing circuitry is configured to acquire an imaging position for the ultrasound image. The processing circuitry is configured to generate diagnosis support information for the subject based on the ultrasound image, the imaging position for the ultrasound image, and the first modality image.

Therefore, the modality image and the ultrasound image are comprehensively interpreted so that the diagnosis can be assisted.

The embodiments will be described with reference to the drawings.

First Embodiment

Figure 1:
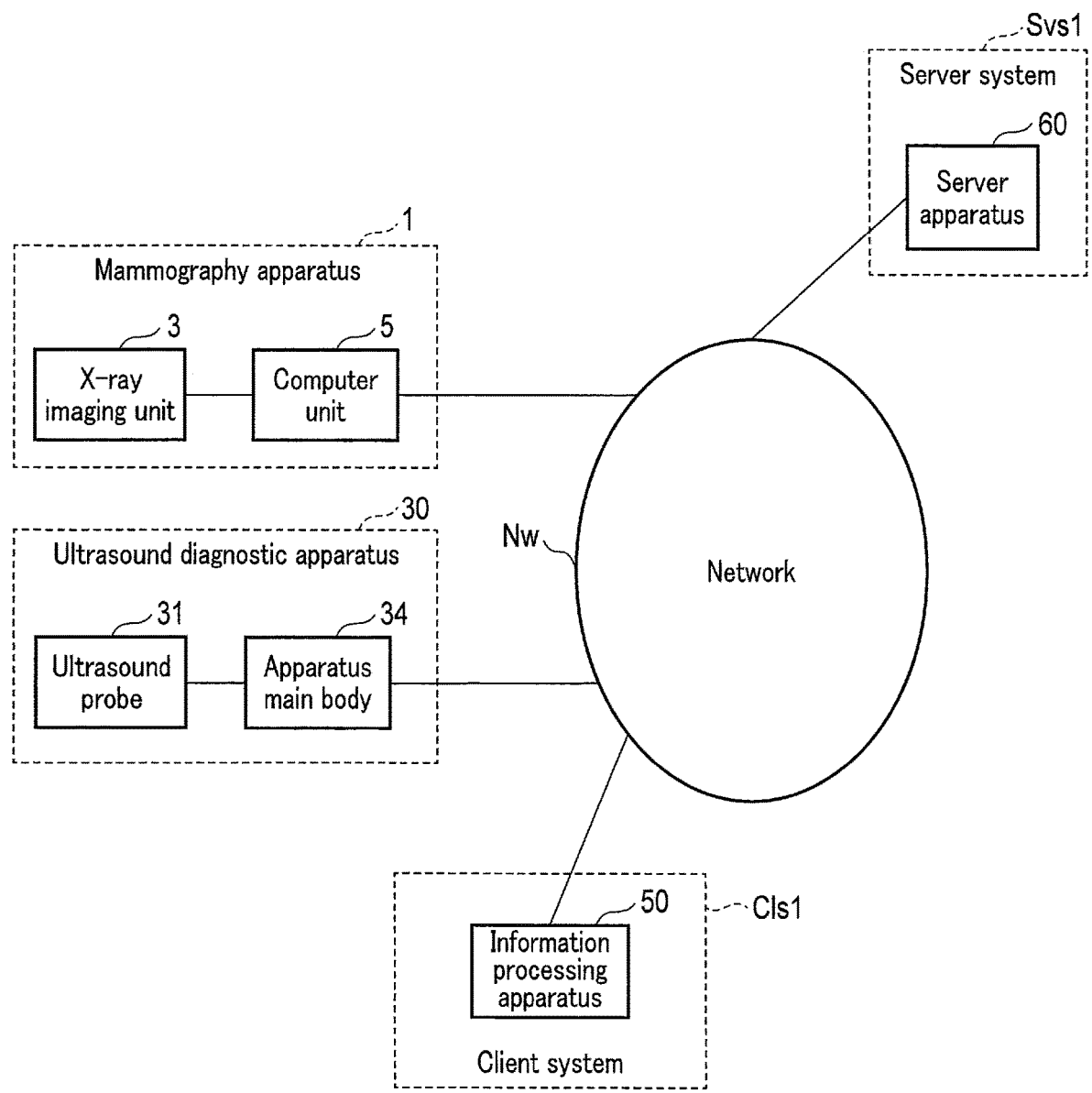
FIG. 1 is a block diagram showing a configuration of a medical information processing system according to a first embodiment.

FIG. 1 is a block diagram showing a configuration of a medical information processing system according to the first embodiment. This medical information processing system includes a client system Cls1 and a server system Svs1. The client system Cls1 and the server system Svs1, and also a mammography apparatus 1 and an ultrasound diagnostic apparatus 30 are adapted to communicate with each other via a network NW. The network Nw may be, for example, a local area network (LAN) such as a hospital network. The client system Cls1 includes at least one information processing apparatus 50. The server system Svs1 includes at least one server apparatus 60. The description of this embodiment will assume an exemplary instance where the client system Cls1 includes one information processing apparatus 50 and the server system Svs1 includes one server apparatus 60. It is noted that the term "system" in the disclosure herein covers not only the cases where the system includes multiple apparatuses, but also the cases where the system consists of a single apparatus. This does not mean that only the client system and the server system each consist of a single apparatus, but the whole medical information processing system may consist of a single apparatus. In other words, a medical information processing system consisting of a single apparatus may be provided to communicate with a modality apparatus (e.g., the mammography apparatus 1) and the ultrasound diagnostic apparatus. The modality apparatus here is intended to be a medical image diagnostic apparatus different from the ultrasound diagnostic apparatus, and examples that may be suitably employed as the modality apparatus include a mammography apparatus, a magnetic resonance imaging (MRI) apparatus, a positron emission mammography (PEM) apparatus, a positron emission tomography (PET) apparatus, a computed tomography (CT) apparatus, and so on. The description will mainly use examples where the mammography apparatus 1 serves as the modality apparatus. Note also that the medical information processing system may be integral with the mammography apparatus 1 or the ultrasound diagnostic apparatus 30. In such an exemplary configuration, each function of the medical information processing system may be realized by the operation of processing circuitry 26 of the mammography apparatus 1 or the operation of processing circuitry 42 of the ultrasound diagnostic apparatus 30. Also, the client system may be integral with the mammography apparatus 1 or the ultrasound diagnostic apparatus 30. In such an exemplary configuration, each function of processing circuitry 55 of the information processing apparatus 50 in the client system Cls1 may be realized by the processing circuitry 26 of the mammography apparatus 1 or the processing circuitry 42 of the ultrasound diagnostic apparatus 30. This applies to each of the following embodiments.

Figure 2:
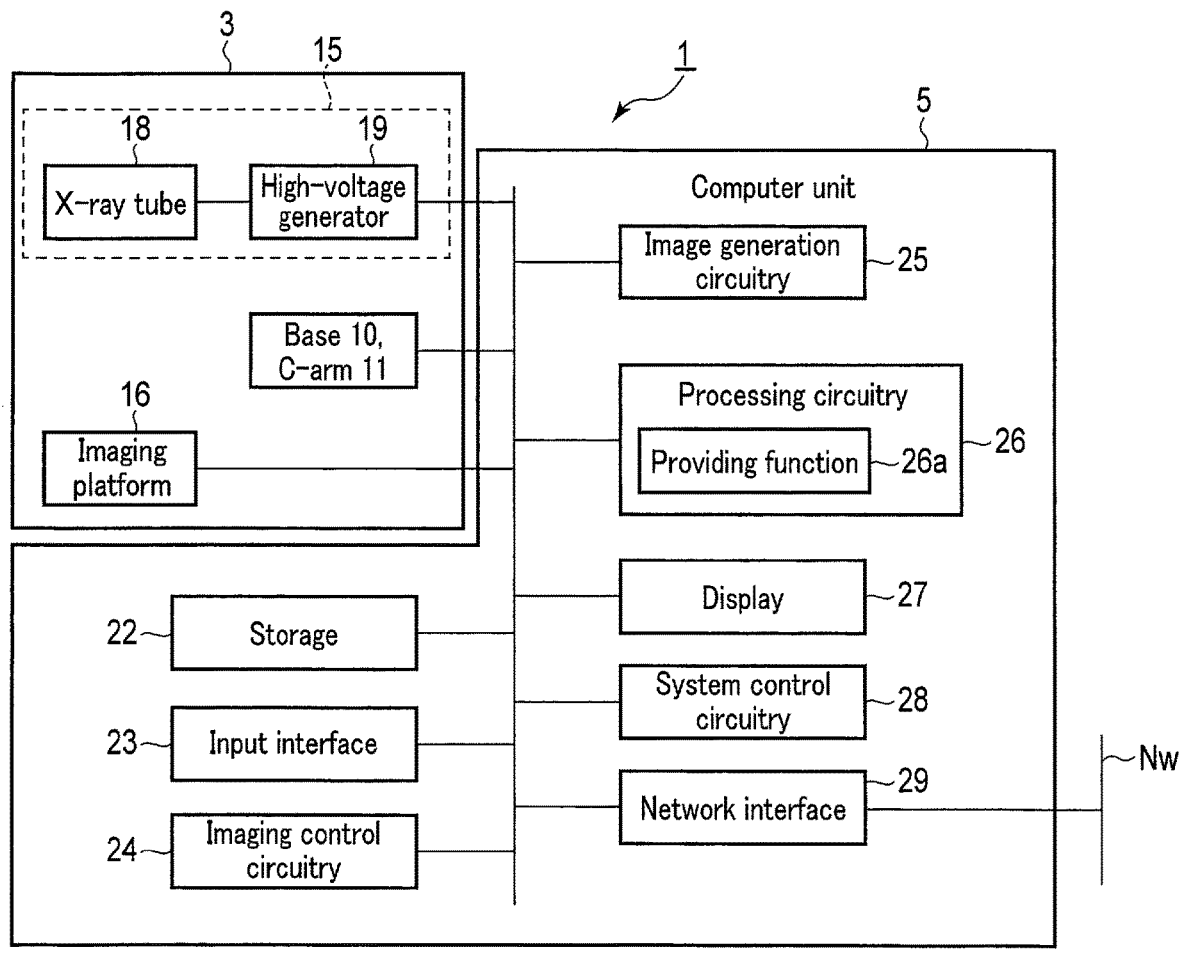
FIG. 2 is a block diagram showing a configuration of a mammography apparatus according to the first embodiment.

The mammography apparatus 1 includes an X-ray imaging unit 3 and a computer unit 5 as shown in FIGS. 2 and 3.

The X-ray imaging unit 3 includes a base 10 and a C-arm 11. The C-arm 11 is attached to a shaft 12 projecting from the base 10. The C-arm 11 is thus supported by the base 10 so that it can rotate about the center of the shaft 12, i.e., a central axis X for rotation. Rotation of the C-arm 11 enables operations for imaging in directions including a CranioCaudal (CC) direction, a MedioLateral (ML) projection direction, and a MedioLateral Oblique (MLO) projection direction.

The C-arm 11 is constituted by an arm body 14 furnished with an X-ray generator 15, an imaging platform 16, and a compression unit 17. The X-ray generator 15 and the imaging platform 16 are arranged at the respective ends of the arm body 14. The compression unit 17 is arranged midway between the X-ray generator 15 and the imaging platform 16.

The X-ray generator 15 includes an X-ray tube 18 and a high-voltage generator 19. The X-ray tube 18 is adapted to receive a tube voltage application and a filament current supply from the high-voltage generator 19 and output X-rays toward the compression unit 17 for a predetermined X-ray continuation period. The tube voltage for application and the X-ray continuation period are adjusted into values that are suitable for imaging operations, based on control signals received from later-described imaging control circuitry 24.

The X-ray tube 18 includes a cathode filament and an anode. The anode may be any of an Mo anode formed of molybdenum (Mo), an Rh anode formed of rhodium (Rh), an Mo—Rh anode formed of a mixture of Mo and Rh, a W anode formed of tungsten (W), and so on. Multiple such anodes may be provided so that they can be discretionarily switched according to the control signals from the imaging control circuitry 24.

With the filament current supply, the cathode filament is heated and generates thermal electrons. With the tube voltage application between the cathode filament and the anode, the generated thermal electrons are caused to collide with the anode. The thermal electrons colliding with the anode thus generate X-rays. As the thermal electrons fly and collide with the anode, a tube current flows. The tube current is adjusted by the filament current. The X-ray dose during an imaging operation is controlled by adjusting a tube current-time product, which is a product of the tube current multiplied by the X-ray continuation period (time), according to the control signals from the imaging control circuitry 24.

The X-ray tube 18 is furnished with a radiation quality filter for altering the radiation quality of the X-rays generated. The radiation quality filter may be any of an Mo filter formed of Mo, an Rh filter formed of Rh, an Al filter formed of aluminum (Al), an Ag filter formed of silver (Ag), a filter formed of a mixture of such materials, and so on. Multiple of these filters may be provided so that they can be discretionarily switched according to the control signals from the imaging control circuitry 24.

The compression unit 17 includes a compression plate 17a supported by the C-arm 11 in such a manner as to be capable of making an approaching and separating movement with respect to a placement surface 16a of the imaging platform 16. The compression unit 17 is adapted to move the compression plate 17a according to the control signals from the imaging control circuitry 24 so that the subject's breast is pressed against the placement surface 16a and set to a predetermined thickness state.

The imaging platform 16 is a housing unit containing a digital detector such as a flat panel detector (FPD) for detecting X-rays transmitted through the breast. The imaging platform 16 is supported by the C-arm 11 in such a manner as to be capable of approaching and separating from the X-ray tube 18 along an axis Z which connects the plane center of the placement surface 16a with the focal point of the X-ray tube 18. Here, an axis Y orthogonal to both the axis X and the axis Z is assumed. Accordingly, the X-Y-Z coordinate system is a rotating coordinate system with the axis X serving as a central axis for rotation. The axis Z defines the thickness direction of the breast, and the X-Y plane defines the spreading directions perpendicular to the thickness direction of the breast.

Also, the compression unit 17 may include an upper compression plate and a lower compression plate. In order to perform magnification imaging with the placement surface 16a distant from the breast compressed between the upper and lower compression plates, the housing of the imaging platform 16 may be replaced with a housing for magnification imaging so that a suitable magnification ratio is obtained.

The digital detector in the imaging platform 16 includes multiple direct-conversion type semiconductor detecting elements adapted to convert incident X-rays directly into electric signals, or multiple indirect-conversion type semiconductor detecting elements adapted to convert incident X-rays into light by fluorescent components and then convert the light into electric signals. These semiconductor detecting elements are arrayed in a two-dimensional grid. The digital detector also includes an amplifier circuit and an A/D converter circuit in addition to the semiconductor detecting elements, e.g., photodiodes. Thus, signal charges occurring at the multiple semiconductor detecting elements upon X-ray incidence are relayed through the amplifier circuit and the A/D converter circuit, and output as digital signals to the computer unit 5.

The computer unit 5, for common use with the X-ray imaging unit 3, includes storage 22, an input interface 23, the imaging control circuitry 24, image generation circuitry 25, the processing circuitry 26, a display 27, and system control circuitry 28.

The storage 22 is constituted of a memory for storing electric information, such as a read only memory (ROM), a random access memory (RAM), a hard disk drive (HDD), an image memory, etc. The storage 22 is also constituted of peripheral circuitry pertaining to the memory, such as a memory controller, a memory interface, etc. The storage 22 is adapted to store, for each inspection of the breast of a subject, a first mammogram of the imaged breast, and at least MLO angle information indicative of the imaging angle for this first mammogram. For example, the storage 22 may store, for each inspection, data of the first mammogram generated by the image generation circuitry 25 in association with imaging conditions, a code indicative of the imaging direction (imaging angle) used at the imaging, and a code indicative of whether the imaged subject is the right breast or the left breast. Note that the first mammogram is one example of a first modality image. The first modality image is a modality image different from an ultrasound image and may be any of a mammogram, a magnetic resonance imaging (MRI) image, a positron emission mammography (PEM) image, a positron emission tomography (PET) image, and a computed tomography (CT) image.

The input interface 23 is realized by components for an operator to input various instructions, commands, information sets, selections, settings, etc., to the computer unit 5 and such components include a trackball, switch buttons, a mouse, a keyboard, a touch pad which allows input operations through contacting of the operation screen, and a touch panel display which integrates a display screen and a touch pad. The input interface 23 is connected to the imaging control circuitry 24, the processing circuitry 26, etc., and adapted to convert input operations received from the operator into electric signals and to output the electric signals to the imaging control circuitry 24, the processing circuitry 26, etc. In the disclosure herein, the input interface 23 is not limited to physical operating components such as a mouse and a keyboard. That is, the examples of the input interface 23 also include processing circuitry for electric signals that is adapted to receive an electric signal corresponding to an input operation from an external input device separate from the apparatus, and to output this electric signal to the imaging control circuitry 24, the processing circuitry 26, etc.

The input interface 23 serves as an operation panel for setting imaging conditions (tube voltage, tube current-time product, anode material, radiation quality filter material, breast thickness, distance between the X-ray focal point and the X-ray detector, magnification ratio, etc.) to the imaging control circuitry 24. Using the input interface 23, a code indicative of whether the imaging is performed on the right breast or the left breast is also set to the imaging control circuitry 24. The input interface 23 also serves as an interface for manipulating the C-arm 11, and operating the input interface 23 can thus rotate the C-arm 11 about the axis Z and set it in a desired position. The imaging direction is determined according to the set position of the C-arm 11.

The imaging control circuitry 24 includes a processor and a memory (not illustrated). The imaging control circuitry 24 is adapted to control each component of the X-ray imaging unit 3 based on the imaging conditions (tube voltage, tube current-time product, anode material, radiation quality filter material, breast thickness, distance between the X-ray focal point and the X-ray detector, magnification ratio, etc.) set via the input interface 23. The imaging control circuitry 24 thus causes the X-ray imaging unit 3 to perform X-ray imaging according to the setting.

The image generation circuitry 25 is adapted to generate two-dimensional image data based on the digital signals from the imaging platform 16. Normally, an area representing a living object in the images acquired by X-ray imaging encompasses not only a breast region but also a region other than the breast region, such as a region of a greater pectoral muscle.

The processing circuitry 26 is adapted to read the first mammogram, the angle information, and a control program from the storage 22 according to an operator's instruction input via the input interface 23, and to control the computer unit 5 based on these. For example, the processing circuitry 26 is a processor to realize, in addition to an existing ultrasound diagnosis support function, various functions for assisting the ultrasound diagnosis support function according to the control program read from the storage 22. Such various functions include, for example, a providing function 26a. Note that the existing ultrasound diagnosis support function refers to a function to plot, on a body mark (schematic diagram) of the breast, an approximate position of a region of interest that has been discovered from the first mammograms. More specifically, a region of interest is set at a given position (pointing step) on each of two first mammograms acquired in different imaging directions, and two straight lines covering the respective positions of the region of interest and extending along the respective imaging directions are plotted on the body mark of the breast. This ultrasound diagnosis support function, where the approximate position of the region of interest is expressed as an intersection of the two straight lines on the body mark of the breast, provides an advantage of facilitating the scanning of the region of interest that uses an ultrasound probe 31. However, the existing ultrasound diagnosis support function is not essential, and may be omitted.

The providing function 26a is a function to provide (transmit), in response to a request from other apparatuses, data including, e.g., the first mammogram and the angle information to the requestor. Providing the angle information may be omitted if a fixed imaging direction is employed. Also, when the existing ultrasound diagnosis support function is in use, the providing function 26a provides the body mark showing a plotted region of interest to the requestor together with the first mammogram. Said other apparatuses as requestors include, for example, the information processing apparatus 50 in the client system Cls1.

The display 27 includes a display main part for displaying medical images, etc., internal circuitry for supplying signals for display to the display main part, and peripheral circuitry including connectors, cables, or the like for connection between the display main part and the internal circuitry. The display 27 is adapted to display, under the control of the processing circuitry 26, the first mammograms generated by the image generation circuitry 25 and the schematic diagram (body mark BM) generated by the processing circuitry 26.

The system control circuitry 28 includes a processor and a memory (not illustrated), and serves as a center of the mammography apparatus 1 to control each component.

A network interface 29 is provided as circuitry for connecting the computer unit 5 to the network Nw for communications with other apparatuses such as the ultrasound diagnostic apparatus 30, the information processing apparatus 50, and the server apparatus 60. As the network interface 29, for example, a network interface card (NIC) may be adopted. In the following disclosure, such a description as the network interface 29 being involved in communications with other apparatuses will be omitted.

Note that the computer unit 5 and the X-ray imaging unit 3 may be an integral unit.

Figure 4:
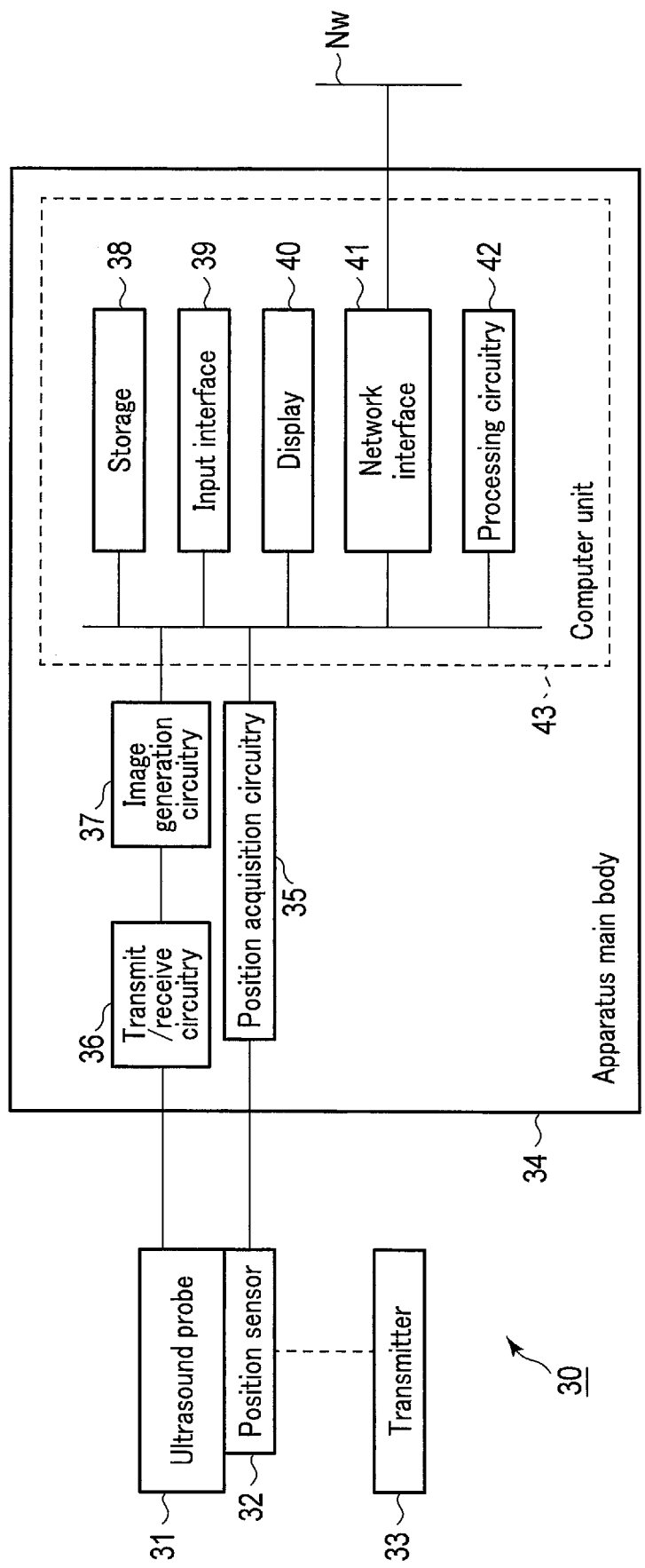
FIG. 4 is a block diagram showing a configuration of an ultrasound diagnostic apparatus according to the first embodiment.

Turning to the ultrasound diagnostic apparatus 30, it includes the ultrasound probe 31, a position sensor 32, a transmitter 33, and an apparatus main body 34, as shown in FIG. 4. The apparatus main body 34 includes position acquisition circuitry 35, transmit/receive circuitry 36, image generation circuitry 37, storage 38, an input interface 39, a display 40, a network interface 41, and processing circuitry 42. Part or the whole of the apparatus main body 34 may constitute a computer unit. For example, part of the apparatus main body 34 that includes the storage 38, the input interface 39, the display 40, the network interface 41, and the processing circuitry 42 may constitute a computer unit 43.

The ultrasound probe 31 includes piezoelectric vibrators which are constituted by piezoelectric ceramics or the like and function as acoustic/electric reversible converters. The multiple piezoelectric vibrators, aligned in parallel arrangements, are furnished at the distal end of the ultrasound probe 31. The description will assume a configuration where one piezoelectric vibrator forms one channel. The piezoelectric vibrators are adapted to generate ultrasound in response to drive signals supplied from the transmit/receive circuitry 36. The piezoelectric vibrators are also adapted to generate reception echo signals upon receiving the ultrasound that has been reflected by the subject's living tissue. The ultrasound probe 31 may be a mechanical four-dimensional probe which performs three-dimensional scanning by swinging the one-dimensional array in the direction orthogonal to the alignment direction of the vibrators, or a two-dimensional array probe.

The position sensor 32 is adapted to acquire a position angle detection signal for the ultrasound probe 31 by referring to a predetermined reference position. The position angle detection signal is a detection signal corresponding to the position and the angle of the ultrasound probe 31 with respect to the predetermined reference position. The angle of the ultrasound probe 31 is, for example, an inclination of the ultrasound probe 31 with respect to a predetermined reference direction. The predetermined reference position may be, for example, the position of the ultrasound diagnostic apparatus 30. The predetermined reference direction may be based on, for example, the preset three orthogonal axes. The position sensor 32 is provided at, for example, the ultrasound probe 31. The position sensor 32 is adapted to output the acquired position angle detection signal to the position acquisition circuitry 35.

Examples of the position sensor 32 include a magnetic sensor, an infrared sensor, an angle sensor, an angular velocity sensor (e.g., gyro sensor), and so on. If, for example, the position sensor 32 is a magnetic sensor, it detects magnetism transmitted from the transmitter 33 to acquire the position angle detection signal with respect to the predetermined reference position. If the position sensor 32 is an infrared sensor, it detects infrared rays transmitted from the transmitter 33 to acquire the position angle detection signal with respect to the predetermined reference position. The infrared rays here may be replaced with more popular electromagnetic rays. Note that the reference position in the case of the position sensor 32 being a magnetic sensor may be the position of the transmitter 33. The reference position in the case of the position sensor 32 being an infrared sensor may also be the position of the transmitter 33. The reference position is suitably adjustable according to an operator's instructions input via the input interface 39. Additionally, the predetermined reference position may be a position that makes initial contact with the subject's body surface.

In the case of an angle sensor, an angle of the ultrasound probe 31 is detected. In the case of an angular velocity sensor, an angular velocity corresponding to the movement of the ultrasound probe 31 is detected. The angle of the ultrasound probe 31 may instead be determined based on two positions output from two magnetic sensors, two infrared sensors, or a pair of a magnetic sensor and an infrared sensor, arranged on the sides of the ultrasound probe 31.

The transmitter 33 is a transmission device adapted to transmit reference signals for detection by the position sensor 32. Examples that may be suitably employed as the transmitter 33 include a magnetic transmitter adapted to generate magnetism, an infrared transmitter adapted to generate infrared rays, and so on.

The position sensor 32 and the transmitter 33 as above are used for a fusion function of the ultrasound diagnostic apparatus 30. In one exemplary implementation, the position sensor 32 is attached to the ultrasound probe 31. The transmitter 33 is arranged near the subject (or the apparatus main body 34). The position acquisition circuitry 35, which will be described later, calculates the position (X, Y, Z) and the angle of the position sensor 32 with reference to the transmitter 33, based on the position angle detection signal acquired from the transmitting and receiving actions between the transmitter 33 and the position sensor 32. For the fusion function, accordingly, the position and the angle of the ultrasound probe 31 that correspond to a currently displayed ultrasound image can be obtained. Subsequently, same-location cross sections (Z) from the ultrasound image and a different volume data-based MPR image are displayed, and position alignment (registration) is performed in such a manner as to register the position angle information for the corresponding positions in the same-location cross sections.

The position acquisition circuitry 35 is adapted to use the position angle detection signal output from the position sensor 32 to calculate the position and the angle of the ultrasound probe 31 with respect to the predetermined reference position. More specifically, the position acquisition circuitry 35 acquires position information including the position and the angle of the ultrasound probe 31 in an absolute coordinate system that is based on the predetermined reference position. The description will refer to the position of the ultrasound probe 31 specified on the absolute coordinate system as a probe coordinate. The position acquisition circuitry 35 sends the acquired position information to the processing circuitry 42. The position acquisition circuitry 35 as such has a function for acquiring the position information of the ultrasound probe 31. The position information of the ultrasound probe 31 may also be called imaging position information for an ultrasound image.

The transmit/receive circuitry 36 is adapted to supply, under the control of the processing circuitry 42, a drive signal to each piezoelectric vibrator in the ultrasound probe 31. The transmit/receive circuitry 36 is also adapted to generate a reception signal based on the reception echo signal output from each piezoelectric vibrator.

The image generation circuitry 37 includes a B-mode processing unit and a Doppler processing unit (not illustrated). The B-mode processing unit is adapted to execute envelope detection and logarithmic conversion on the reception signal output from the transmit/receive circuitry 36, to give a signal value (B-mode data) for each depth in each scanning line and each ultrasound transmission/reception.

The Doppler processing unit is adapted to execute mixer processing and low-pass filter processing on the reception signal output from the transmit/receive circuitry 36, to generate a Doppler signal having a component of Doppler shift frequency fd. The Doppler processing unit may instead utilize the quadrature detection technique for generation of a Doppler signal. Here, the reception signal (RF signal) is subjected to quadrature detection so that it is converted into an IQ signal. By performing complex Fourier transform of the IQ signal, the Doppler processing unit generates the Doppler signal having a component of Doppler shift frequency fd. The Doppler signal is, for example, an echo component according to a blood flow, tissue, or a contrast medium. The Doppler processing unit is also adapted to execute processing with a moving target indicator (MTI) filter, an autocorrelation operator, etc. on the generated Doppler signal to calculate an average velocity value of the blood flow, a dispersion value, a reflection intensity of the Doppler signal, and so on. The Doppler processing unit then generates color Doppler data based on the calculation results. In the following description, the Doppler signal and the color Doppler data will be collectively called Doppler data.

Note also that the Doppler data and the B-mode data will be collectively called raw data. The raw data may be based on, among the echo signals, B-mode data according to the harmonic component of a transmitted ultrasound wave and elasticity data about the subject's biological tissue. The B-mode processing unit and the Doppler processing unit output the generated raw data to a digital scan converter (DSC), which will be described later. The B-mode processing unit and the Doppler processing unit may also be adapted to output the generated raw data to a cine memory (not illustrated).

The image generation circuitry 37 includes the DSC (not illustrated). The image generation circuitry 37 is adapted to execute coordinate conversion processing (resampling) for the DSC. The coordinate conversion processing refers to, for example, conversion of a raw data-constituted scan line signal sequence of the ultrasound scanning into a scan line signal sequence of a standard video format typically employed in televisions, etc. The image generation circuitry 37 is adapted to execute interpolation processing for the DSC, subsequently to the coordinate conversion processing. The interpolation processing refers to data interpolation between the scan line signal sequences using raw data of the adjacent scan line signal sequences.

The image generation circuitry 37 is adapted to generate ultrasound images (B-mode images and Doppler images) as display images by executing the coordinate conversion processing and the interpolation processing for the raw data. The image generation circuitry 37 may be furnished with an image memory for storing data corresponding to the generated ultrasound images. The image generation circuitry 37 is adapted to add text information, scales, etc., according to various parameters to the generated ultrasound images.

The cine memory refers to, for example, a memory for storing ultrasound images corresponding to multiple frames immediately before a freeze event. Displaying ultrasound moving images is also enabled by sequentially displaying images stored in the cine memory (performing cine display).

The storage 38 is constituted by a memory for storing electric information, such as a read only memory (ROM), a random access memory (RAM), a hard disk drive (HDD), an image memory, etc. The storage 38 is also constituted by peripheral circuitry pertaining to the memory, such as a memory controller, a memory interface, etc. The storage 38 is adapted to store various data sets such as multiple reception delay patterns differing in focus depth, control programs for its ultrasound diagnostic apparatus, diagnostic protocols, and transmission/reception conditions, as well as the B-mode data, the Doppler data, the ultrasound images (B-mode images and Doppler images) generated by the image generation circuitry 37, and so on.

The input interface 39 is realized by components for an operator to input various instructions, commands, information sets, selections, settings, etc., to the apparatus main body 34, and such components include a trackball, switch buttons, a mouse, a keyboard, a touch pad which allows input operations through contacting of the operation screen, and a touch panel display which integrates a display screen and a touch pad. The input interface 39 is connected to the processing circuitry 42 and adapted to convert input operations received from the operator into electric signals and to output the electric signals to the processing circuitry 42. In the disclosure herein, the input interface 39 is not limited to physical operating components such as a mouse and a keyboard. That is, examples of the input interface 39 also include processing circuitry for electric signals that is adapted to receive an electric signal corresponding to an input operation from an external input device separate from the apparatus, and to output this electric signal to the processing circuitry 42.

The display 40 includes a display main part for displaying medical images, etc., internal circuitry for supplying signals for display to the display main part, and peripheral circuitry including connectors, cables, or the like for connection between the display main part and the internal circuitry. The display 40 is adapted to display the ultrasound images generated by the image generation circuitry 37. The display 40 may also adjust the ultrasound images generated by the image generation circuitry 37 for brightness, contrast, dynamic range, gamma control, etc., and assign color maps to the ultrasound images.

The network interface 41 is circuitry for connecting the ultrasound diagnostic apparatus 30 to the network Nw for communications with other apparatuses. As the network interface 41, for example, a network interface card (NIC) may be adopted. In the following disclosure, such a description as the network interface 41 being involved in communications with other apparatuses will be omitted.

The processing circuitry 42 is adapted to read the transmission/reception conditions, the apparatus control program, etc. from the storage 38 according to an operator's input given via the input interface 39 that includes a mode choice, selection of a reception delay pattern list, or the start and end of transmission. The processing circuitry 42 then controls the main body of the ultrasound diagnostic apparatus based on the read information. The processing circuitry 42 is, for example, a processor having a function for controlling the transmit/receive circuitry 36, the position acquisition circuitry 35, the image generation circuitry 37, and so on according to the control program read from the storage 38. The processing circuitry 42 additionally has a function for providing (transmitting) in real time the ultrasound images generated by the image generation circuitry 37 and the position information acquired by the position acquisition circuitry 35, to the information processing apparatus 50 in the client system Cls1. Real time here means sequentially providing (transmitting) the ultrasound images and the position information in parallel with sequentially acquiring the generated ultrasound images and the transmitted position information.

Figure 5:
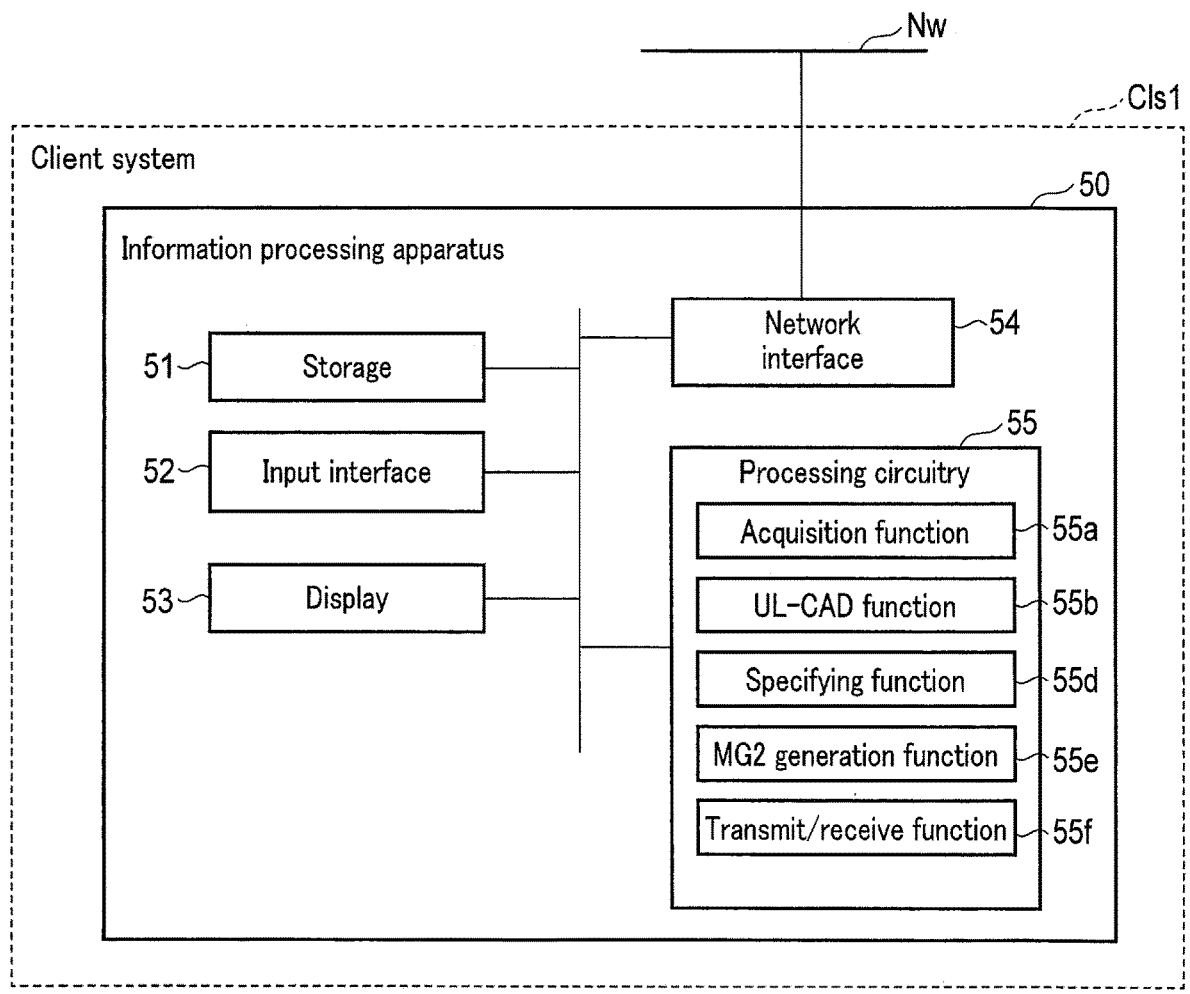
FIG. 5 is a block diagram showing a configuration of an information processing apparatus in a client system according to the first embodiment.

Turning to the information processing apparatus 50 in the client system Cls1, it includes storage 51, an input interface 52, a display 53, a network interface 54, and the processing circuitry 55, as shown in FIG. 5.

The storage 51 is constituted by a memory for storing electric information, such as a read only memory (ROM), a random access memory (RAM), a hard disk drive (HDD), an image memory, etc. The storage 51 is also constituted by peripheral circuitry pertaining to the memory, such as a memory controller, a memory interface, etc. The storage 51 is adapted to store various data sets such as control programs for its own information processing apparatus, first mammograms, angle information, body marks, ultrasound images, imaging position information for ultrasound images, and so on. There are instances where no angle information or body marks are provided. In such instances, the storage 51 does not store the angle information or the body marks.

The input interface 52 is realized by components for an operator to input various instructions, commands, information sets, selections, settings, etc., to its own information processing apparatus and such components include a trackball, switch buttons, a mouse, a keyboard, a touch pad which allows input operations through contacting of the operation screen, and a touch panel display which integrates a display screen and a touch pad. The input interface 52 is connected to the processing circuitry 55 and adapted to convert input operations received from the operator into electric signals and to output the electric signals to the processing circuitry 55. In the disclosure herein, the input interface 52 is not limited to physical operating components such as a mouse and a keyboard. That is, the examples of the input interface 52 also include processing circuitry for electric signals that is adapted to receive an electric signal corresponding to an input operation from an external input device separate from the apparatus, and to output this electric signal to the processing circuitry 55.

The display 53 includes a display main part for displaying medical images, etc., internal circuitry for supplying signals for display to the display main part, and peripheral circuitry including connectors, cables, or the like for connection between the display main part and the internal circuitry. The display 53 is capable of displaying the first mammograms stored in the storage 51, schematic diagrams generated by the processing circuitry 55, predetermined ranges obtained by computing operations, and so on.

The network interface 54 is circuitry for connecting the information processing apparatus 50 to the network Nw for communications with other apparatuses. As the network interface 54, for example, a network interface card (NIC) may be adopted. In the following disclosure, such a description as the network interface 54 being involved in the communications between the information processing apparatus 50 and other apparatuses will be omitted.

The processing circuitry 55 is adapted to read the control program from the storage 51 according to an operator's instruction input via the input interface 52, and to control the information processing apparatus 50 based on the read information. For example, the processing circuitry 55 is a processor to realize various functions according to the control program read from the storage 51. Such various functions include, for example, an acquisition function 55*a*, a UL-CAD function 55*b*, a specifying function 55*d*, an MG2 generation function 55*e*, a transmit/receive function 55*f*, etc. The MG2 generation function 55*e* is an optional feature and may be omitted.

Figure 6:
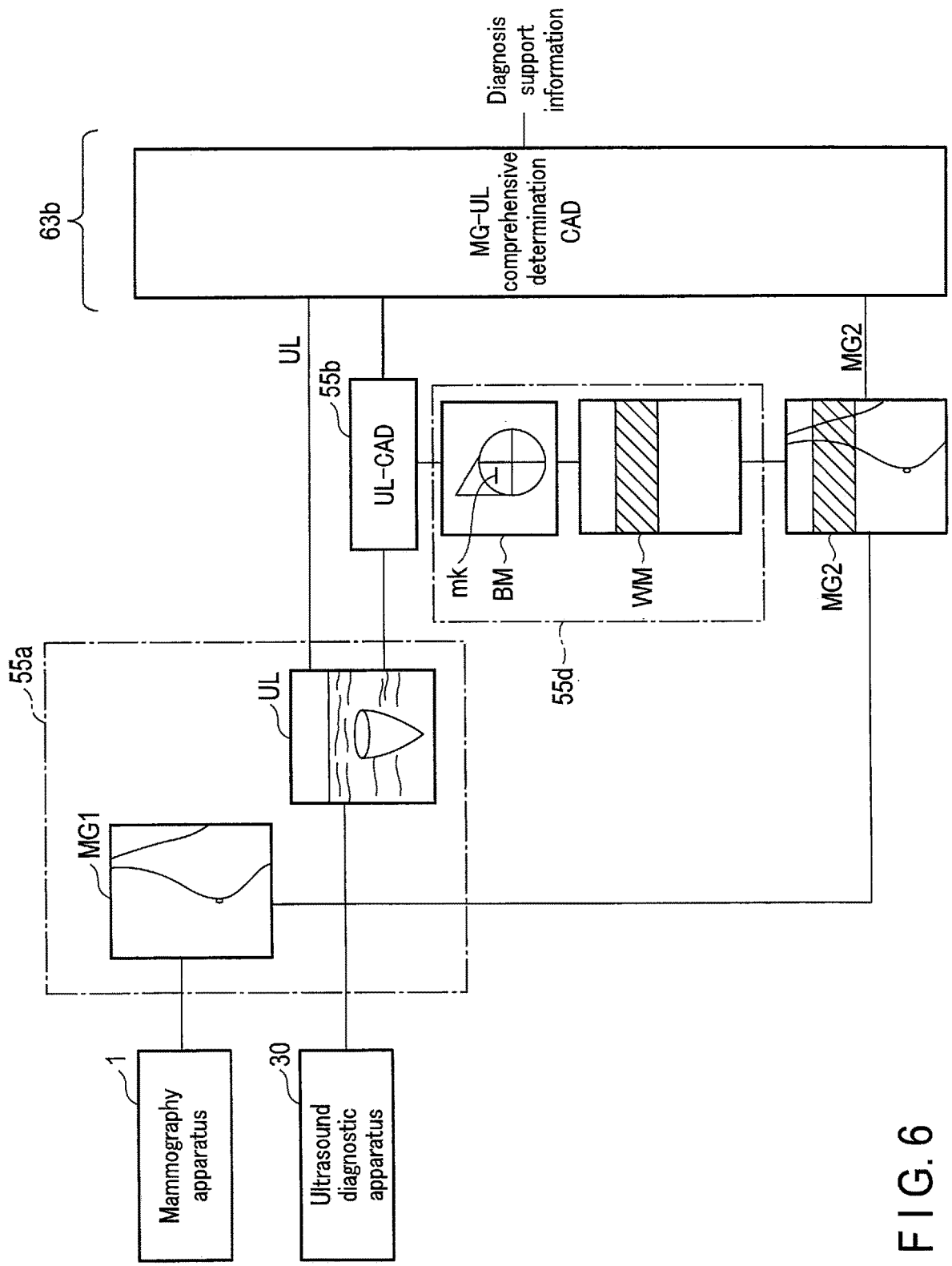
FIG. 6 is a schematic diagram showing a process according to the first embodiment, from acquisition of a first mammogram and an ultrasound image up to generation of diagnosis support information.

The acquisition function 55*a* includes, as shown in FIG. 6, a first acquisition function for acquiring an ultrasound image UL of a subject and a second acquisition function for acquiring a first mammogram MG1 of the same subject. Note that the first acquisition function also acquires the imaging position information for the ultrasound image UL (position information of the ultrasound probe 31), together with the ultrasound image UL. The acquisition function 55*a* is one example of a first acquirer and an imaging position acquirer.

The UL-CAD function 55*b* subjects the ultrasound image UL acquired by the acquisition function 55*a* to ultrasound-intended CAD (UL-CAD) processing. Here, "CAD" stands for computer-aided detection. The "computer-aided detection" may be called "computer-aided detection processing". By the term "UL-CAD", CAD with an ultrasound image is meant. The UL-CAD of this type may employ, for example, artificial intelligence (AI). Concrete examples that may be employed include a trained model adapted to generate a UL-CAD result using an ultrasound image UL as an input. The UL-CAD result may be information indicative of a state from a diseased state to a non-diseased state in multiple stages, for example, in five stages from category 5 (diseased) to category 1 (non-diseased). Note that having five stages is one example, and the number of stages may be greater or less than five. Still, at least two stages are required, e.g., category 2 (diseased) and category 1 (non-diseased). In response to the UL-CAD result indicating a diseased state, the UL-CAD function 55*b* stores the ultrasound image UL in the storage 51 and activates the specifying function 55*d*.

Figure 7:
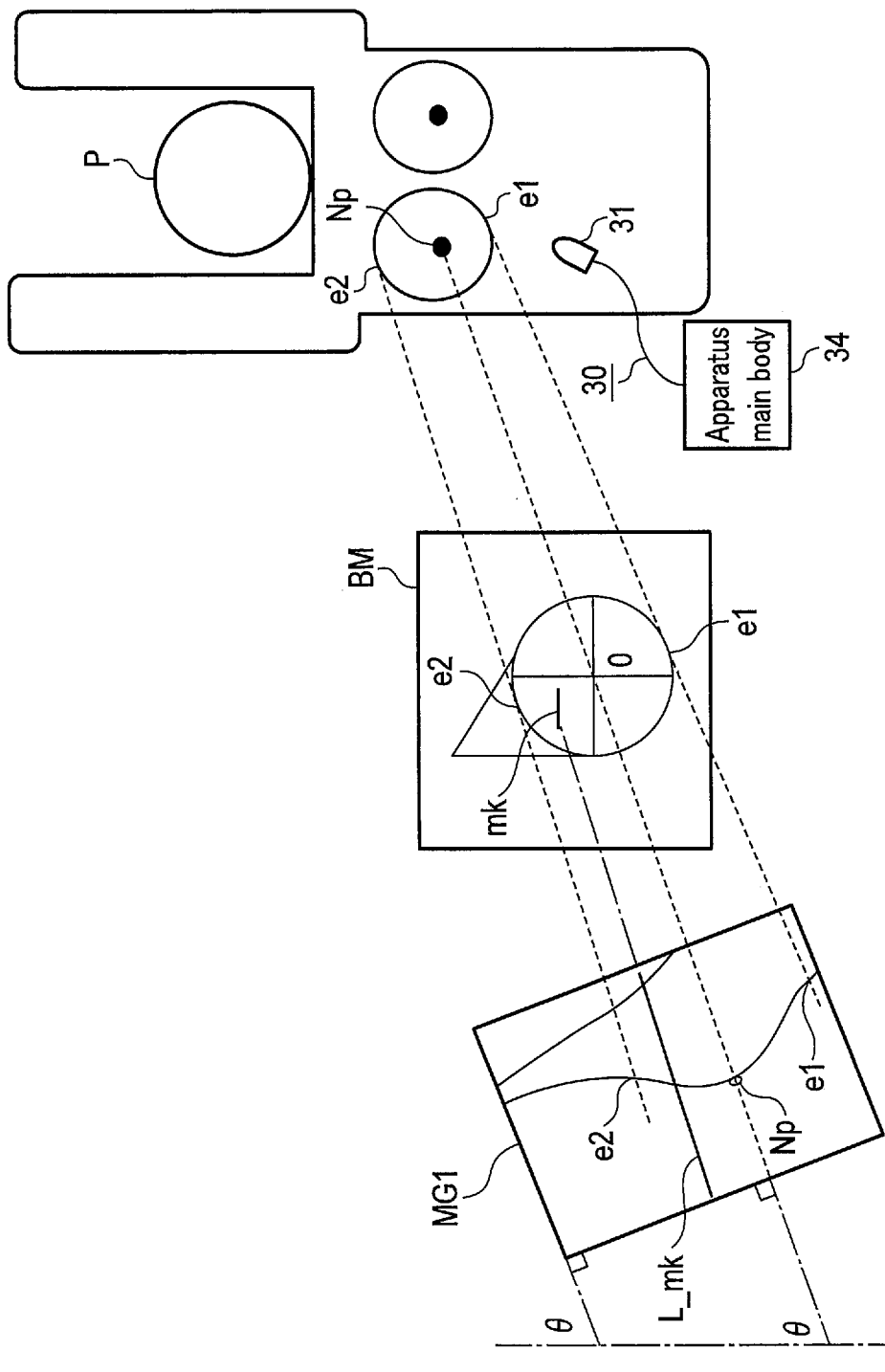
FIG. 7 is a schematic diagram for explaining corresponding positions on a subject's breast, a body mark, and a first mammogram in the context of the first embodiment.

The specifying function 55*d*, when the UL-CAD result indicates a diseased state, specifies on the first mammogram MG1 a position corresponding to the imaging position for the ultrasound image UL. In other words, based on the imaging position information for the ultrasound image UL, the specifying function 55*d* specifies the corresponding position on the first mammogram MG1. For example, the specifying function 55*d* may plot a mark that indicates the imaging position for the ultrasound image UL on the schematic diagram (body mark) of the subject's breast, and then specify a region of interest corresponding to the position of the plotted mark on the first mammogram (first modality image). More specifically, the specifying function 55*d* may plot a mark mk indicative of the imaging position for the ultrasound image UL on the body mark BM of the breast as shown in FIG. 7. The specifying function 55*d* may also specify, on the first mammogram MG1, a region of interest of a band-shaped range having its center coincide with a straight line L_mk corresponding to the position of the mark mk. The specifying function 55*d* is one example of a specifier for specifying, based on the imaging position information for an ultrasound image, a position on the first modality image that corresponds to the imaging position.

In addition to the above, at the start of ultrasound inspection, the specifying function 55*d* preliminarily acquires the imaging position information (position information of the ultrasound probe 31) for the ultrasound image UL that corresponds to the position of the nipple Np of the subject P and associates this position of the nipple Np with the coordinate origin O on the body mark BM, as shown in FIG. 7. The specifying function 55*d*, at the start of ultrasound inspection, may also preliminarily acquire the sets of imaging position information for the ultrasound image UL that correspond to the positions of respective ends e1 and e2 of the subject P's breast, and associate these positions of the breast ends e1 and e2 with the positions on the body mark BM that correspond to the ends e1 and e2. Note that the origin O is an origin of a Z—Y coordinate where the vertical axis on the body mark BM is taken as the axis Z and the horizontal axis is taken as the axis Y, and the origin O indicates the position of the nipple Np on the body mark BM. The positions on the body mark BM that correspond to the respective ends e1 and e2 are located on a circumference having the center at the origin O, while corresponding to the positions of the subject P's breast ends e1 and e2 and also to the breast ends e1 and e2 in the first mammogram MG1. FIG. 7 shows the first mammogram MG1 inclined at an MLO imaging angle θ. That is, the exemplary straight line L_mk shown in FIG. 7 is a straight line that follows the imaging angle θ for the first mammogram MG1, corresponds to the mark mk's position dividing the segment from the origin O to the end e2 on the body mark BM, and is located at the position dividing the segment from the nipple Np to the end e2 in the first mammogram MG1. For example, supposing that the mark mk is given at the position on the body mark BM that divides the segment from the origin O to the end e2 at a ratio a:b, then the straight line L_mk is located at the position in the first mammogram MG1 that divides the segment from the nipple Np to the end e2 at the ratio a:b. As such, preliminarily associating the sets of imaging position information for the ultrasound image UL that correspond to the characteristic positions (Np, e1, and e2) in the breast with the respective characteristic positions (O, e1, and e2) on the body mark BM enables the plotting of the mark mk indicative of the imaging position information for the ultrasound image UL on the body mark BM.

Also, the positions corresponding to the origin O and the breast ends on the body mark BM and the positions corresponding to the nipple Np and the ends e1 and e2 in the first mammogram MG1 have the relationship as shown in, for example, FIG. 7. Note that, in an exemplary implementation, the positions of the nipple Np and the ends e1 and e2 in the first mammogram MG1 may each be approximated as a contour point near the intersection of adjacent straight lines of multiple straight lines which together approximate the contour of the breast in the first mammogram MG1. In another exemplary implementation, the positions of the nipple Np and the ends e1 and e2 in the first mammogram MG1 may be detected using other image detection technique generally known to the public.

In any case, the positions on the body mark BM correspond to the positions on the first mammogram MG1. As such, the position of the mark mk on the body mark BM can be associated as the position of the straight line L_mk given according to the imaging angle θ in the first mammogram MG1. Also, a region of interest of a band-shaped range may be specified on the first mammogram MG1 by employing the straight line L_mk corresponding to the position of the mark mk as the center of the band-shaped range. The size (width) of the band-shaped range is discretionary. Moreover, the specifying function 55d may create locating information indicative of the region of interest thus specified. The locating information here is one example of information representing the imaging position for an ultrasound image UL. Also, the information representing the imaging position for the ultrasound image UL is one example of information that can be acquired based on the imaging position for the ultrasound image UL.

Examples that may be employed as the locating information include a weight map WM for putting a greater weight on the region of interest, trimming information for taking out the region of interest, an image (partial image) of the region of interest taken out from the first mammogram MG1, etc. The weight map WM is, for example, a mask image having the same size and the same number of pixels as the first mammogram MG1, and in which the region of interest shown as a shaded area in FIG. 6 has a pixel value different from that of the other regions. In concrete implementation, the region of interest has a high pixel value of "1" and the other regions have a pixel value of "0.1", lower than the pixel value of the region of interest. Note that use of such pixel values are only an example, and other values may be used. In other exemplary implementations, the other regions may have a pixel value "0", while the region of interest has a pixel value "1". The trimming information is numerical information indicative of a range of the region of interest on the first mammogram MG1 and, for example, a numerical value such as a coordinate, size or the like may be adopted as appropriate. The partial image is an image of the region of interest taken out from the first mammogram MG1 and has the same size and the same number of pixels as the region of interest. The following description will assume instances where the locating information is the weight map WM.

The specifying function 55d stores the body mark BM with the plotted mark mk in the storage 51, in association with the ultrasound image UL that has been stored by the UL-CAD function 55b.

The MG2 generation function 55e generates a second mammogram MG2 by, for example, processing the first mammogram MG1 based on the position specified by the specifying function 55d. More specifically, and for example, the second mammogram MG2 in which the region of interest from the first mammogram MG1 is emphasized is generated by multiplying each pixel value of the first mammogram MG1 by the respective pixel value of the weight map WM as the locating information. This second mammogram MG2 may be called an "MG*weight map". The MG2 generation function 55e may generate the second mammogram MG instead by performing trimming to take out the region of interest in the first mammogram MG1 based on the trimming information as the locating information. This second mammogram MG2 generated through the trimming corresponds to the aforementioned partial image. The MG2 generation function 55e is one example of an image generator for generating a second modality image by subjecting the first modality image to the process based on the imaging position for the ultrasound image.

The transmit/receive function 55f is a function for performing transmission and reception with other apparatuses. The transmit/receive function 55f transmits first input data or second input data. The first input data contains the ultrasound image UL, and the second mammogram MG2 which has been obtained by subjecting the first mammogram to the process (by the MG2 generation function 55e) based on the specified position (specified by the specifying function 55d). The second input data contains the ultrasound image UL, the first mammogram MG1, and information for a corresponding position. Note that the particulars of the latter, i.e., the second input data, will be described with reference to a modification of the first embodiment, etc., and the description of the first embodiment will assume instances of transmitting the former, i.e., the first input data. The first input data is one example of first data. The second input data is one example of second data. The transmit/receive function 55f is one example of a first transmitter for transmitting the ultrasound image, the imaging position for this ultrasound image, and the first modality image.

In one example, the transmit/receive function 55f transmits the first input data containing the second mammogram MG2 generated by the MG2 generation function 55e and the ultrasound image UL stored in the storage 51 to the server apparatus 60 in the server system Svs1. The first input data is for use by a generation function 63b in the server apparatus 60 which is a transmission destination, for generating diagnosis support information using an MG-UL comprehensive determination CAD. In an example, also, the transmit/receive function 55f receives the diagnosis support information from the server apparatus 60. The MG-UL comprehensive determination CAD may be simply called "comprehensive determination CAD".

Figure 8:
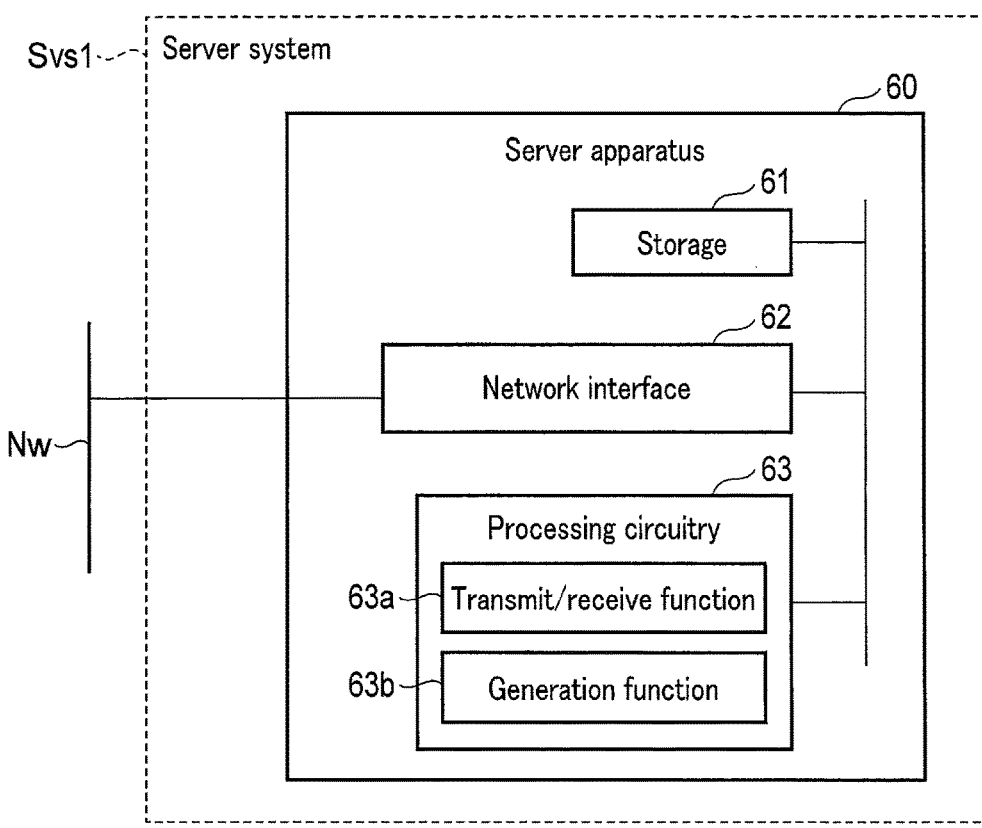
FIG. 8 is a block diagram showing a configuration of a server apparatus in a server system according to the first embodiment.
Figure 9:
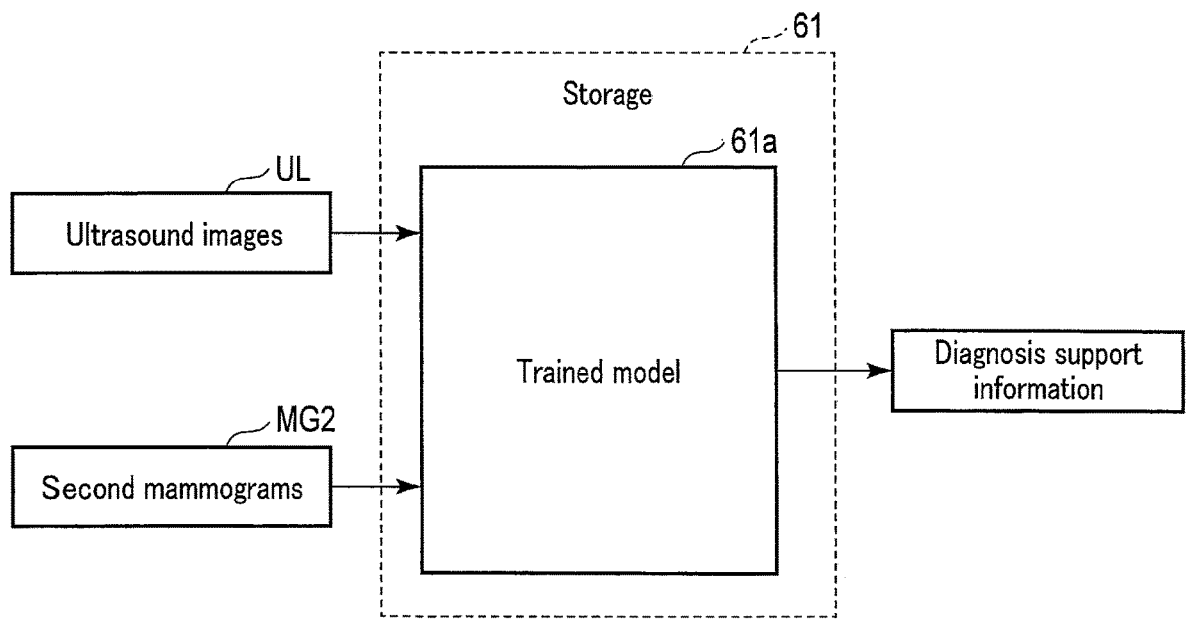
FIG. 9 is a schematic diagram for explaining a trained model according to the first embodiment.

Turning to the server system Svs1, it is adapted to generate, upon receipt of the first input data or the second input data from the client system Cls1, the diagnosis support information for the subject using the received first input data or second input data as an input and transmit the diagnosis support information. For example, upon receipt of an ultrasound image, the imaging position for the ultrasound image, and the first modality image from the client system Cls1, the server system Svs1 generates the diagnosis support information for the subject based on the received ultrasound image, imaging position for the ultrasound image, and first modality image, and transmits the diagnosis support information. As a concrete configuration, the server apparatus 60 in the server system Svs1 includes storage 61, a network interface 62, and processing circuitry 63, as shown in FIGS. 8 to 10.

The storage 61 here is constituted by a memory for storing electric information, such as a read only memory (ROM), a random access memory (RAM), a hard disk drive (HDD), an image memory, etc. The storage 61 is also constituted by peripheral circuitry pertaining to the memory, such as a memory controller, a memory interface, etc. The storage 61 is adapted to store various data sets such as control programs for its own server apparatus, a trained model 61a, a model training program, the first input data, and so on. The first input data includes, for example, the second mammogram MG2 and the ultrasound image UL, and may further include the UL-CAD result. The trained model 61a has been trained using second mammograms MG2, ultrasound images UL, and diagnosis support information sets indicating a state from a diseased state to a non-diseased state in multiple stages, as shown in FIG. 9. The trained model 61a and the generation function 63b in this case constitute one example of a generation processor for generating the diagnosis support information for the subject based on an input second modality image MD2 and ultrasound image UL. The trained model 61a may instead be a model that has been trained using second mammograms MG2, ultrasound images UL, UL-CAD results, and diagnosis support information sets indicating a state from a diseased state to a non-diseased state in multiple stages, as shown in FIG. 10. Note that the diagnosis support information sets for the training process may be prepared by interpreting doctors.

The trained model 61a here is a trained machine learning model that has been obtained by subjecting a machine learning model to a machine learning process using training data based on the model training program. The training data includes input data such as second mammograms MG2 and ultrasound images UL, and output data which is diagnosis support information. The training data may also include UL-CAD results as the input data, in addition to the second mammograms MG2 and the ultrasound images UL. The machine learning model is a composite function with parameters in which multiple functions are combined, and it is adapted to output the diagnosis support information using the second mammogram MG2 and the ultrasound image UL as inputs. Such a parameter-added composite function is defined by the combination of multiple adjustable functions and parameters. While the machine learning model according to this embodiment may be any parameter-added composite function as long as the above role is served, the description will assume that the machine learning model here is a multi-layered network model (hereinafter, "multilayer network"). The trained model 61a in this case includes an input layer for inputting a second mammogram MG2 and an ultrasound image UL, an output layer for outputting the diagnosis support information based on the result of comprehensively interpreting the second mammogram MG2 and the ultrasound image UL, and at least one intermediate layer arranged between the input layer and the output layer. The input layer may receive, in addition to the multiple sets of medical image data, inputs of related information such as accessory information and a CAD result for each piece of medical image data, etc. This trained model 61a is expected to be utilized as a program module constituting part of artificial intelligence software. The trained model 61a is for use by the processing circuitry 63. More specifically, the processing circuitry 63 follows the instructions from the trained model 61a stored in the storage 61 to perform, based on trained parameters, arithmetic operations on the first input data or the second input data that has been input to the input layer, so that the diagnosis support information will be output from the output layer. Description will be given of a typical configuration of the multilayer network according to the embodiment. The multilayer network here has a structure in which only adjacent layers are coupled to each other, and information propagates in one direction from the input layer side to the output layer side. It will be assumed that the multilayer network according to the embodiment is constituted by L layers, namely, an input layer (l=1), intermediate layers (l=2, 3, ..., L−1), and an output layer (l=L), as shown in FIG. 11. The following description is based on examples and not intended to limit the configuration of the multilayer network.

Supposing that there are I units in the l-th layer, and that Equation (1-1) represents an input $u^{(l)}$ to the l-th layer and Equation (1-2) represents an output $z^{(l)}$ from the l-th layer, the relationship between the input to the l-th layer and the output from the l-th layer can be expressed by Equation (1-3).

$$u^{(l)}=(u_1,u_2,u_3,\ldots,u_I) \qquad (1\text{-}1)$$

$$z^{(l)}=(z_1,z_2,z_3,\ldots,z_I) \qquad (1\text{-}2)$$

$$z^{(l)}=f(u^{(l)}) \qquad (1\text{-}3)$$

The upper right superscript "(l)" indicates the layer number. Also, f(u) in Equation (1-3) is an activation function, for which any of various functions including a logistic sigmoid function (logistic function), a hyperbolic tangent function, a normalized linear function (or ReLU), a linear mapping, an identity mapping, a max-out function, etc. may be selected according to the purposes. The term "ReLU" is an abbreviation of "rectified linear unit".

It will be supposed that there are J units in the (l+1)-th layer, and that Equation (2-1) represents a weighting matrix $W^{(l+1)}$ between the l-th layer and the l+1 layer and Equation (2-2) represents a bias $b^{(l+1)}$ in the (l+1)-th layer. Then, an input $u^{(l+1)}$ to the (l+1)-th layer and an output $z^{(l+1)}$ from the (l+1)-th layer may be expressed by Equations (2-3) and (2-4), respectively.

$$W^{(l+1)} = \begin{pmatrix} w_{11} & \cdots & w_{1J} \\ \vdots & \ddots & \vdots \\ w_{J1} & \cdots & w_{JJ} \end{pmatrix} \qquad (2\text{-}1)$$

$$b^{(l+1)} = (b_1, b_2, b_3, \ldots \ldots, b_l) \qquad (2\text{-}2)$$

$$u^{(l+1)} = w^{(l+1)} z^{(l)} + b^{(l+1)} \qquad (2\text{-}3)$$

$$z^{(l+1)} = f(u^{(l+1)}) \qquad (2\text{-}4)$$

In the multilayer network according to the embodiment, medical image data (and related information such as a CAD result) expressed by Equation (3-1) is input to the input layer (l=1). In this input layer, the input data x directly becomes output data $z^{(l)}$, and therefore, the relationship of Equation (3-2) holds.

$$x=(x_1,x_2,\ldots,x_N) \qquad (3\text{-}1)$$

$$z^{(l)}=x \qquad (3\text{-}2)$$

The medical image data (with the related information) to be input to the input layer will be called "input data x". The input data x may adopt a variety of forms such as form (1) or form (2) below.

Form (1) in which the input data x includes multiple image datasets (with related information) and each component $x_p$ (p=1, 2, ..., N) is defined as a value (and a value for the related information), i.e., a pixel value or a voxel value, of the respective position in the multiple image datasets (with the related information).

Form (2) which follows the form (1) and in which the input data x is image data (with related information) that has been subjected to a convolutional process.

For the intermediate layers (l=2, 3, ..., L−1) subsequent to the input layer, outputs $z^{(2)}, \ldots z^{(L-1)}$ of the respective layers can be calculated by sequentially performing the calculations according to Equations (2-3) and (2-4).

An output z(W) of the output layer (L-th layer) will be expressed as Equation (4-1) below. The multilayer network according to the embodiment is a forward propagation network which lets the image data x input to the input layer propagate from the input layer side to the output layer side while bridging only between the adjacent layers. Such a forward propagation network can be expressed by a composite function as Equation (4-2).

$$z^{(L)}:y = z^{(L)} \qquad (4\text{-}1)$$

$$\begin{aligned}
y(x) &= f(u^{(L)}) \qquad (4\text{-}2)\\
&= f(w^{(L)} z^{(L-1)} | b^{(L)})\\
&= f(w^{(L)} f(w^{(L-1)} z^{(L-2)} + b^{(L-1)}) + b^{(L)})\\
&= f(w^{(L)} f(w^{(L-1)} f(\ldots \ldots f(w^{(L)} z^{(l-1)} + b^{(l)}) \ldots \ldots)) + b^{(L)})
\end{aligned}$$

The composite function expressed as Equation (4-2) may be defined as, from Equations (2-3) and (2-4), a combination of an inter-layer linear relationship that uses a weighting matrix $W^{(l+1)}$, a nonlinear relationship (or linear relationship) that uses an activation function $f(u^{(l+1)})$ of the respective layer, and a bias $b^{(l+1)}$. In particular, the weighting matrix $W^{(l+1)}$ and the bias $b^{(l+1)}$ are called a network parameter p. The composite function defined by Equation (4-2) changes its form as a function, depending on how the parameter p is selected. Thus, selecting a suitable parameter p for constituting Equation (4-2) allows the multilayer network according to the embodiment to be defined as a function with the output layer capable of outputting a desirable result y.

To select the suitable parameter p, a training process is carried out using training data and an error function. Here, the training data is a set D (n=1, ..., S) of training samples $(x_n, d_n)$ expressed as Equation (5-1), where $d_n$ is a desired output (ground truth output) for the input $x_n$.

$$(x_n, d_n) \qquad (5\text{-}1)$$

$$D=\{(x_1,d_1),\ldots,(x_s,d_s)\} \qquad (5\text{-}2)$$

Also, the error function is a function representing the proximity of the output, which is given from the multilayer network that was input with the data $x_n$, to the training data $d_n$. Typical examples of the error function include a squared error function, a maximum likelihood estimation function, a cross entropy function, etc. Which function should be used as the error function depends on the problem handled by the multilayer network (e.g., a regression problem, a binary problem, a multi-class classification problem, etc.).

The error function will be expressed as E(p), and the error function calculated using only a single training sample $(x_n, d_n)$ will be expressed as $E_n(p)$. The present parameter $p^{(t)}$ is updated to a new parameter $p^{(t+1)}$ by Equation (6-1) that uses the gradient vector of the error function E(p) in the case of adopting the gradient descent method, and updated by Equation (6-3) that uses the gradient vector of the error function $E_n(p)$ in the case of adopting the stochastic gradient descent method.

$$p^{(t+1)} = p^{(t)} - \varepsilon \nabla E(p^{(t)}) \qquad (6\text{-}1)$$

$$\nabla E(p^{(t)}) \equiv \frac{\partial E}{\partial p^{(t)}} = \left[\frac{\partial E}{\partial p_1^{(t)}}, \ldots \ldots \frac{\partial E}{\partial p_M^{(t)}}\right] \qquad (6\text{-}2)$$

$$p^{(t+1)} = p^{(t)} - \varepsilon \nabla E_n(p^{(t)}) \qquad (6\text{-}3)$$

$$\nabla E_{n(p^{(t)})} \equiv \frac{\partial E_n}{\partial p^{(t)}} = \left[\frac{\partial E_n}{\partial p_1^{(t)}}, \ldots \ldots \frac{\partial E_n}{\partial p_M^{(t)}}\right] \qquad (6\text{-}4)$$

Here, ε is a training coefficient for setting a size of the update amount of the parameter p.

The present p is slightly moved in the negative gradient direction according to Equation (6-1) or (6-3), and sequentially repeating this will enable determining the parameter p that minimizes the error function E(p).

Note that, to proceed with the calculations of Equation (6-1) or (6-3), calculating the gradient vector of E(p) expressed by Equation (6-2) or calculating the gradient vector of $E_n(p)$ expressed by Equation (6-4) is necessary. For example, if the error function is a squared error function, the error function expressed by Equation (7-1) needs to be differentiated with respect to the weighting factor of the respective layer and the bias of each unit.

$$E(\vec{p}) = \frac{1}{2}\sum_{n=1}^{N}\|d_n - y(x_n:p)\|^2 \qquad (7\text{-}1)$$

However, as the final output y is the composite function expressed by Equation (4-2), the calculation of the gradient vector of E(p) or $E_n(p)$ is complicated and requires a very large calculation amount.

Such a problem in gradient calculation can be solved by the error back-propagation method. For example, a derivative of the error function for the weight $w_{ji}^{(l)}$ connecting the i-th unit of the (l−1)-th layer and the j-th unit of the l-th layer can be expressed as Equation (8-1) below.

$$\frac{\partial E_n}{\partial w_{ji}^{(l)}} = \frac{\partial E_n}{\partial u_j^{(l)}}\frac{\partial u_j^{(l)}}{\partial w_{ji}^{(l)}} \qquad (8\text{-}1)$$

An amount of change to $E_n$, which is due to an input $u_j^{(l)}$ to the j-th unit of the l-th layer, will be produced only as a result of the output $z_j^{(l)}$ from this j-th unit changing the input $u_k^{(l+1)}$ to each unit k of the (l+1)-th layer. Thus, the first term on the right side of Equation (8-1) can be given as Equation (9-1) below, using the chain rule of differentiation.

$$\frac{\partial E_n}{\partial u_j^{(l)}} = \sum_k \frac{\partial E_n}{\partial u_k^{(l+1)}}\frac{\partial u_k^{(l+1)}}{\partial u_j^{(l)}} \qquad (9\text{-}1)$$

Here, if the left-hand side of Equation (9-1) is substituted with $\delta_j^{(l)}$, then Equation (9-1) can be rewritten as Equation (10-3) based on the relations given by Equations (10-1) and (10-2).

$$u_k^{(l+1)} = \sum_j w_{kj}^{(l+1)} z_j^{(l)} = \sum_i w_{kji}^{(l+1)} f(u_j^{(l)}) \qquad (10\text{-}1)$$

$$\frac{\partial u_k^{(l+1)}}{\partial u_j^{(l)}} = w_{kj}^{(l+1)}\frac{\partial f(u_j^{(l)})}{\partial u_j^{(l)}} \qquad (10\text{-}2)$$

$$\delta_j^{(l)} = \sum_k \delta_k^{(l+1)}\left(w_{kj}^{(l+1)}\frac{\partial f(u_j^{(l)})}{\partial u_j^{(l)}}\right) \qquad (10\text{-}3)$$

It is understood from Equation (10-3) that $\delta_j^{(l)}$ on the left-hand side can be calculated from $\delta_k^{(l+1)}$ (k=1, 2, ... ). That is, $\delta_j^{(l)}$ for the l-th layer can be calculated once $\delta_k^{(l+1)}$, which is for the k-th unit of the (l+1)-th layer as one layer higher on the output layer side than the l-th layer, is given.

Moreover, $\delta_k^{(l+1)}$ for the k-th unit of the (l+1)-th layer can also be calculated once $\delta_k^{(l+2)}$, which is for the k-th unit of the (l+2)-th layer as one layer higher on the output layer side than the (l+1)-th layer, is given.

Sequentially repeating this enables tracking up to the output layer as the highest layer.

If $\delta_k^{(L)}$ for the k-th unit of the output layer as the L-th layer is already acquired at the start, $\delta_k^{(l+1)}$ for any layer can be calculated by repeating the calculation using Equation (10-3) sequentially toward the lower side (i.e., toward the input layer side)(back propagation).

Meanwhile, the second term on the right side of Equation (8-1) can be calculated as in Equation (11-2), using Equation (11-1) in which Equation (2-3) is expressed in component terms for the l-th layer.

$$u_j^{(l)} = \sum_i w_{ji}^{(l)} z_i^{(l-1)} \qquad (11\text{-}1)$$

$$\frac{\partial u_j^{(l)}}{\partial w_{ji}^{(l)}} = z_i^{(l-1)} \qquad (11\text{-}2)$$

Thus, the derivative of the error function for the weight $w_{ji(l)}$ connecting the i-th unit of the (l−1)-th layer and the j-th unit of the l-th layer can be expressed as Equation (12-1) below, using Equation (8-1), $\delta_j^{(l)}$ given by Equation (10-3), and Equation (11-2).

$$\frac{\partial E_n}{\partial w_{ji}^{(l)}} = \delta_j^{(l)} z_i^{(l-1)} \qquad (12\text{-}1)$$

It is understood from Equation (12-1) that the derivative of the error function for the weight $w_{ji}^{(l)}$ connecting the i-th unit of the (l−1)-th layer and the j-th unit of the l-th layer is given by the product of $\delta_j^{(l)}$ for the j-th unit and the output $z_i^{(l-1)}$ from the i-th unit. The calculation for $\delta_j^{(l)}$ can be executed by back propagation using Equation (10-3) as described above, and the initial value of the back propagation, that is, $\delta_j^{(L)}$ for the output layer as the L-th layer, can be calculated as in Equation (13-1) below.

$$\delta_j^{(L)} = \frac{\partial E_n}{\partial u_j^{(L)}} \qquad (13\text{-}1)$$

With the above procedure, the training process using a given training sample $(x_n, d_n)$ for the multilayer network according to the embodiment can be realized. Note that the gradient vector for the total sum $E = \Sigma_n E_n$ of errors for multiple training samples can be acquired by repeating the above procedure for the training samples $(x_n, d_n)$ in a parallel manner and calculating the sum according to Equation (14-1) below.

$$\frac{\partial E}{\partial w_{ji}^{(l)}} = \sum_n \frac{\partial E_n}{\partial w_{ji}^{(l)}} \qquad (14\text{-}1)$$

The multilayer network according to the embodiment has been described. As the multilayer network according to the embodiment, for example, a deep neural network (DNN) which is a multilayer neural network intended for deep learning is employed. As the DNN, for example, a convolutional neural network (CNN) intended for images may be used. The foregoing description of the multilayer network will likewise apply to all of the subsequent embodiments that utilize machine learning models and the trained model 61a.

The network interface 62 is circuitry for connecting the server apparatus 60 to the network Nw for communications with other apparatuses. As the network interface 62, for example, a network interface card (NIC) may be adopted. In the following disclosure, such descriptions as the network interface 62 being involved in the communications between the server apparatus 60 and other apparatuses will be omitted.

The processing circuitry 63 is adapted to control the server apparatus 60 according to the control program stored in the storage 61. For example, the processing circuitry 63 is a processor to realize various functions according to the control program read from the storage 61. Such various functions include, for example, a transmit/receive function 63a and the generation function 63b.

The transmit/receive function 63a is a function for performing transmission and reception with other apparatuses, and it receives, for example, the first input data containing the second mammogram MG2 and the ultrasound image UL from the information processing apparatus 50. Note that when the transmitted object from the information processing apparatus 50 is the second input data, the transmit/receive function 63a receives this second input data. In an example, also, the transmit/receive function 63a transmits the diagnosis support information generated by the generation function 63b. The transmit/receive function 63a is one example of a receiver for receiving the ultrasound image, the imaging position for this ultrasound image, and the first modality image, as well as one example of a second transmitter for transmitting the diagnosis support information.

The generation function 63b generates the diagnosis support information for the subject using an input, i.e., the first input data received by the transmit/receive function 63a. When the second input data is received by the transmit/receive function 63a, the generation function 63b generates the diagnosis support information for the subject using the second input data as an input. The diagnosis support information is indicative of a state from a diseased state to a non-diseased state in multiple stages, for example, in five stages from category 5 (diseased) to category 1 (non-diseased). Note that having five steps is one example, and the number of stages may be greater or less than five. Still, at least two stages are required, e.g., category 2 (diseased) and category 1 (non-diseased). The generation function 63b is one example of a generator for generating the diagnosis support information for the subject based on the ultrasound image, the imaging position for this ultrasound image, and the first modality image (which have been received). The generation function 63b is also one example of a generator that includes a generation processor for generating the diagnosis support information for the subject based on the ultrasound image, the imaging position for this ultrasound image, and the first modality image.

The generation function 63b, for example, uses the trained model 61a to acquire the diagnosis support information from the first input data. More specifically, the generation function 63b follows the instructions from the trained model 61a stored in the storage 61 to perform, based on trained parameters, arithmetic operations on the first input data input to the input layer of the trained model 61a so that the diagnosis support information is output from the output layer of the trained model 61*a*. The generation function 63*b* as such enables an operation proceeding as the CAD operation for comprehensively making a determination as to multiple stages from a diseased state to a non-diseased state based on the second mammogram MG2 and the ultrasound image UL, and therefore, the generation function 63*b* may be called "MG-UL comprehensive determination CAD" as indicated by FIG. 6.

Figure 12:
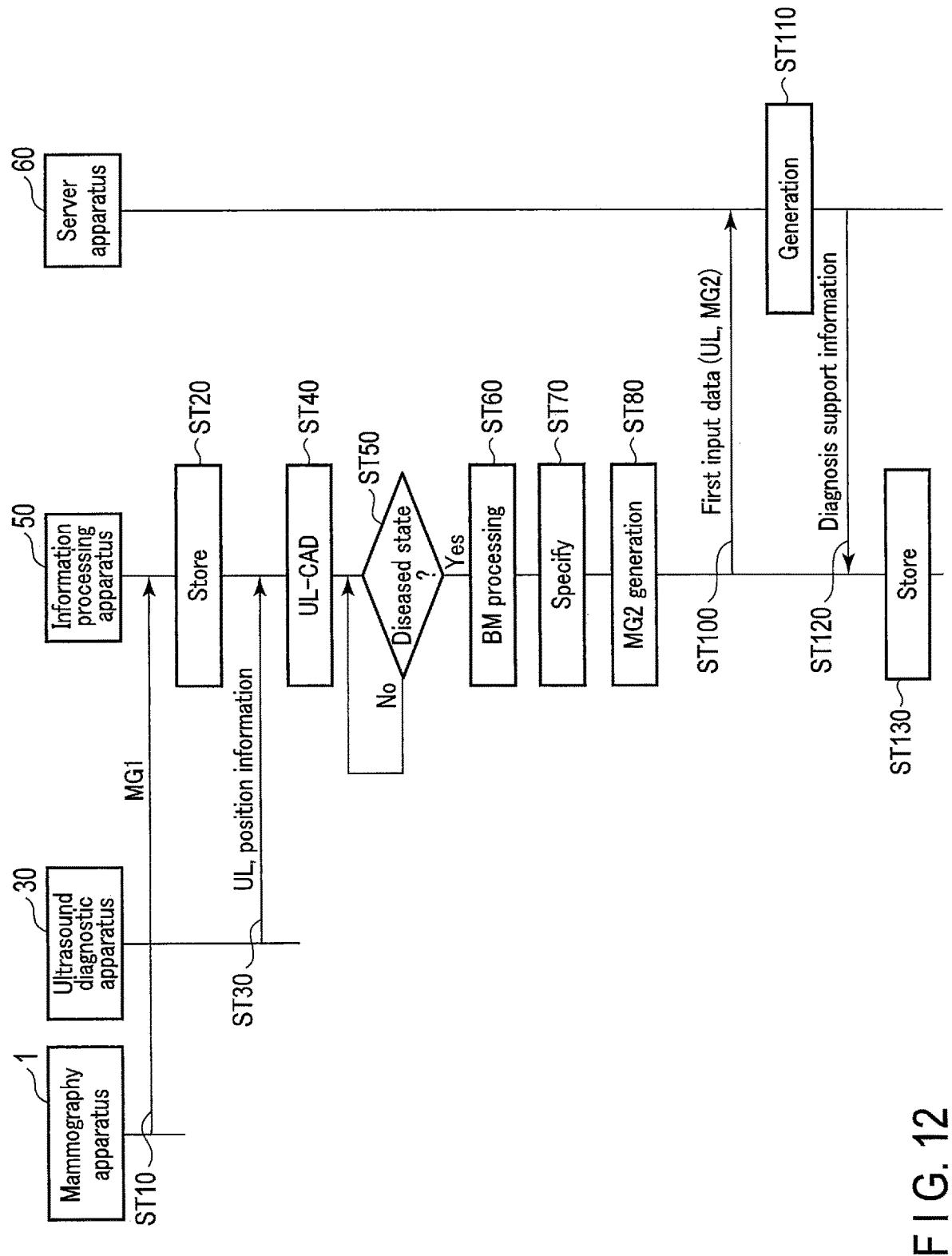
FIG. 12 is a sequence diagram for explaining operations according to the first embodiment.

Next, how the medical information processing system configured as above operates will be described with reference to FIG. 12.

Suppose the present state in which the storage 22 of the mammography apparatus 1 stores a first mammogram MG1 acquired by imaging the subject's breast and angle information indicative of the imaging angle for the first mammogram MG1.

Then, in step ST10, the processing circuitry 26 of the mammography apparatus 1 transmits the first mammogram MG1 to the information processing apparatus 50 in response to a request from the information processing apparatus 50.

In step ST20 after step ST10, the processing circuitry 55 of the information processing apparatus 50, upon acquisition of the first mammogram MG1 of the subject, stores this first mammogram MG1 in the storage 51.

In step ST30 after step ST20, the ultrasound diagnostic apparatus 30 scans the subject's breast using the ultrasound probe 31 according to the operator's operation, and transmits the generated ultrasound image and the imaging position information for the ultrasound image to the information processing apparatus 50.

In step ST40 after step ST30, the processing circuitry 55 of the information processing apparatus 50 acquires the ultrasound image of the subject and the imaging position information for the ultrasound image, and performs UL-CAD processing with the ultrasound image to generate a UL-CAD result.

In step ST50 after step ST40, the processing circuitry 55 determines whether or not the UL-CAD result indicates a diseased state, and if it does not indicate a diseased state, repeats this determining action until the end of the ultrasound inspection. If, on the other hand, the UL-CAD result indicates a diseased state, the processing circuitry 55 stores the applicable ultrasound image UL in the storage 51.

After step ST50, steps ST60 to ST70 are performed where the processing circuitry 55 refers to the imaging position information for the ultrasound image UL to specify a corresponding position on the first mammogram MG1. For example, in step ST60, the processing circuitry 55 plots a mark mk indicative of the imaging position for the ultrasound image UL on a body mark BM of the breast. The processing circuitry 55 also stores the body mark BM with the plotted mark mk in the storage 51, in association with the ultrasound image UL that has been stored.

In step ST70 after step ST60, the processing circuitry 55 specifies, on the first mammogram MG1, a region of interest of a band-shaped range having the center at the position of the mark mk, and generates a weight map WM for putting a greater weight on this region of interest.

In step ST80 after step ST70, the processing circuitry 55 generates a second mammogram MG2 by subjecting the first mammogram MG1 to the process based on the position specified in step ST70. In this example, each pixel value of the weight map WM and the respective pixel value of the first mammogram MG1 are multiplied so as to generate the second mammogram MG2 emphasizing the region of interest from the first mammogram MG1.

In step ST100 after step ST80, the processing circuitry 55 transmits the first input data containing the generated second mammogram MG2 and the ultrasound image UL that is stored in the storage 51 to the server apparatus 60.

In step ST110 after step ST100, the processing circuitry 63 of the server apparatus 60 generates, upon receipt of the first input data, diagnosis support information for the subject using the first input data as an input. In this example, the processing circuitry 63 acquires the diagnosis support information from the first input data using the trained model 61*a* stored in the storage 61. More specifically, the processing circuitry 63 follows the instructions from the trained model 61*a* to perform, based on trained parameters, arithmetic operations on the first input data input to the input layer of the trained model 61*a* so that the diagnosis support information is output from the output layer of the trained model 61*a*.

In step ST120 after step ST110, the processing circuitry 63 transmits the generated diagnosis support information to the information processing apparatus 50.

In step ST130 after step ST120, the processing circuitry 55 of the information processing apparatus 50 stores the diagnosis support information in the storage 51, upon receipt of the diagnosis support information. The processing circuitry 55 controls the display 53 to display the diagnosis support information, the first mammogram MG1, and the ultrasound image UL which are stored in the storage 51, according to an operation by the operator (interpreting doctor). In this manner, support for the interpreting doctor's diagnosing work is provided.

As described above, the first embodiment employs a medical information processing system including the client system with at least one information processing apparatus and the server system with at least one server apparatus. The client system acquires an ultrasound image of a subject, acquires a first mammogram of the subject, and specifies, based on the imaging position information for the ultrasound image, a corresponding position on the first mammogram. Also, the client system transmits first input data containing a second mammogram obtained by processing the first mammogram based on the corresponding position, and the ultrasound image. The server system receives the first input data, generates diagnosis support information for the subject using the received first input data as an input, and transmits the diagnosis support information.

With this configuration of transmitting the diagnosis support information generated using, as an input, the first input data containing the second mammogram and the ultrasound image, comprehensive interpretation of the mammogram and the ultrasound image is enabled, and support for the diagnosis can be provided. For example, the configuration allows for interpretation of a mammogram and an ultrasound image which are obtained by imaging the same lesion at the same location, so that the diagnosis can be assisted.

In addition, according to the first embodiment, CAD (MG-UL comprehensive determination CAD) can be performed with the spot in a mammogram that corresponds to the position in the breast rendered on an ultrasound image. Therefore, CAD can be performed with both the mammogram and the ultrasound image, for the same region in the breast.

Moreover, since the corresponding position is specified in response to the computer-aided detection with an ultrasound image resulting in an indication of a diseased state, the diagnosis support information can be generated using, as an input, the first input data that contains the ultrasound image involving the diseased state. This contributes to the improvement of efficiency in breast cancer screening. In more concrete terms, the first mammogram MG1 is processed according to the body mark BM showing the position of the ultrasound image, and the diagnosis support information can be generated through CAD using an input that includes the second mammogram MG2 obtained upon processing the first mammogram MG1, and the ultrasound image UL. Here, in the course of acquiring the ultrasound image UL, the operations of storing the ultrasound image and generating the body mark BM can be automatically performed according to the UL-CAD result, so that the throughput in breast cancer screening can be enhanced.

Modification of First Embodiment

Next, description will be given of a modification of the first embodiment. The description will basically concentrate on portions constituting differences from the first embodiment while omitting portions overlapping the first embodiment. Each of the following embodiments and modifications will be described in the same manner.

Figure 13:
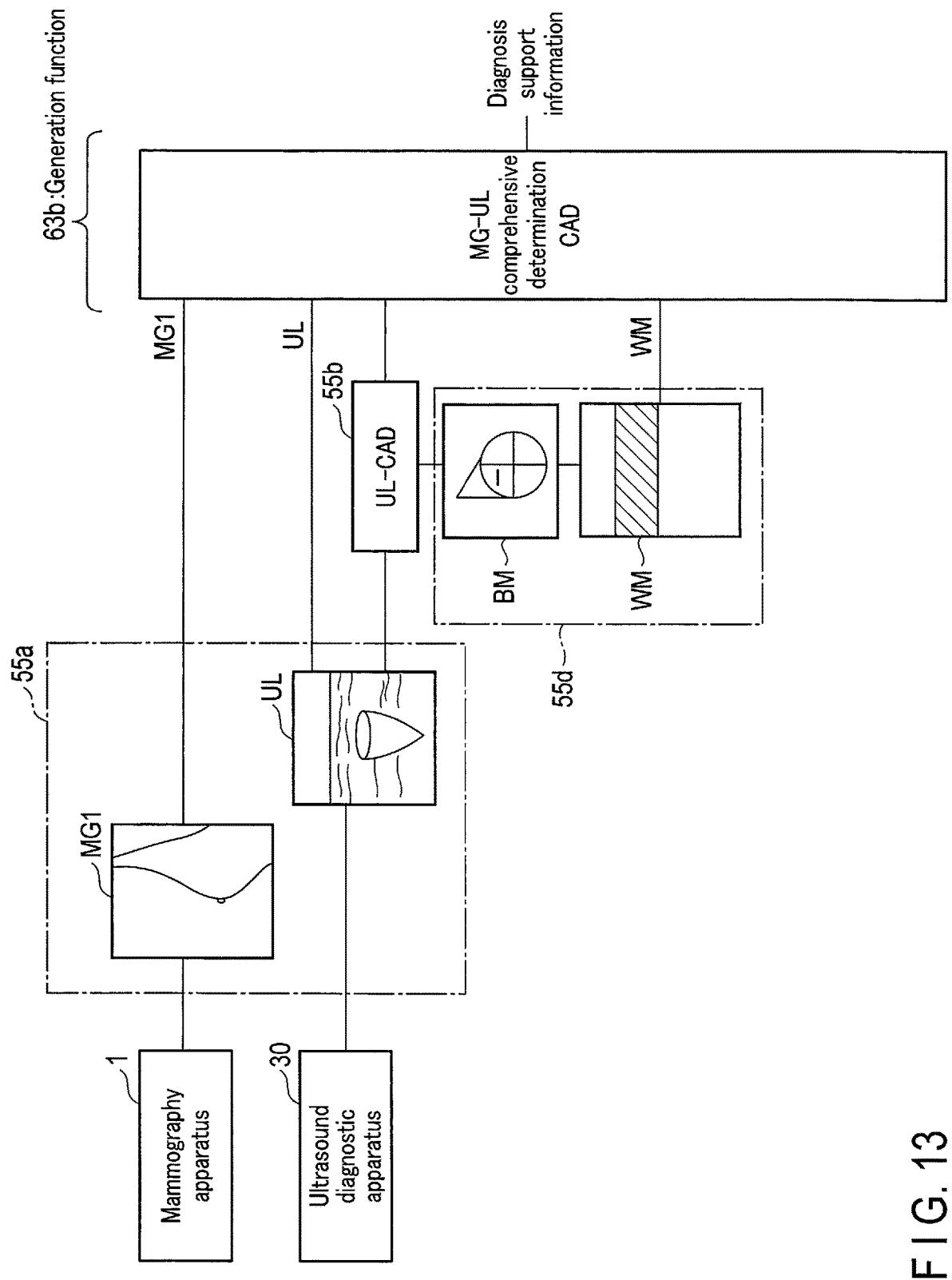
FIG. 13 is a schematic diagram showing a process according to a modification of the first embodiment, from acquisition of a first mammogram and an ultrasound image up to generation of diagnosis support information.

The modification of the first embodiment relates to a form in which the input for generating the diagnosis support information uses, as shown in FIG. 13, the first mammogram MG1 and the weight map WM in lieu of the second mammogram MG2 as in the form of the first embodiment.

Accordingly, the MG2 generation function 55e is dropped from the processing circuitry 55 of the information processing apparatus 50, and the transmit/receive function 55f is modified to some extent.

That is, the transmit/receive function 55f transmits the second input data containing the ultrasound image UL, the first mammogram MG1, and information for the corresponding position (specified by the specifying function 55d). This information for the corresponding position is the locating information indicative of the specified region of interest. As an example of the locating information, the weight map WM is used. The transmit/receive function 55f is one example of the first transmitter for transmitting the ultrasound image, the first modality image, and the information representing the imaging position for the ultrasound image.

Meanwhile, in the processing circuitry 63 of the server apparatus 60, the trained model 61a, the transmit/receive function 63a, and the generation function 63b are modified to some extent.

For the trained model 61a, the training data includes, as shown in FIG. 14, input data such as information (WM) for the corresponding position, first mammograms MG1, and ultrasound images UL, and output data which is diagnosis support information. In this case, the trained model 61a and the generation function 63b constitute one example of the generator for generating the diagnosis support information for the subject based on the ultrasound image, the imaging position for this ultrasound image, and the first modality image. The trained model 61a and the generation function 63b also constitute one example of the generator that includes the generation processor for generating the diagnosis support information for the subject based on the ultrasound image, the imaging position for this ultrasound image, and the first modality image. Note that the training data may also include, as shown in FIG. 15, UL-CAD results as the input data, in addition to the information (WM) for the corresponding position, the first mammograms MG1, and the ultrasound images UL. Thus, the trained model 61a here is a trained machine learning model that has been obtained by subjecting a machine learning model to a machine learning process using the training data as above based on the model training program.

The transmit/receive function 63a receives the second input data transmitted from the information processing apparatus 50. The transmit/receive function 63a is one example of the receiver for receiving the ultrasound image, the first modality image, and the information representing the imaging position for the ultrasound image, as well as one example of the second transmitter for transmitting the diagnosis support information.

The generation function 63b generates the diagnosis support information for the subject using an input, i.e., the second input data received by the transmit/receive function 63a. The generation function 63b is one example of the generator for generating the diagnosis support information for the subject based on the second data containing the ultrasound image, the first modality image, and the information representing the imaging position for the ultrasound image.

The remaining aspects are the same as the first embodiment.

According to the modification with the configuration as described above, the operation proceeds, for example, in such a manner as shown in FIG. 16 in which steps ST10 to ST70 are similarly performed as above while step ST80 is omitted thereafter. As such, in step ST100 after step ST70, the processing circuitry 55 of the information processing apparatus 50 transmits the second input data containing the information (WM) for the corresponding position, the first mammogram MG1, and the ultrasound image UL to the server apparatus 60.

In step ST110 after step ST100, the processing circuitry 63 of the server apparatus 60 generates, upon receipt of the second input data, diagnosis support information for the subject using the second input data as an input. In this example, the processing circuitry 63 acquires the diagnosis support information from the second input data using the trained model 61a stored in the storage 61. More specifically, the processing circuitry 63 follows the instructions from the trained model 61a to perform, based on trained parameters, arithmetic operations on the second input data input to the input layer of the trained model 61a so that the diagnosis support information is output from the output layer of the trained model 61a.

Subsequently, steps ST120 and onward are performed in the manner as described.

According to this modification, what is transmitted is the diagnosis support information generated using, as an input, the second input data containing the ultrasound image UL, the first mammogram MG1, and information for the corresponding position. Therefore, comprehensive interpretation of a mammogram and an ultrasound image is enabled and the diagnosis can be assisted as in the first embodiment. Moreover, different from the first embodiment, the computing process for generating the second mammogram MG2 can be omitted.

Second Embodiment

Next, a medical information processing system according to the second embodiment will be described.

By comparison, the second embodiment differs from the first embodiment in that it is the form in which the input for generating the diagnosis support information further includes the result of computer-aided detection with the first mammogram MG1 (i.e., MG-CAD result) as shown in FIG. 17.

Accordingly, the processing circuitry 55 of the information processing apparatus 50 additionally has an MG-CAD function 55g as shown in FIG. 18. Note that the expression "MG-CAD function" may be replaced with "MD-CAD function" in expectation of the instances where modality images other than a mammogram are subjected to the computer-aided detection processing.

The MG-CAD function 55g subjects the first mammogram MG1 acquired by the acquisition function 55a to mammography-intended CAD (MG-CAD) processing. Here, the MG-CAD processing may be performed at any timing after acquisition of the first mammogram MG1 and before transmission of the input data containing the MG-CAD result. The MG-CAD of this type may employ, for example, artificial intelligence (AI). Concrete examples that may be employed include a trained model adapted to generate the MG-CAD result using the first mammogram MG1 as an input. The MG-CAD result may be information indicative of a state from a diseased state to a non-diseased state in multiple stages, for example, in five stages from category 5 (diseased) to category 1 (non-diseased). Note that having five stages is one example, and the number of stages may be greater or less than five. Still, at least two stages are required, e.g., category 2 (diseased) and category 1 (non-diseased). The MG-CAD function 55g stores the acquired MG-CAD result in the storage 51.

The UL-CAD function 55b, by comparison with the previously described function, does not terminate the processing even when the UL-CAD result does not indicate a diseased state. This is for acquiring the diagnosis support information about a lesion candidate that is not detected from the ultrasound image UL but detected only in the first mammogram MG1.

The transmit/receive function 55f transmits the first input data which further contains the MG-CAD result in addition to the second mammogram MG2 and the ultrasound image UL as described above, to the server apparatus 60 in the server system Svs1.

In the processing circuitry 63 of the server apparatus 60, the trained model 61a and the generation function 63b are modified to some extent.

Figure 19:
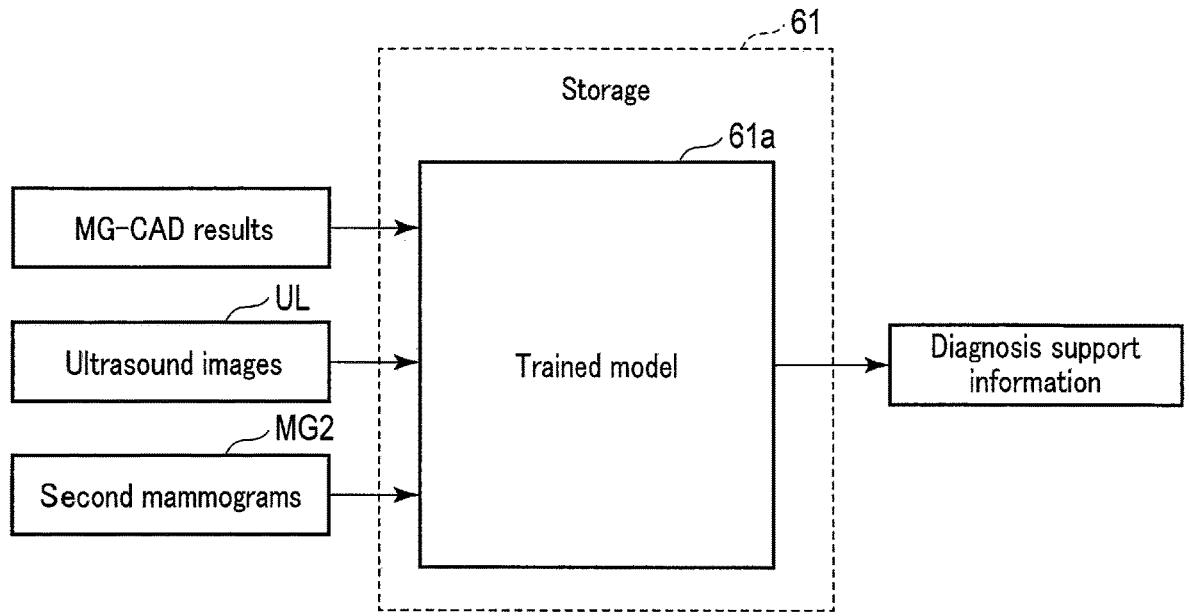
FIG. 19 is a schematic diagram for explaining a trained model according to the second embodiment.
Figure 20:
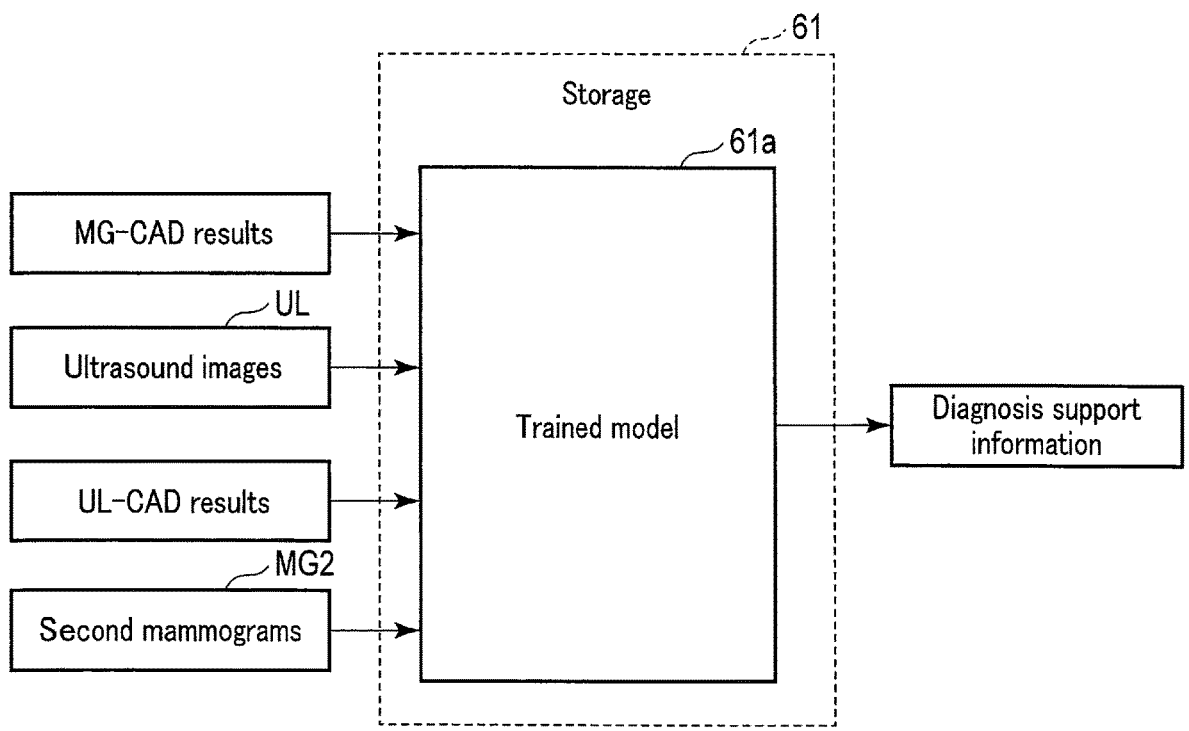
FIG. 20 is a schematic diagram for explaining a trained model according to the second embodiment.

For the trained model 61a, the training data includes, as shown in FIG. 19, input data such as MG-CAD results, ultrasound images UL, and second mammograms MG2, and output data which is diagnosis support information. Note that the training data may also include, as shown in FIG. 20, UL-CAD results as the input data, in addition to the MG-CAD results, the ultrasound images UL, and the second mammograms MG2. Thus, the trained model 61a here is a trained machine learning model that has been obtained by subjecting a machine learning model to a machine learning process using the training data as above based on the model training program.

The generation function 63b generates the diagnosis support information for the subject using an input, i.e., the first input data received by the transmit/receive function 63a. The generation function 63b is one example of the generator for generating the diagnosis support information for the subject based on the first data containing the ultrasound image and the second modality image obtained by subjecting the first modality image to the process based on the imaging position.

The remaining aspects are the same as the first embodiment.

With the configuration of the second embodiment as described above, the operation proceeds, for example, in such a manner as shown in FIG. 21 in which steps ST10 to ST50 are similarly performed as above and then the operation branches according to whether or not the UL-CAD result indicates a diseased state.

If it is determined in step ST50 that the UL-CAD result does not indicate a diseased state (ST50: N), the processing in step ST50 is repeated on condition that the ultrasound inspection is not to be terminated (ST51: N). When the ultrasound inspection is to be terminated (ST51: Y), the processing circuitry 55 performs the MG-CAD processing with the first mammogram MG1 to generate the MG-CAD result (step ST52).

In step ST53 after step ST52, the processing circuitry 55 determines whether or not the MG-CAD result indicates a diseased state, and if it does not indicate a diseased state, terminates the processing. If the MG-CAD result indicates a diseased state, the processing circuitry 55 generates the second mammogram MG2 in step ST54 by performing the trimming to take out a band-shaped region of interest having its center at the position indicating the diseased state in the first mammogram MG1.

Also, the processing circuitry 55 transmits to the ultrasound diagnostic apparatus 30 an approximate position in the first mammogram MG1 that indicates the diseased state. For example, the processing circuitry 55 may generate a body mark BM plotting the approximate position indicating the diseased state by utilizing the existing ultrasound diagnosis support function, and transmit this body mark BM to the ultrasound diagnostic apparatus 30. The ultrasound diagnostic apparatus 30 transmits the ultrasound image UL obtained through operation of the ultrasound probe 31 and corresponding to the approximate position indicating the diseased state, to the information processing apparatus 50. In this manner, the processing circuitry 55 of the information processing apparatus 50 acquires the ultrasound image UL corresponding to the approximate position indicating the diseased state. The acquired ultrasound image UL will be included in the first input data in the subsequent operation. After step ST54, the processing circuitry 55 transitions to step ST100.

Turning back to step ST50, if it is determined that the UL-CAD result indicates a diseased state (ST50: Y), the processing circuitry 55 similarly performs steps ST60 to ST80 as above. In step ST90 as an additional step after step ST80, the processing circuitry 55 performs the MG-CAD processing with the first mammogram MG1 to generate an MG-CAD result. In step ST100 after step ST90, the processing circuitry 55 of the information processing apparatus 50 transmits the first input data containing the MG-CAD result, the second mammogram MG2, and the ultrasound image UL to the server apparatus 60.

In step ST110 after step ST100, the processing circuitry 63 of the server apparatus 60 generates, upon receipt of the first input data, diagnosis support information for the subject using the first input data as an input. In this example, the processing circuitry 63 acquires the diagnosis support information from the first input data using the trained model 61a stored in the storage 61. More specifically, the processing circuitry 63 follows the instructions from the trained model 61a to perform, based on trained parameters, arithmetic operations on the first input data input to the input layer of the trained model 61a so that the diagnosis support information is output from the output layer of the trained model 61a.

Subsequently, steps ST120 and onward are performed in the manner as described.

According to the second embodiment as above, the diagnosis support information generated using, as an input, the first input data containing the MG-CAD result, the second mammogram MG2, and the ultrasound image UL is transmitted. Therefore, comprehensive interpretation of a mammogram and an ultrasound image is enabled and the diagnosis can be assisted as in the first embodiment.

According to the second embodiment, moreover, use of the MG-CAD result is assumed, in contrast to the first embodiment. Thus, the diagnosis support information can also reflect a lesion candidate that is not detected through the CAD with the ultrasound image UL but detected only through the CAD with the first mammogram MG1. On a supplementary note, in the case of the first embodiment where the second mammogram MG2 based on a result of the CAD with the ultrasound image UL is used, there is a concern that a lesion candidate not detectable through the CAD with the ultrasound image UL might be overlooked. Since the second embodiment includes the MG-CAD result with the first mammogram MG1 in the input data for generating the diagnosis support information, the second embodiment is free from such a concern.

Modification of Second Embodiment

Figure 22:
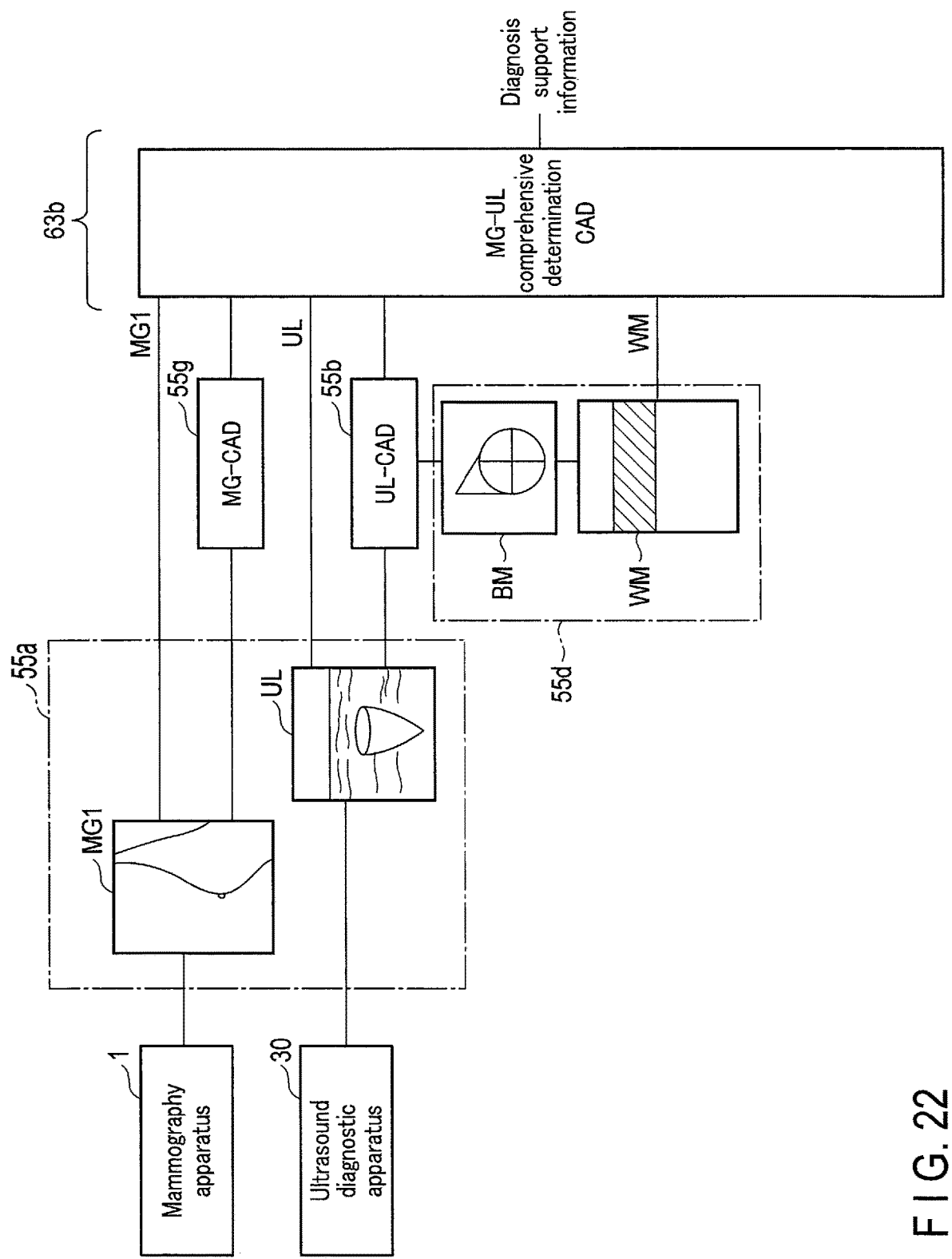
FIG. 22 is a schematic diagram showing a process according to a modification of the second embodiment, from acquisition of a first mammogram and an ultrasound image up to generation of diagnosis support information.

The modification of the second embodiment relates to a form in which the input for generating the diagnosis support information uses, as shown in FIG. 22, the first mammogram MG1 and the weight map WM in lieu of the second mammogram MG2 as in the form of the second embodiment. Note that, by comparison, the modification of the second embodiment differs from the modification of the first embodiment in that it further includes the MG-CAD result in the second input data.

In the modification of the second embodiment, accordingly, the MG2 generation function 55e is dropped from the processing circuitry 55 of the information processing apparatus 50, and the transmit/receive function 55f is modified to some extent.

More specifically, the transmit/receive function 55f transmits the second input data containing the ultrasound image UL, the first mammogram MG1, the information for the corresponding position (specified by the specifying function 55d), and also the MG-CAD result. The information for the corresponding position is the locating information indicative of the specified region of interest. As an example of the locating information, the weight map WM is used.

Meanwhile, in the processing circuitry 63 of the server apparatus 60, the trained model 61a, the transmit/receive function 63a, and the generation function 63b are modified to some extent.

For the trained model 61a, the training data includes, as shown in FIG. 23, input data such as information (WM) for the corresponding position, first mammograms MG1, ultrasound images UL, and MG-CAD results, and output data which is diagnosis support information. Note that the training data may also include, as shown in FIG. 24, UL-CAD results as the input data, in addition to the information (WM) for the corresponding position, the first mammograms MG1, the ultrasound images UL, and the MG-CAD results. The trained model 61a in this case is one example of the generation processor for generating the diagnosis support information for the subject based on inputs including the result of computer-aided detection performed with the ultrasound image UL, the result of computer-aided detection performed with the first modality image MD1, the imaging position for the ultrasound image UL, the ultrasound image UL, and the first modality image MD1. The case shown in FIG. 24 may be further modified so that the first mammograms MG1 and the ultrasound images UL are dropped and the input data includes the information (WM) for the corresponding position, the MG-CAD results, and the UL-CAD results. When this dropping is adopted, the trained model 61a is one example of the generation processor for generating the diagnosis support information for the subject based on inputs including the result of computer-aided detection performed with the ultrasound image UL, the result of computer-aided detection performed with the first modality image MD1, and the imaging position for the ultrasound image UL. In any case, the trained model 61a is a trained machine learning model that has been obtained by subjecting a machine learning model to a machine learning process using the training data as above based on the model training program.

The transmit/receive function 63a receives the second input data transmitted from the information processing apparatus 50.

The generation function 63b generates the diagnosis support information for the subject using an input, i.e., the second input data received by the transmit/receive function 63a.

The remaining aspects are the same as the second embodiment.

According to the modification with the configuration as described above, the operation proceeds, for example, in such a manner as shown in FIG. 25 in which steps ST10 to ST70 are similarly performed as above while step ST80 is omitted thereafter, and the MG-CAD result is generated in step ST90 as above. As such, in step ST100 after step ST90, the processing circuitry 55 of the information processing apparatus 50 transmits the second input data containing the information (WM) for the corresponding position, the first mammogram MG1, the ultrasound image UL, and the MG-CAD result to the server apparatus 60.

In step ST110 after step ST100, the processing circuitry 63 of the server apparatus 60 generates, upon receipt of the second input data, diagnosis support information for the subject using the second input data as an input.

Subsequently, steps ST120 and onward are performed in the manner as described.

According to the modification of the second embodiment, what is transmitted is the diagnosis support information generated using, as an input, the second input data containing the information for the corresponding position, the first mammogram MG1, the ultrasound image UL, and the MG-CAD result. Therefore, in addition to the effects of the second embodiment, the modification allows the computing process for generating the second mammogram MG2 to be omitted.

Third Embodiment

Next, a medical information processing system according to the third embodiment will be described.

The third embodiment is a modification of the first embodiment and relates to a form in which the client system includes multiple information processing apparatuses.

Figure 26:
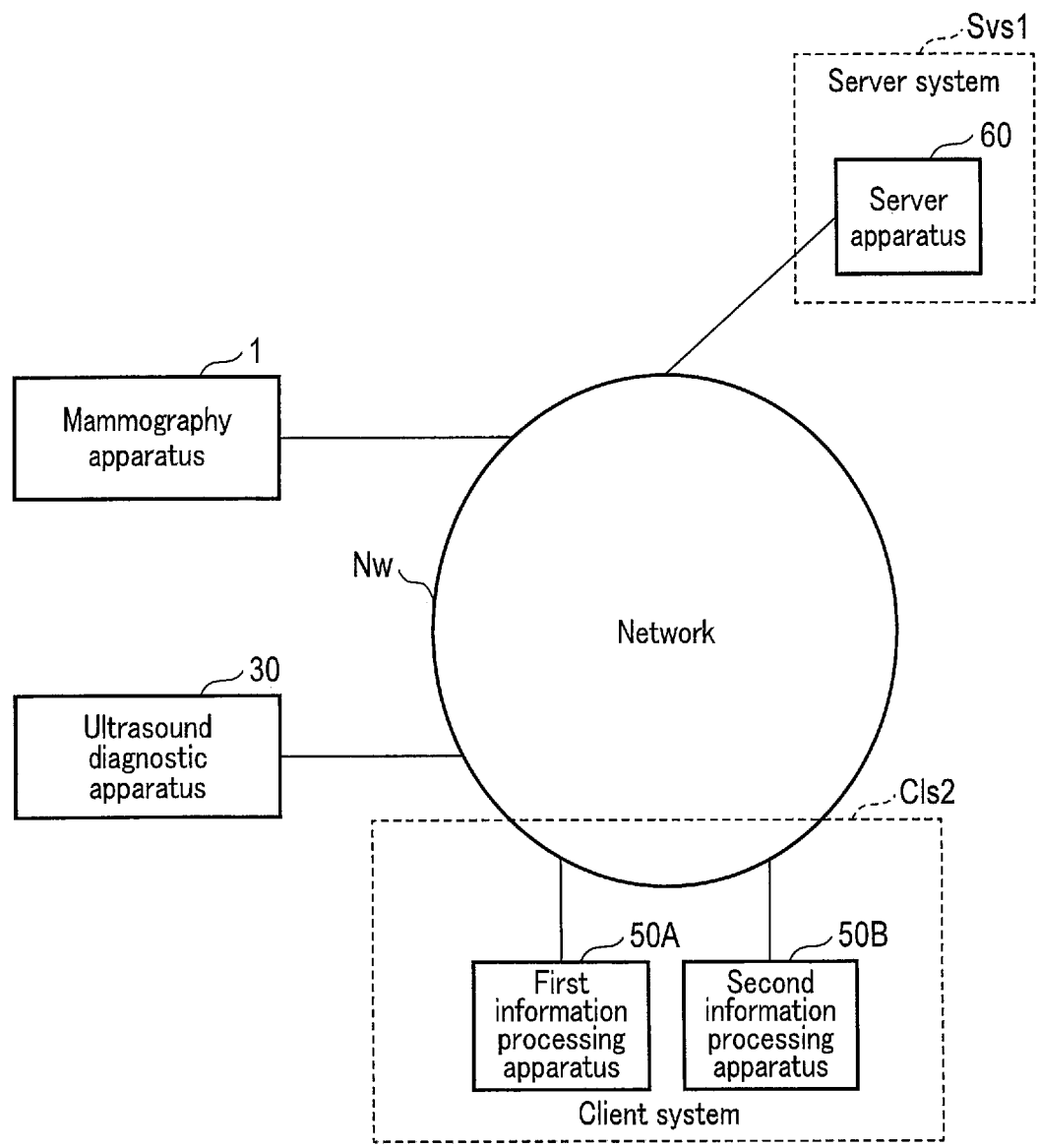
FIG. 26 is a block diagram showing a configuration of a medical information processing system according to a third embodiment.
Figure 27:
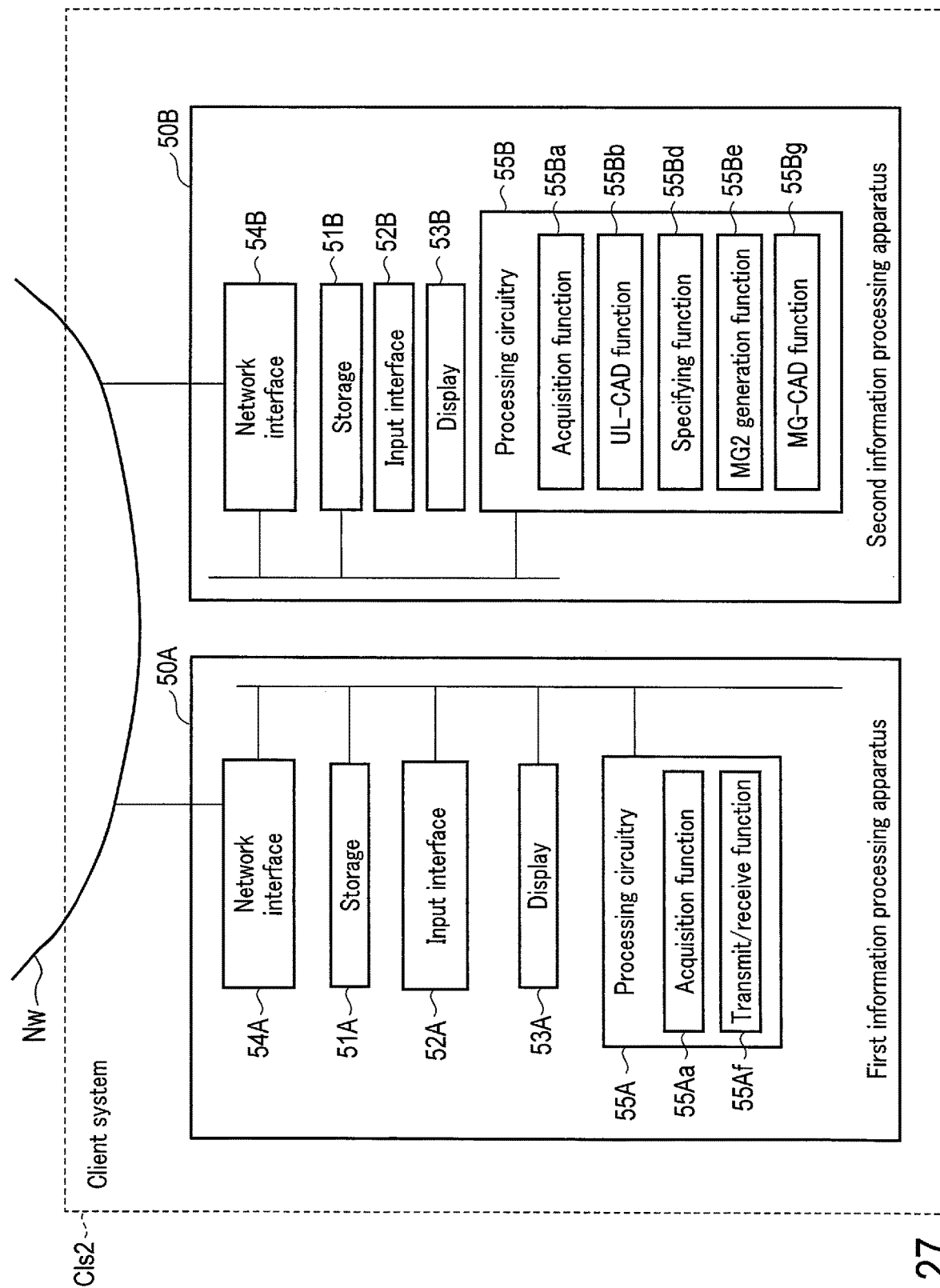
FIG. 27 is a block diagram showing a configuration of an information processing apparatus in a client system according to the third embodiment.

Referring to an example shown in FIGS. 26 and 27, a client system Cls2 includes a first information processing apparatus 50A and a second information processing apparatus 50B.

Note that the first information processing apparatus 50A and the second information processing apparatus 50B may be distributively assigned the previously described functions of the information processing apparatus 50. Accordingly, the first information processing apparatus 50A and the second information processing apparatus 50B together provide the same functions as the above-described information processing apparatus 50, except for functions for performing transmission and reception between themselves. To put it another way, the contents of the transmission and reception by the client system Cls2 are the same as those of the above-described client system Cls1.

More specifically, the first information processing apparatus 50A includes storage 51A, an input interface 52A, a display 53A, a network interface 54A, and processing circuitry 55A. The processing circuitry 55A realizes an acquisition function 55Aa and a transmit/receive function 55Af. The constituting features (51A to 55A, 55Aa, and 55Af) of the first information processing apparatus 50A are denoted by reference symbols of the corresponding constituting features (51 to 55, 55a, and 55f) of the above-described information processing apparatus 50 with an additional symbol "A", and they function in the same manner as the respective constituting features of the information processing apparatus 50.

The second information processing apparatus 50B includes storage SIB, an input interface 52B, a display 53B, a network interface 54B, and processing circuitry 55B. The processing circuitry 55B realizes an acquisition function 55Ba, a UL-CAD function 55Bb, a specifying function 55Bd, an MG2 generation function 55Be, and an MG-CAD function 55Bg. The constituting features (51B to 55B, 55Ba to 55Be, and 55Bg) of the second information processing apparatus 50B are denoted by reference symbols of the corresponding constituting features (51 to 55, 55a to 55e, and 55g) of the above-described information processing apparatus 50 with an additional symbol "B", and they function in the same manner as the respective constituting features of the information processing apparatus 50.

The remaining aspects are the same as the first embodiment.

With the configuration as described above, the operation proceeds, for example, in such a manner as shown in FIG. 28 in which steps ST10 to ST20 are similarly performed as above and then step ST21 is performed where the first information processing apparatus 50A transmits the first mammogram MG1 to the second information processing apparatus SOB. In step ST31 after step ST21 and also after step ST30, the first information processing apparatus 50A transmits the ultrasound image UL and the imaging position information for the ultrasound image UL to the second information processing apparatus 50B.

After step ST31, the second information processing apparatus 50B similarly performs steps ST40 to ST50 as above and transmits, if the UL-CAD indicates a diseased state, the ultrasound image UL to the first information processing apparatus 50A (step ST56).

In step ST57 after step ST56, the first information processing apparatus 50A stores the received ultrasound image UL in the storage 51A.

Meanwhile, the second information processing apparatus SOB similarly performs steps ST60 to ST80 as above after step ST56, and in step ST81 transmits the second mammogram MG2 to the first information processing apparatus 50A.

In step ST100 after step ST81, the processing circuitry 55A of the first information processing apparatus 50A transmits the first input data containing the received second mammogram MG2 and the ultrasound image UL that is stored in the storage 51A to the server apparatus 60.

Subsequently, steps ST110 and onward are performed in the manner as described.

According to the third embodiment as described above, where the functions of the information processing apparatus 50 in the first embodiment are distributively assigned to two information processing apparatuses (50A and 50B), the same effects as in the first embodiment can be attained. That is, the first input data destined for the server apparatus 60 and the diagnosis support information according to the third embodiment are the same as the first input data and the diagnosis support information according to the first embodiment, and therefore, the same effects as in the first embodiment can result.

Furthermore, as shown in FIG. 29, the configuration according to the third embodiment, where the two information processing apparatuses (50A and 50B) distributively include the intended functions, can be applied to the modification of the first embodiment that relates to the use of the second input data. When such an application is implemented, the same effects as in the modification of the first embodiment can be attained.

Figure 30:
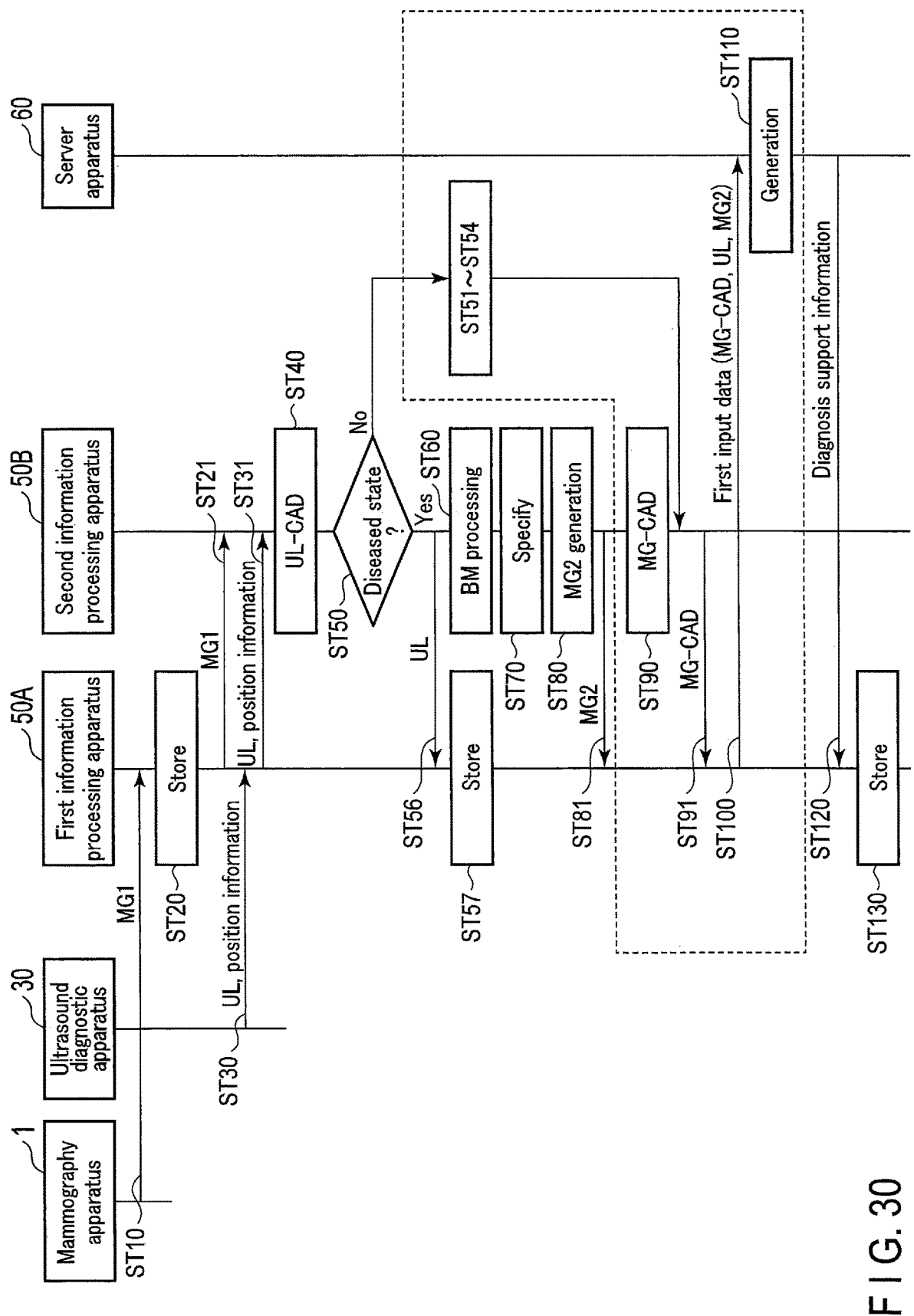
FIG. 30 is a sequence diagram for explaining operations according to another modification of the third embodiment.

As shown in FIG. 30, the configuration according to the third embodiment, where the two information processing apparatuses (50A and 50B) distributively include the intended functions, can be likewise applied to the second embodiment that relates to the use of the first input data containing the MG-CAD result. When such an application is implemented, the same effects as in the second embodiment can be attained.

Figure 31:
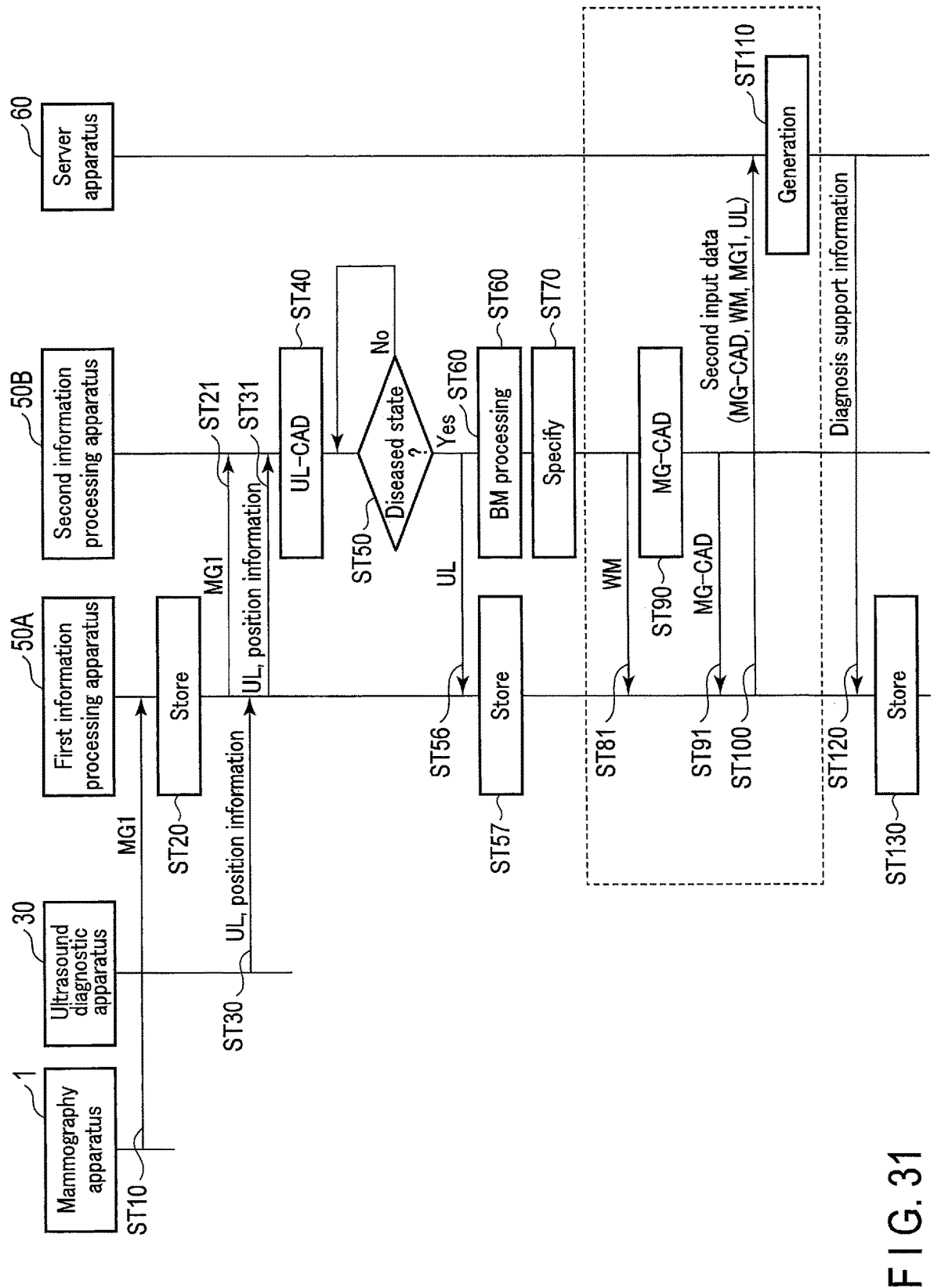
FIG. 31 is a sequence diagram for explaining operations according to yet another modification of the third embodiment.

As shown in FIG. 31, the configuration according to the third embodiment, where the two information processing apparatuses (50A and 50B) distributively include the intended functions, can be likewise applied to the modification of the second embodiment that relates to the use of the second input data containing the MG-CAD result. When such an application is implemented, the same effects as in the modification of the second embodiment can be attained.

Fourth Embodiment

Next, a medical information processing system according to the fourth embodiment will be described.

The fourth embodiment is a modification of the first embodiment and relates to a form in which the client system performs image acquisition and transmission/reception, and the server system handles operations from the UL-CAD processing to the generation of diagnosis support information.

Figure 32:
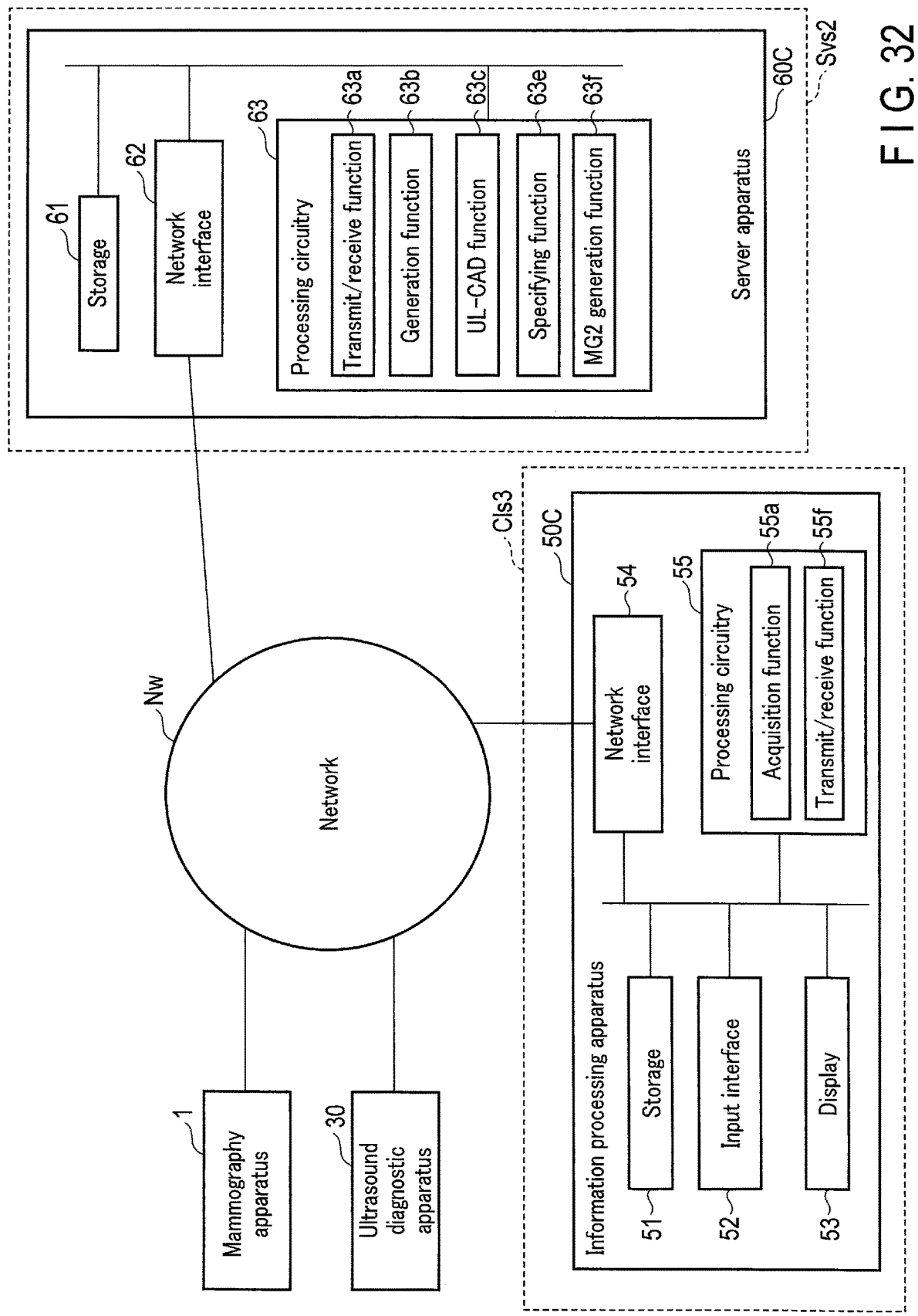
FIG. 32 is a block diagram showing a configuration of a medical-information processing system according to a fourth embodiment.

Referring to an example shown in FIG. 32, a client system Cls3 includes an information processing apparatus 50C as at least one information processing apparatus. A server system Svs2 includes a server apparatus 60C as at least one server apparatus.

By comparison, the information processing apparatus 50C here differs from the configuration shown in FIG. 5 in that it omits the UL-CAD function 55b, the specifying function 55d, and the MG2 generation function 55e among the functions 55a to 55f realized by the processing circuitry 55. That is, the processing circuitry 55 according to this embodiment realizes the acquisition function 55a and the transmit/receive function 55f through execution of the control program stored in the storage 51. The transmit/receive function 55f is modified to some extent.

The acquisition function 55a includes the first acquisition function for acquiring the ultrasound image UL of the subject and the second acquisition function for acquiring the first mammogram MG1 of the same subject. Note that the first acquisition function may acquire the imaging position information for the ultrasound image UL (position information of the ultrasound probe 31) together with the ultrasound image UL in real time. The second acquisition function is one example of a second acquirer for acquiring the first modality image of the subject that differs from an ultrasound image.

The transmit/receive function 55f is a function for performing transmission and reception with other apparatuses. In one example, the transmit/receive function 55f transmits the first mammogram MG1 acquired by the acquisition function 55a to the server apparatus 60C. The transmit/receive function 55f also transmits the ultrasound image UL and the imaging position information for the ultrasound image UL, acquired by the acquisition function 55a, to the server apparatus 60C. The transmit/receive function 55f receives the diagnosis support information from the server apparatus 60C.

By comparison, the server apparatus 60C here differs from the configuration shown in FIG. 8 in that it includes a UL-CAD function 63c, a specifying function 63e, and an MG2 generation function 63f in addition to the functions 63a and 63b as functions realized by the processing circuitry 63. That is, the processing circuitry 63 according to this embodiment realizes the transmit/receive function 63a, the generation function 63b, the UL-CAD function 63c, the specifying function 63e, and the MG2 generation function 63f through execution of the control program stored in the storage 61. The transmit/receive function 63a and the generation function 63b are modified to some extent. The additionally included functions, i.e., the UL-CAD function 63c, the specifying function 63e, and the MG2 generation function 63f may be taken as the above-described UL-CAD function 55b, specifying function 55d, and MG2 generation function 55e that have been assigned to the server apparatus 60C. Thus, where to acquire images is different to some extent.

The transmit/receive function 63a is a function for performing transmission and reception with other apparatuses, and it receives, for example, the first mammogram MG1, the ultrasound image UL, and the imaging position information for the ultrasound image UL from the information processing apparatus 50C. Also, the transmit/receive function 63a transmits the diagnosis support information generated by the generation function 63b.

The generation function 63b generates the diagnosis support information for the subject using, as an input, the first input data containing the second mammogram MG2 generated by the MG2 generation function 63f and the ultrasound image UL received by the transmit/receive function 63a, or the second input data containing the first mammogram MG1 and the ultrasound image UL which have been received by the transmit/receive function 63a. Note that the description of the fourth embodiment will assume instances where the former one, i.e., the first input data, is adopted. The case of the latter one, i.e., the second input data, will be described with reference to a modification of the fourth embodiment. The diagnosis support information is as already discussed. Also, the generation function 63b generates the diagnosis support information by utilizing the trained model 61a as previously described. The generation function 63b is one example of the generator for generating the diagnosis support information for the subject based on the first data containing the ultrasound image and the second modality image obtained by subjecting the first modality image to the process based on the imaging position for the ultrasound image, or the second data containing the information representing the imaging position for the ultrasound image, the first modality image, and the ultrasound image.

The UL-CAD function 63c subjects the ultrasound image UL received by the transmit/receive function 63a to ultrasound-intended CAD (UL-CAD) processing in the manner as described above. Similar to the above, also, the UL-CAD function 63c stores the ultrasound image UL in the storage 61 and activates the specifying function 63e, in response to the UL-CAD result indicating a diseased state.

The specifying function 63e specifies, based on the imaging position information for the ultrasound image UL, the corresponding position on the first mammogram MG1. More specifically, and for example, the specifying function 63e plots a mark mk indicative of the imaging position for the ultrasound image UL on a body mark BM of the breast based on the imaging position information for the ultrasound image UL. The specifying function 63e also specifies, on the first mammogram MG1, a region of interest of a band-shaped range having its center at the position of the mark mk, and generates the locating information indicative of the specified region of interest. Examples that may be used as the locating information include, as previously described, the weight map WM, trimming information, and so on. The specifying function 63e stores the body mark BM with the plotted mark mk in the storage 61, in association with the ultrasound image UL that has been stored by the UL-CAD function 63c. The specifying function 63e is one example of the specifier for specifying, based on the imaging position information for an ultrasound image, a position on the first modality image that corresponds to the imaging position.

The MG2 generation function 63f generates the second mammogram MG2 by, for example, processing the first mammogram MG1 based on the position specified by the specifying function 63e. More specifically, and for example, the second mammogram MG2 may be generated by multiplying each pixel value of the first mammogram MG1 by the respective pixel value of the weight map WM as described above. Similar to the above, also, the MG2 generation function 63f may generate the second mammogram MG by trimming the first mammogram MG1 based on the trimming information. The MG2 generation function 63f is one example of the image generator for generating the second modality image by subjecting the first modality image to the process based on the imaging position for the ultrasound image.

Next, how the medical information processing system configured as above operates will be described with reference to FIG. 33.

Suppose that steps ST10 to ST20 have been performed in the manner as described. In step ST21 after step ST20, the processing circuitry 55 of the information processing apparatus 50C transmits the first mammogram MG1 to the server apparatus 60C. The server apparatus 60C receives the first mammogram MG1.

After step ST21, step ST30 is performed in the manner as discussed.

In step ST31 after step ST30, the processing circuitry 55 of the information processing apparatus 50C transmits the ultrasound image UL and the imaging position information for the ultrasound image UL to the server apparatus 60C. The server apparatus 60C receives the ultrasound image UL and the imaging position information for the ultrasound image UL.

In step ST40 after step ST31, the processing circuitry 63 of the server apparatus 60C performs UL-CAD processing with the received ultrasound image to generate a UL-CAD result.

In step ST50 after step ST40, the processing circuitry 63 determines whether or not the UL-CAD result indicates a diseased state, and if it does not indicate a diseased state, repeats this determining action until the end of the ultrasound inspection. On the other hand, if the UL-CAD result indicates a diseased state, the processing circuitry 63 stores the applicable ultrasound image UL in the storage 61. In this case of the UL-CAD result indicating a diseased state, this ultrasound image UL is transmitted to the information processing apparatus 50C (step ST56).

In step ST57 after step ST56, the information processing apparatus 50C stores the received ultrasound image UL in the storage 51.

Meanwhile, after step ST56, steps ST60 to ST70 are performed in the server apparatus 60C, where the processing circuitry 63 refers to the imaging position information for the ultrasound image UL to specify a corresponding position on the first mammogram MG1. For example, in step ST60, a mark mk indicative of the imaging position for the ultrasound image UL is plotted on a body mark BM of the breast. The processing circuitry 63 also stores the body mark BM with the plotted mark mk in the storage 61, in association with the ultrasound image UL that has been stored.

Then in step ST70, the processing circuitry 63 specifies, on the first mammogram MG1, a region of interest of a band-shaped range having the center at the position of the mark mk. The processing circuitry 63 also generates a weight map WM for putting a greater weight on the specified region of interest, as described above.

In step ST80 after step ST70, the processing circuitry 63 generates a second mammogram MG2 by subjecting the first mammogram MG1 to the process based on the position specified in step ST70. In this example, each pixel value of the weight map WM and the respective pixel value of the first mammogram MG1 are multiplied so as to generate the second mammogram MG2 emphasizing the region of interest from the first mammogram MG1.

In step ST110 after step ST80, the processing circuitry 63 generates diagnosis support information for the subject using, as an input, the first input data containing the generated second mammogram MG2 and the ultrasound image UL that is stored in the storage 61. In this example, the processing circuitry 63 uses the trained model 61a stored in the storage 61 as described above.

In step ST120 after step ST110, the processing circuitry 63 transmits the generated diagnosis support information to the information processing apparatus 50C.

In step ST130 after step ST120, the processing circuitry 55 of the information processing apparatus 50C stores the diagnosis support information in the storage 51, upon receipt of the diagnosis support information. The processing circuitry 55 controls the display 53 to display the diagnosis support information, the first mammogram MG1, and the ultrasound image which are stored in the storage 51, according to an operation by the operator (interpreting doctor). In this manner, support for the interpreting doctor's diagnosing work is provided.

As described above, the fourth embodiment employs a medical information processing system including a client system with at least one information processing apparatus and a server system with at least one server apparatus. The client system acquires an ultrasound image of a subject, acquires a first mammogram of the subject, and transmits the ultrasound image, the first mammogram, and the imaging position information for the ultrasound image. The server system receives the ultrasound image, the first mammogram, and the imaging position information for the ultrasound image, and specifies, based on the imaging position information for the ultrasound image, a corresponding position on the first mammogram. The server system also generates diagnosis support information for the subject using, as an input, the first input data containing a second mammogram obtained by processing the first mammogram based on the corresponding position, and the ultrasound image, and transmits the diagnosis support information.

With this configuration of transmitting the diagnosis support information generated using, as an input, the first input data containing the second mammogram and the ultrasound image, comprehensive interpretation of the mammogram and the ultrasound image is enabled, and support for the diagnosis can be provided.

Modification of Fourth Embodiment

The modification of the fourth embodiment is obtained by applying the fourth embodiment to the modification of the first embodiment. The modification of the fourth embodiment relates to a form in which the input for generating the diagnosis support information uses the first mammogram MG1 and the weight map WM in lieu of the second mammogram MG2 as in the form of the fourth embodiment.

Accordingly, the MG2 generation function 63f is dropped from the processing circuitry 63 of the server apparatus 60C, and the trained model 61a and the generation function 63b are modified to some extent.

For the trained model 61a, the training data includes input data such as information (WM) for the corresponding position, first mammograms MG1, and ultrasound images UL, and output data which is diagnosis support information. Note that the training data may also include UL-CAD results as the input data, in addition to the information (WM) for the corresponding position, the first mammograms MG1, and the ultrasound images UL. Thus, the trained model 61a is a trained machine learning model that has been obtained by subjecting a machine learning model to a machine learning process using such training data based on the model training program.

The generation function 63b generates the diagnosis support information using, as an input, the second input data containing the information (1M) for the corresponding position, the first mammogram MG1, and the ultrasound image UL.

The remaining aspects are the same as the fourth embodiment.

Figure 34:
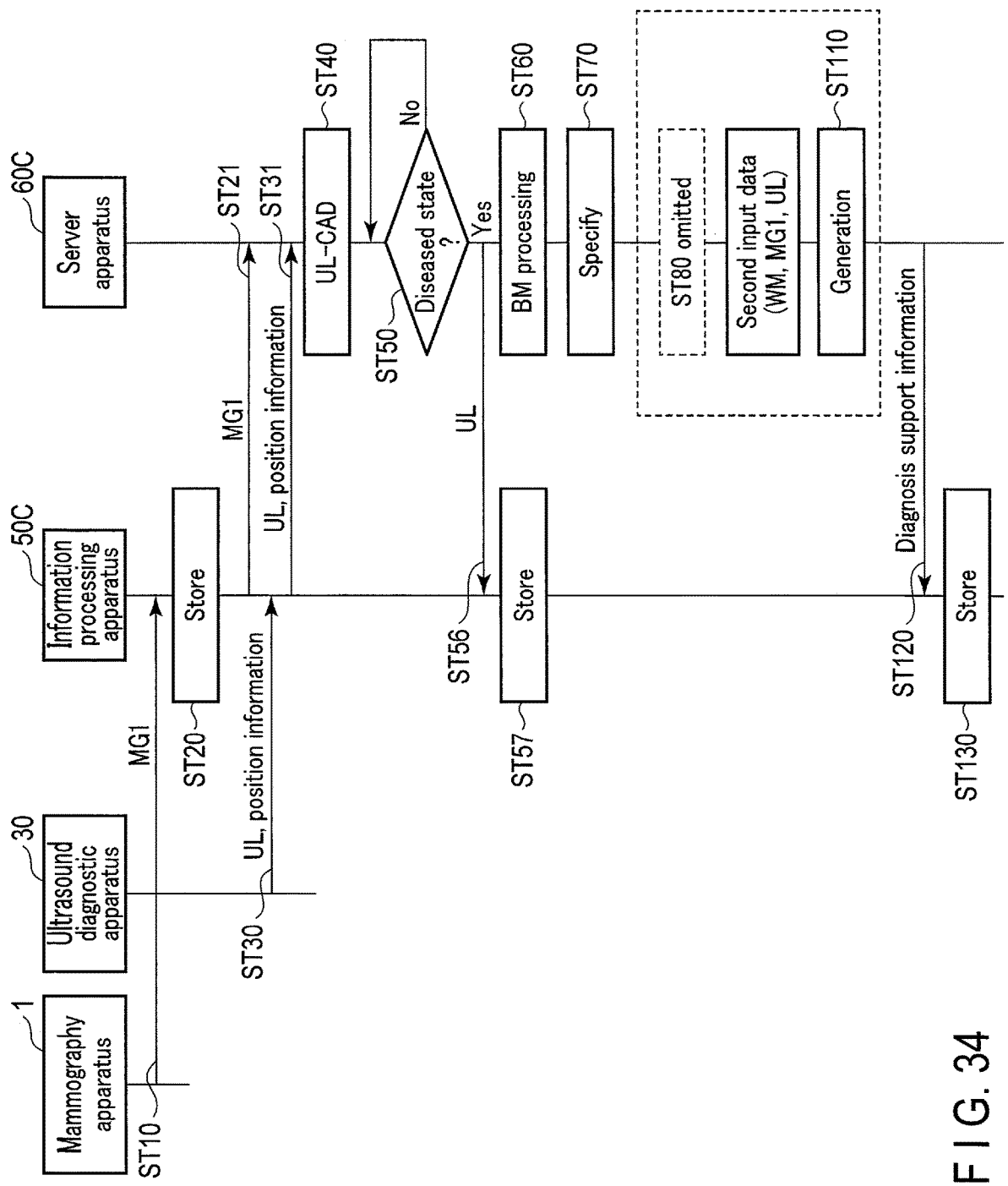
FIG. 34 is a sequence diagram for explaining operations according to a modification of the fourth embodiment.

According to the modification with the above configuration, the operation proceeds, for example, in such a manner as shown in FIG. 34 in which steps ST10 to ST70 are similarly performed as above while step ST80 is omitted thereafter. As such, in step ST110 after step ST70, the processing circuitry 63 of the server apparatus 60C generates the diagnosis support information using, as an input, the second input data containing the information (WM) for the corresponding position, the first mammogram MG1, and the ultrasound image UL. In this example, the processing circuitry 63 generates the diagnosis support information from the second input data using, as described above, the trained model 61a stored in the storage 61.

Subsequently, steps ST120 and onward are performed in the manner as described.

According to this modification, the diagnosis support information generated using, as an input, the second input data containing the information for the corresponding position, the first mammogram MG1, and the ultrasound image UL is transmitted. Therefore, comprehensive interpretation of a mammogram and an ultrasound image is enabled and the diagnosis can be assisted as in the fourth embodiment. Moreover, different from the fourth embodiment, the computing process for generating the second mammogram MG2 can be omitted.

Fifth Embodiment

Next, a medical information processing system according to the fifth embodiment will be described.

The fifth embodiment is obtained by applying the fourth embodiment to the above second embodiment. By comparison, the fifth embodiment differs from the fourth embodiment in that it is the form in which the input for generating the diagnosis support information additionally includes the result of CAD with the first mammogram MG1 (i.e., MG-CAD result).

Figure 35:
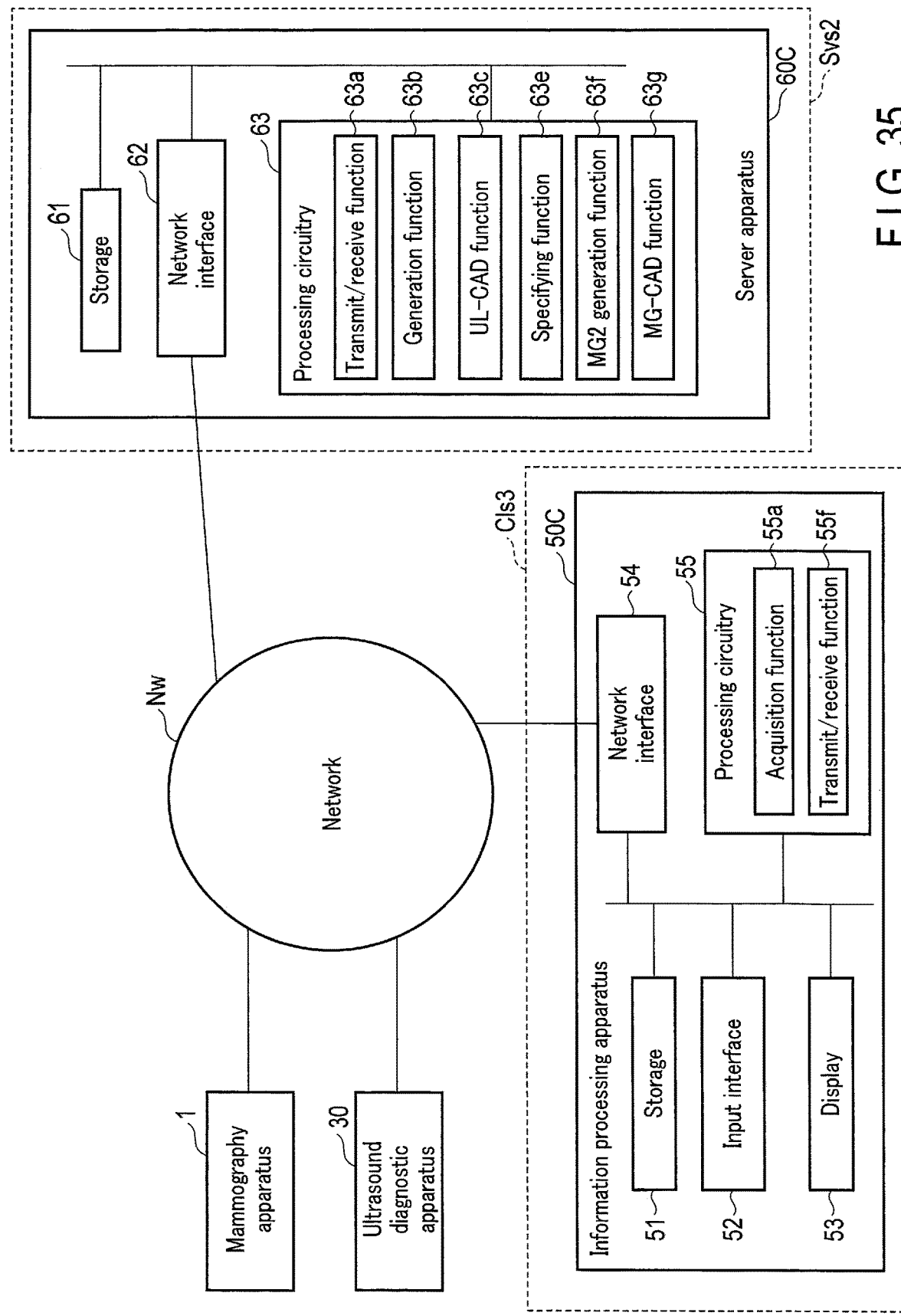
FIG. 35 is a block diagram showing a configuration of a medical information processing system according to a fifth embodiment.

Accordingly, the processing circuitry 63 of the server apparatus 60C additionally has an MG-CAD function 63g as shown in FIG. 35.

The MG-CAD function 63g subjects the first mammogram MG1 received by the transmit/receive function 63a to mammography-intended CAD (MG-CAD) processing, in response to the UL-CAD result indicating a diseased state. Here, the MG-CAD processing may be performed at any timing after performing the UL-CAD function 63c and before performing the generation function 63b. The MG-CAD of this type may employ, for example, artificial intelligence (AI) as discussed above, and a trained model adapted to generate the MG-CAD result using the first mammogram MG1 as an input can be used. Particulars about the MG-CAD result are as previously described. The MG-CAD function 63g stores the acquired MG-CAD result in the storage 61.

In the processing circuitry 63 of the server apparatus 60C, the trained model 61a and the generation function 63b are modified to some extent.

For the trained model 61a, the training data includes input data such as MG-CAD results, ultrasound images UL, and second mammograms MG2, and output data which is diagnosis support information. Note that the training data may also include UL-CAD results as the input data, in addition to the MG-CAD results, the ultrasound images UL, and the second mammograms MG2. Thus, the trained model 61a is a trained machine learning model that has been obtained by subjecting a machine learning model to a machine learning process using such training data based on the model training program.

The generation function 63b generates the diagnosis support information for the subject using, as an input, the first input data further containing the MG-CAD result in addition to the second mammogram MG2 and the ultrasound image UL as described above.

The remaining aspects are the same as the fourth embodiment.

Figure 36:
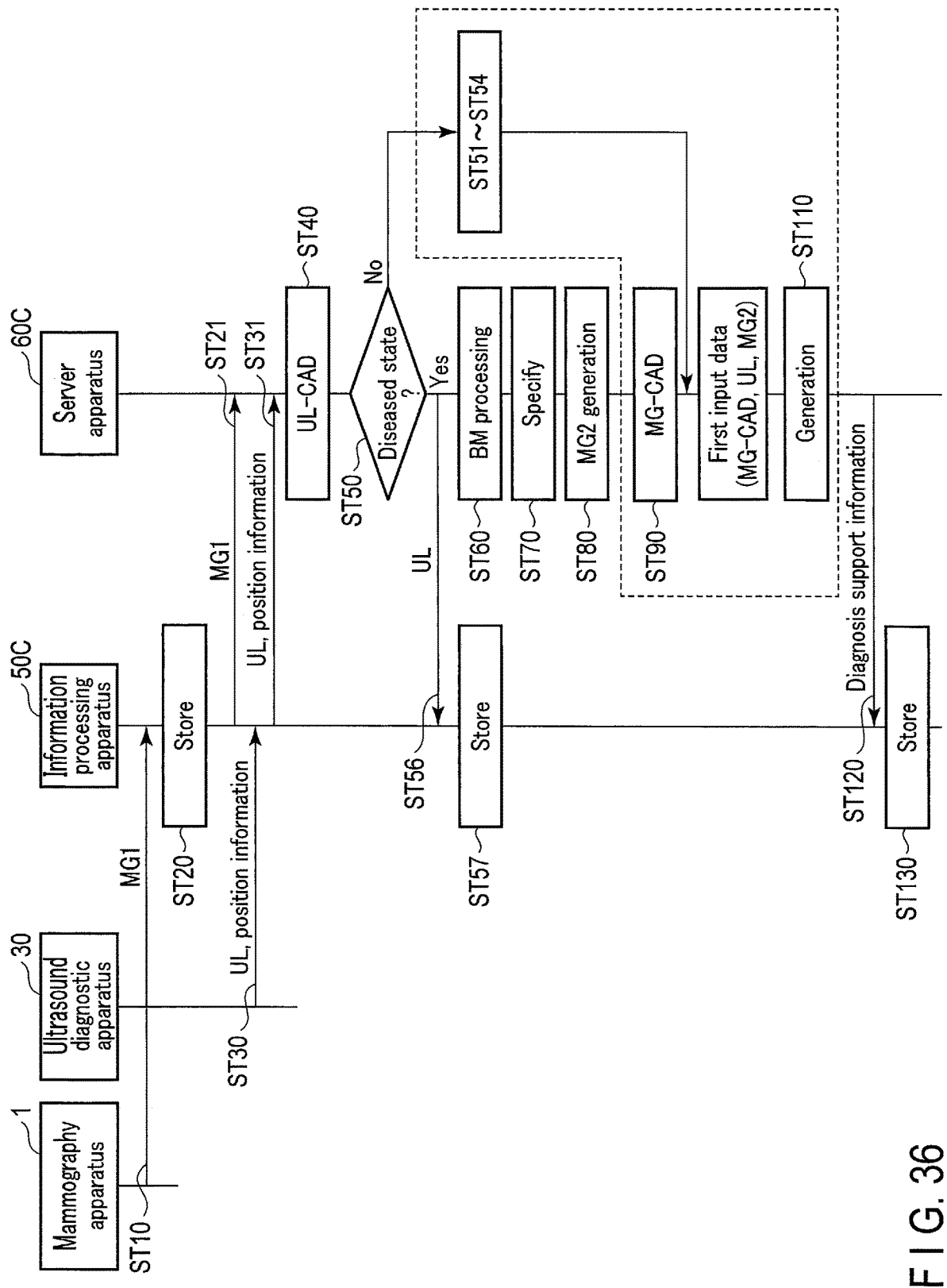
FIG. 36 is a sequence diagram for explaining operations according to the fifth embodiment.

With the configuration of the fifth embodiment as described above, the operation proceeds, for example, in such a manner as shown in FIG. 36 in which steps ST10 to ST80 are similarly performed as above, and then in step ST90 as an additional step, the processing circuitry 63 of the server apparatus 60C performs the MG-CAD processing with the first mammogram MG1 to generate an MG-CAD result. In step ST110 after step ST90, the processing circuitry 63 generates diagnosis support information for the subject using, as an input, the first input data containing the MG-CAD result, the second mammogram MG2, and the ultrasound image UL.

Subsequently, steps ST120 and onward are performed in the manner as described.

According to the fifth embodiment as above, the diagnosis support information generated using, as an input, the first input data containing the MG-CAD result, the second mammogram MG2, and the ultrasound image UL is transmitted. Therefore, comprehensive interpretation of a mammogram and an ultrasound image is enabled and the diagnosis can be assisted as in the fourth embodiment.

According to the fifth embodiment, moreover, use of the MG-CAD result is assumed, in contrast to the fourth embodiment. Thus, the diagnosis support information can also reflect a lesion candidate that is not detected through the CAD with the ultrasound image UL but detected only through the CAD with the first mammogram MG1.

Modification of Fifth Embodiment

The modification of the fifth embodiment is obtained by applying the fifth embodiment to the modification of the second embodiment above. That is, the modification of the fifth embodiment relates to a form in which the input for generating the diagnosis support information uses the first mammogram MG1 and the weight map WM in lieu of the second mammogram MG2 as in the form of the fifth embodiment. Note that, by comparison, the modification of the fifth embodiment differs from the modification of the fourth embodiment in that it additionally includes the MG-CAD result in the second input data.

In the modification of the fifth embodiment, accordingly, the MG2 generation function 63f is dropped from the processing circuitry 63 of the server apparatus 60C, and the trained model 61a and the generation function 63b are modified to some extent.

For the trained model 61a, the training data includes input data such as information (WM) for the corresponding position, first mammograms MG1, ultrasound images UL, and MG-CAD results, and output data which is diagnosis support information. Note that the training data may also include UL-CAD results as the input data, in addition to the information (WM) for the corresponding position, the first mammograms MG1, the ultrasound images UL, and the MG-CAD results. Thus, the trained model 61a is a trained machine learning model that has been obtained by subjecting a machine learning model to a machine learning process using such training data based on the model training program.

The generation function 63b generates the diagnosis support information for the subject using, as an input, the second input data containing the information (WM) for the corresponding position, the first mammogram MG1, the ultrasound image UL, and the MG-CAD result.

The remaining aspects are the same as the fifth embodiment.

Figure 37:
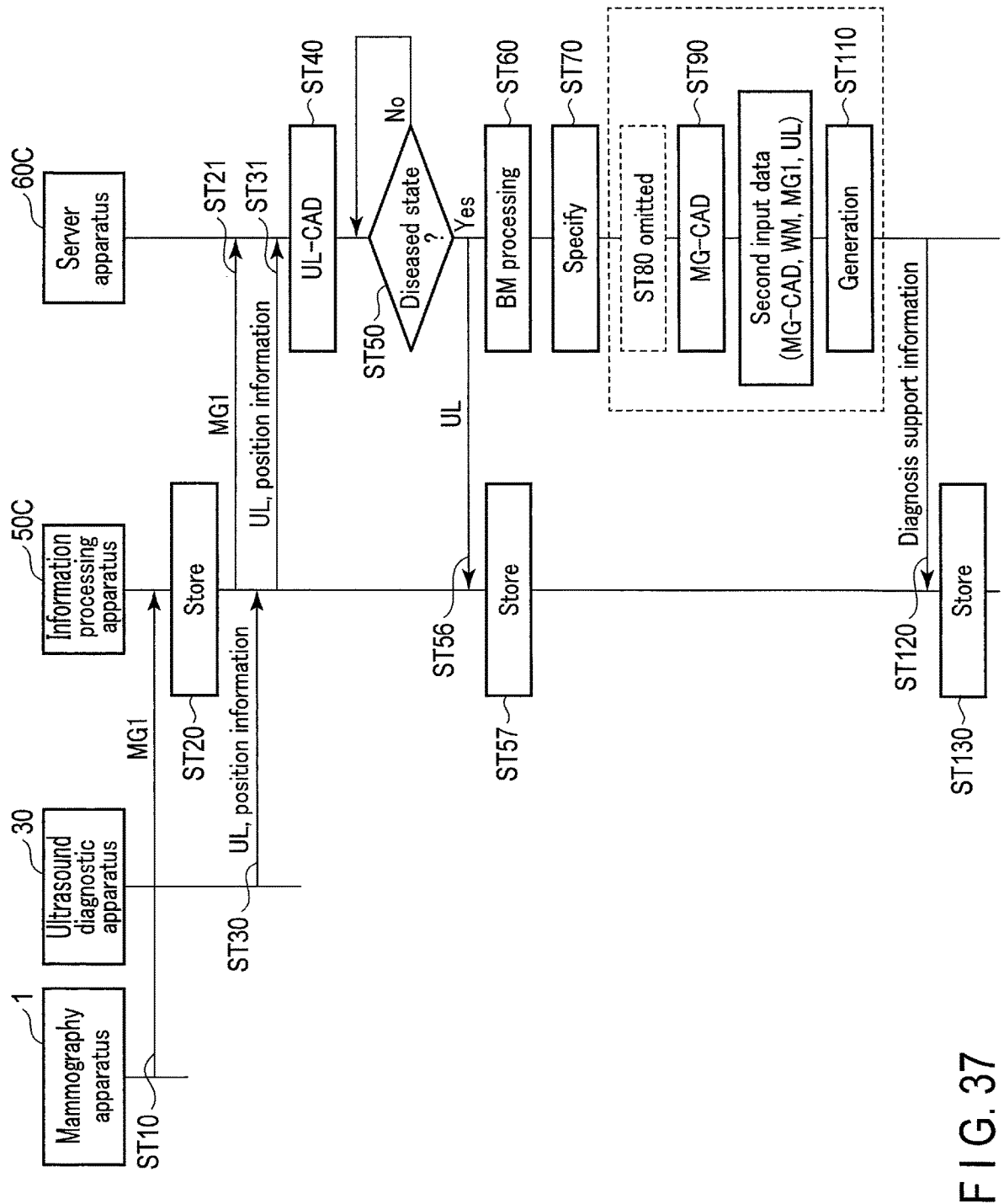
FIG. 37 is a sequence diagram for explaining operations according to a modification of the fifth embodiment.

According to the modification with the configuration as described above, the operation proceeds, for example, in such a manner as shown in FIG. 37 in which steps ST10 to ST70 are similarly performed as above while step ST80 is omitted thereafter, and the MG-CAD result is generated in step ST90 as above. As such, in step ST110 after step ST90, the processing circuitry 63 of the server apparatus 60 generates the diagnosis support information using, as an input, the second input data containing the information (WM) for the corresponding position, the first mammogram MG1, the ultrasound image UL, and the MG-CAD result.

Subsequently, steps ST120 and onward are performed in the manner as described.

According to the modification of the fifth embodiment, the diagnosis support information generated using, as an input, the second input data containing the information for the corresponding position, the first mammogram MG1, the ultrasound image UL, and the MG-CAD result is transmitted. Therefore, in addition to the effects of the fifth embodiment, the modification allows the computing process for generating the second mammogram MG2 to be omitted.

Sixth Embodiment

Next, a medical information processing system according to the sixth embodiment will be described.

The sixth embodiment is a modification of the first embodiment and the second embodiment, and it assumes a form in which a cloud 70 in a server system Svs3 is adapted to communicate with an information processing apparatus 50D in a client system Cls4 via Internet Nw_i. The Internet Nw_i is connected with the network Nw as described above, via a router, a firewall, etc. (not illustrated). The network Nw is connected with the mammography apparatus 1 and the ultrasound diagnostic apparatus 30 which are also as described above.

The information processing apparatus 50D here is intended to be a general-purpose computer and adapted to communicate with the cloud 70 via the Internet Nw_i.

The cloud 70 is constituted by a storage 71, a transmit/receive function 72, an acquisition part 73, a UL-CAD part 74, a specifying part 76, an MG2 generation part 77, an MG-CAD part 78, and a generation part 79. That is, the cloud 70 serves as a system capable of performing a series of processing from acquisition of the first mammogram MG1 and the ultrasound image UL from the mammography apparatus 1 and the ultrasound diagnostic apparatus 30 up to the transmission of the diagnosis support information. Note that the cloud 70 may arrange the storage 71, the transmit/receive function 72, the acquisition part 73, the UL-CAD part 74, the specifying part 76, the MG2 generation part 77, the MG-CAD part 78, and the generation part 79 in a single server apparatus, or distributively arrange them in multiple server apparatuses. The transmit/receive function 72, the acquisition part 73, the UL-CAD part 74, the specifying part 76, the MG2 generation part 77, the MG-CAD part 78, and the generation part 79 are each a processing part realized through execution of a control program by processing circuitry (not illustrated) within the single or multiple server apparatuses. The control program here may be, for example, a medical information processing program for causing a computer in the medical information processing system to perform the following functions (a) to (d).

(a) Function to acquire an ultrasound image of a subject and put it in a storage.

(b) Function to acquire a first mammogram of the subject and put it in the storage.

(c) Function to specify, based on imaging position information for the ultrasound image stored in the storage, a corresponding position on the first mammogram stored in the storage.

(d) Function to generate diagnosis support information for the subject using, as an input, the first input data containing a second mammogram obtained by processing the first mammogram based on the corresponding position, and the ultrasound image, or the second input data containing information for the corresponding position, the first mammogram, and the ultrasound image.

Or, a configuration of utilizing a non-transitory storage medium Md storing such a medical information processing program may be adopted so that the medical information processing program in the storage medium Md will be installed on the computer in the medical information processing system and cause the computer to realize the functions (a) to (d). Note that the function (b) is one example of a function to acquire a first modality image of the subject that differs from an ultrasound image and store this first modality image in the storage. The function (c) may be omitted. The function (d) is one example of a function to generate the diagnosis support information for the subject based on the first data containing the ultrasound image stored in the storage and the second modality image obtained by subjecting the first modality image to the process based on the imaging position for the ultrasound image, or the second data containing the information representing the imaging position for the ultrasound image, the first modality image, and the ultrasound image. According to another implementation, the control program may be, for example, a medical information processing program for causing the computer in the medical information processing system to perform the following functions (a), (b), (e), and (f).

(a) & (b) Functions as described above.

(e) Function to acquire the imaging position for the ultrasound image of the subject and put it in the storage.

(f) Function to generate the diagnosis support information for the subject based on the ultrasound image, the imaging position for this ultrasound image, and the first modality image which are stored in the storage.

The storage 71 is adapted to store various data sets such as control programs for the cloud 70, first mammograms MG1, angle information, body marks, ultrasound images UL, imaging position information for the ultrasound images UL, and so on. There are instances where no angle information or body marks are provided. In such instances, the storage 71 does not store the angle information or the body marks.

The transmit/receive function 72 is a processing part for performing transmission and reception with other apparatuses.

The acquisition part 73, the UL-CAD part 74, the specifying part 76, the MG2 generation part 77, the MG-CAD part 78, and the generation part 79 are processing parts adapted to perform processing similar to the respective functions described above, i.e., the acquisition function 55a, the UL-CAD function 55b or 63c, the specifying function 55d or 63e, the MG2 generation function 55e or 63f, the MG-CAD function 55g or 63g, and the generation function 63b. Note, however, that some modifications are made according to the configuration of including the acquisition part 73 that acquires the first mammogram MG1 and the ultrasound image UL. In one example, the generation part 79 generates the diagnosis support information for the subject using, as an input, the first input data containing the second mammogram MG2 generated by the MG2 generation part 77 and the ultrasound image UL acquired by the acquisition part 73, or the second input data containing the first mammogram MG1 and the ultrasound image UL which have been acquired by the acquisition part 73. Note that the description of the sixth embodiment will assume instances where the former one, i.e., the first input data, is adopted. The case of the latter one, i.e., the second input data, will be described with reference to a modification of the sixth embodiment. The diagnosis support information is as already discussed. Also, the generation part 79 generates the diagnosis support information using the trained model as previously described.

Figure 39:
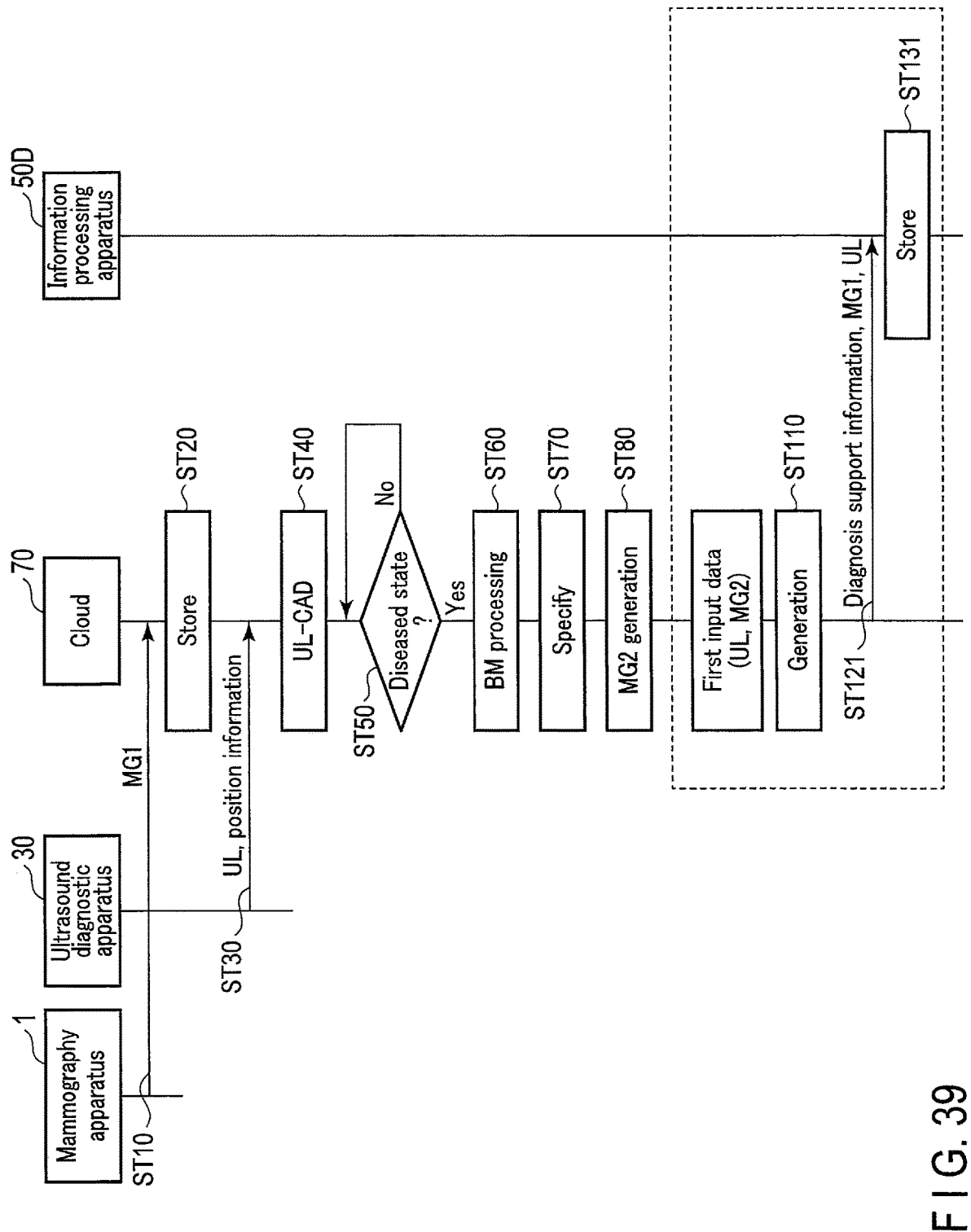
FIG. 39 is a sequence diagram for explaining operations according to the sixth embodiment.

Next, how the medical information processing system configured as above operates will be described with reference to FIG. 39.

Suppose the present state in which the storage 22 of the mammography apparatus 1 stores a first mammogram MG1 acquired by imaging the subject's breast and angle information indicative of the imaging angle for the first mammogram MG1.

Then, in step ST10, the processing circuitry 26 of the mammography apparatus 1 transmits the first mammogram MG1 to the cloud 70 in response to a request from the cloud 70.

In step ST20 after step ST10, the acquisition part 73 of the cloud 70 acquires and stores the first mammogram MG1 of the subject in the storage 71.

In step ST30 after step ST20, the ultrasound diagnostic apparatus 30 scans the subject's breast using the ultrasound probe 31 according to the operator's operation, and transmits the generated ultrasound image UL and the imaging position information for the ultrasound image UL to the cloud 70.

In step ST40 after step ST30, the acquisition part 73 acquires the ultrasound image UL of the subject and the imaging position information for the ultrasound image UL, and the UL-CAD part 74 performs UL-CAD processing with the ultrasound image UL to generate a UL-CAD result.

In step ST50 after step ST40, the UL-CAD part 74 determines whether or not the UL-CAD result indicates a diseased state, and if it does not indicate a diseased state, repeats this determining action until the end of the ultrasound inspection. On the other hand, if the UL-CAD result indicates a diseased state, the UL-CAD part 74 stores the applicable ultrasound image UL in the storage 71.

After step ST50, steps ST60 to ST70 are performed where the specifying part 76 refers to the imaging position information for the ultrasound image UL to specify a corresponding position on the first mammogram MG1. For example, a mark mk indicative of the imaging position for the ultrasound image UL is plotted on a body mark BM of the breast. The specifying part 76 also stores the body mark BM with the plotted mark mk in the storage 71, in association with the ultrasound image UL that has been stored.

In step ST70, the specifying part 76 specifies, on the first mammogram MG1, a region of interest of a band-shaped range having its center coincide with a straight line corresponding to the position of the mark mk, and generates a weight map WM for putting a greater weight on this region of interest.

In step ST80 after step ST70, the MG2 generation part 77 generates a second mammogram MG2 by subjecting the first mammogram MG1 to the process based on the position specified in step ST70. In this example, each pixel value of the weight map WM and the respective pixel value of the first mammogram MG1 are multiplied so as to generate the second mammogram MG2 emphasizing the region of interest from the first mammogram MG1.

In step ST110 after step ST80, the generation part 79 generates diagnosis support information for the subject using, as an input, the first input data containing the generated second mammogram MG2 and the ultrasound image UL that is stored in the storage 71. In this example, the generation part 79 acquires the diagnosis support information from the first input data using the trained model stored in the storage 71.

In step ST121 after step ST110, the transmit/receive function 72 transmits the generated diagnosis support information, the first mammogram MG1, and the ultrasound image UL to the information processing apparatus 50D.

In step ST131 after step ST121, the processing circuitry (not illustrated) of the information processing apparatus 50D receives the diagnosis support information, the first mammogram MG1, and the ultrasound image UL, and stores the diagnosis support information, etc. in its storage (not illustrated). The information processing apparatus 50D displays the diagnosis support information, the first mammogram MG1, and the ultrasound image which are stored in the storage, according to an operation by the operator (interpreting doctor). In this manner, support for the interpreting doctor's diagnosing work is provided.

According to the sixth embodiment as described above, an ultrasound image of a subject is acquired, a first mammogram of the subject is acquired, and based on the imaging position information for the ultrasound image, a corresponding position on the first mammogram is specified. The diagnosis support information for the subject is generated using, as an input, the first input data containing a second mammogram obtained by processing the first mammogram based on the corresponding position, and the ultrasound image.

Such processing in the medical information processing system, from acquisition of the images to generation of the diagnosis support information, is performed without using the information processing apparatus operated by the operator. Therefore, the sixth embodiment can mitigate the burden on the operator, in addition to providing the effects as in the first embodiment.

Figure 40:
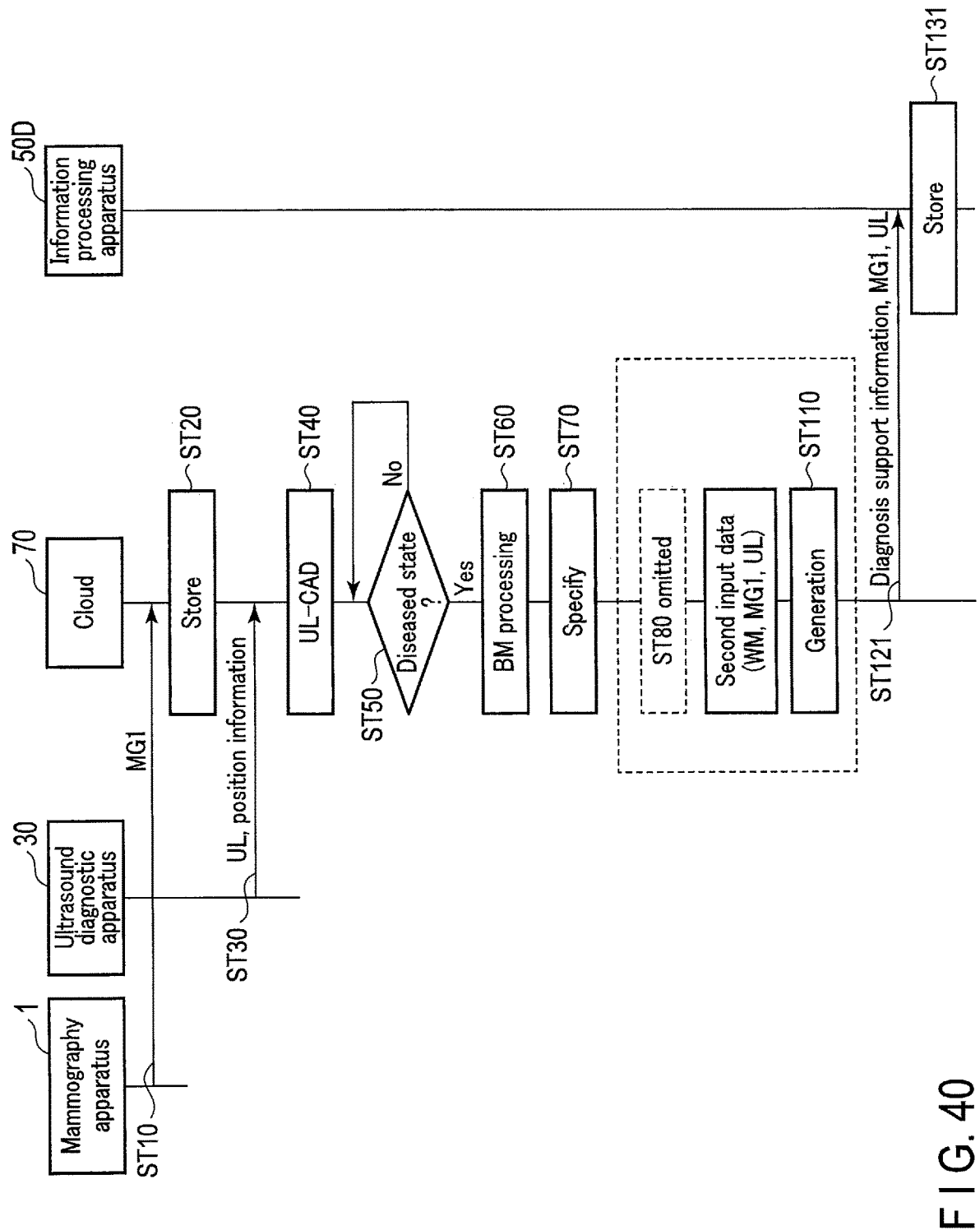
FIG. 40 is a sequence diagram for explaining operations according to a modification of the sixth embodiment.

Furthermore, as shown in FIG. 40, the configuration according to the sixth embodiment, where the processing in the medical information processing system from acquisition of the images to generation of the diagnosis support information is performed in the manner as discussed, can be applied to the modification of the first embodiment that relates to the use of the second input data. The case of such an application can realize the effect of mitigating the operator's burden, in addition to the effects as in the modification of the first embodiment.

Figure 41:
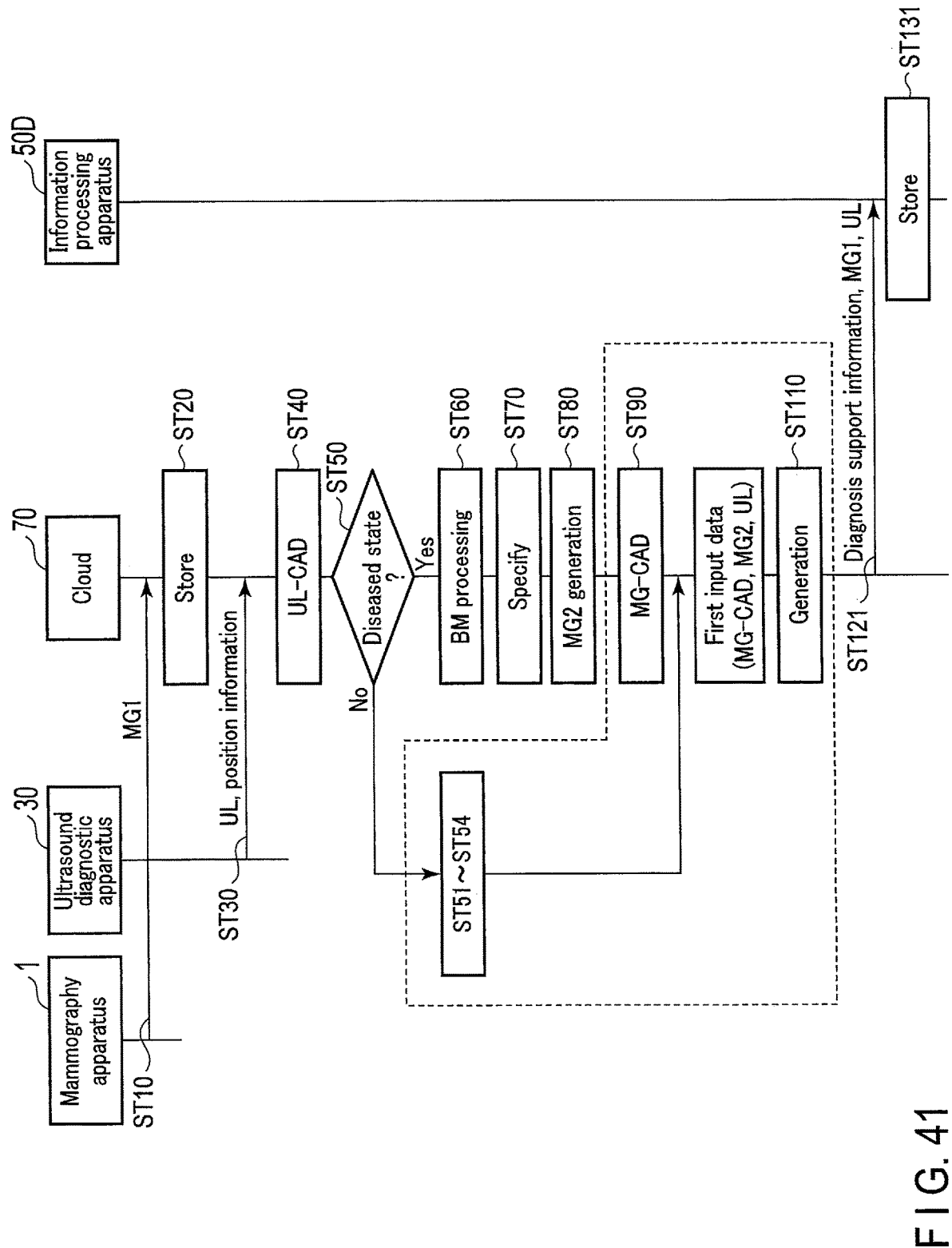
FIG. 41 is a sequence diagram for explaining operations according to another modification of the sixth embodiment.

Also, as shown in FIG. 41, the configuration according to the sixth embodiment, where the processing in the medical information processing system from acquisition of the images to generation of the diagnosis support information is performed in the manner as discussed, can be applied to the second embodiment that relates to the use of the first input data containing the MG-CAD result. The case of this application can realize the effect of mitigating the operator's burden, in addition to the effects as in the second embodiment.

Figure 42:
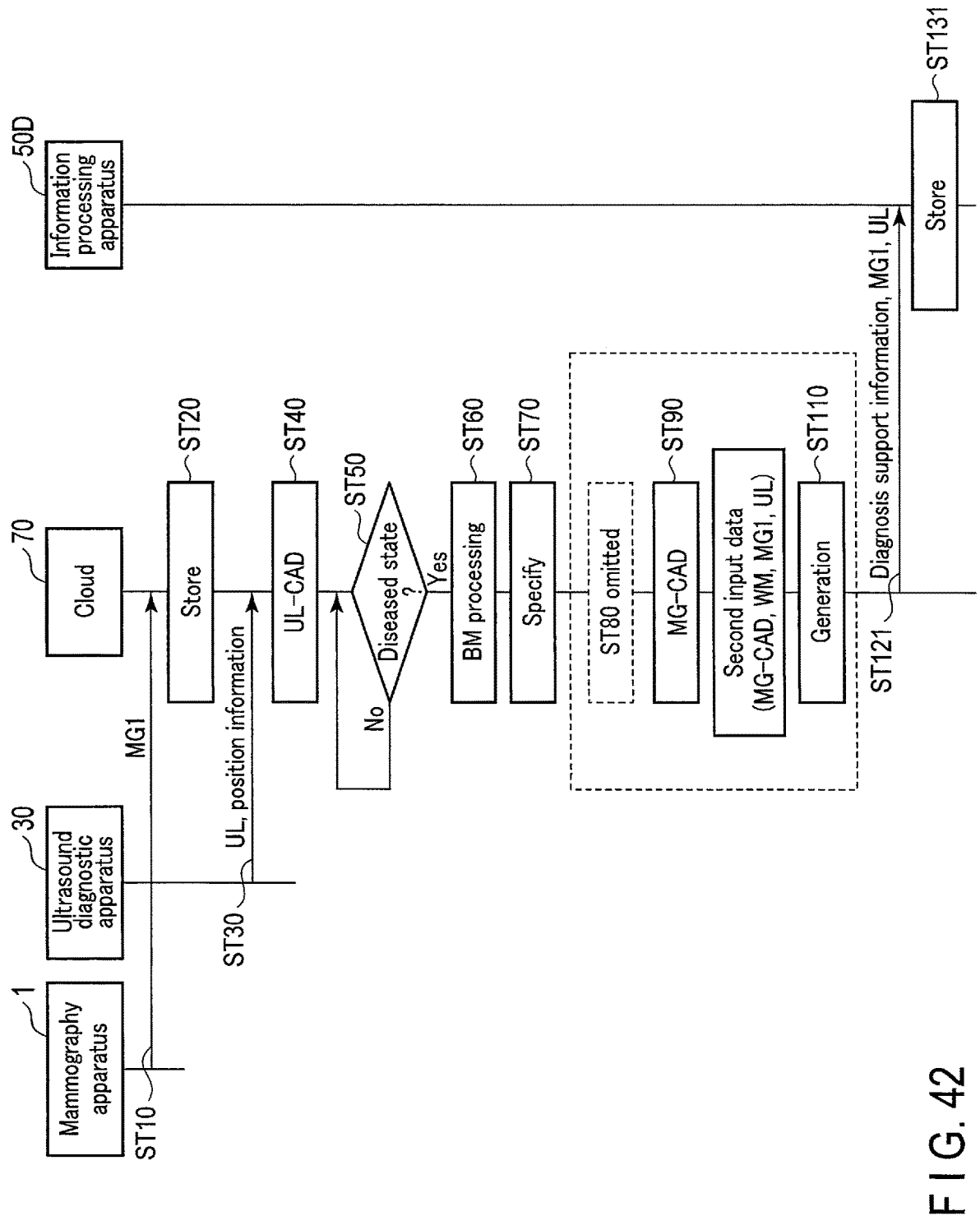
FIG. 42 is a sequence diagram for explaining operations according to yet another modification of the sixth embodiment.

As shown in FIG. 42, the configuration according to the sixth embodiment, where the processing in the medical information processing system from acquisition of the images to generation of the diagnosis support information is performed in the manner as discussed, can be applied to the modification of the second embodiment that relates to the use of the second input data containing the MG-CAD result. The case of this application can realize the effect of mitigating the operator's burden, in addition to the effects as in the modification of the second embodiment.

In an implementation, moreover, the medical information processing system according to the sixth embodiment may be provided as a single apparatus having each function of the cloud 70 and the information processing apparatus 50D, and communicably connected with the mammography apparatus 1 and the ultrasound diagnostic apparatus 30. Here, the medical information processing system as a single apparatus is applicable to each of the first embodiment, the modification of the first embodiment, the second embodiment, and the modification of the second embodiment independently.

First, the case of applying the medical information processing system as a single apparatus to the first embodiment will be supposed. Similar to what is shown in, for example, FIGS. 6 and 39, the medical information processing system in this case acquires an ultrasound image of a subject, acquires a first mammogram of the subject, and specifies, based on the imaging position information for the ultrasound image, a corresponding position on the first mammogram. Also, the medical information processing system generates the diagnosis support information for the subject using, as an input, the first input data containing a second mammogram obtained by processing the first mammogram based on the corresponding position, and the ultrasound image. The medical information processing system, in displaying the diagnosis support information, the first mammogram MG1, and the ultrasound image according to an operation by the operator (interpreting doctor), provides support for the interpreting doctor's diagnosing work.

The case of applying the medical information processing system as a single apparatus to the modification of the first embodiment will be supposed. Similar to what is shown in, for example, FIGS. 13 and 40, the medical information processing system in this case uses, in place of the first input data, the second input data containing information for the corresponding position, a first mammogram, and an ultrasound image.

Also, the case of applying the medical information processing system as a single apparatus to the second embodiment will be supposed. Similar to what is shown in, for example, FIGS. 17 and 41, the medical information processing system in this case differs from the first embodiment in that the first input data for generating the diagnosis support information further includes the result of computer-aided detection with the first mammogram MG1.

The case of applying the medical information processing system as a single apparatus to the modification of the second embodiment will be supposed. Similar to what is shown in, for example, FIGS. 22 and 42, the medical information processing system in this case differs from the modification of the first embodiment in that the second input data for generating the diagnosis support information further includes the result of computer-aided detection with the first mammogram MG1.

As such, the medical information processing system as a single apparatus is applicable to each of the first embodiment, the modification of the first embodiment, the second embodiment, and the modification of the second embodiment independently, and can provide the same effects as these embodiments and their modifications when applied.

In each of the foregoing embodiments and modifications, the mammography apparatus 1 may be replaced with a modality apparatus such as a magnetic resonance imaging (MRI) apparatus, a positron emission mammography (PEM) apparatus, a positron emission tomography (PET) apparatus, a computed tomography (CT) apparatus, etc. The modality apparatus may be a PET apparatus for the whole body, or a PET-CT apparatus. Accordingly, the foregoing embodiments and modifications may each use, in place of the mammograms such as the first mammogram MG1 and the second mammogram MG2, any of modality images including MRI images, PEM images, PET images, and CT images.

Figure 43:
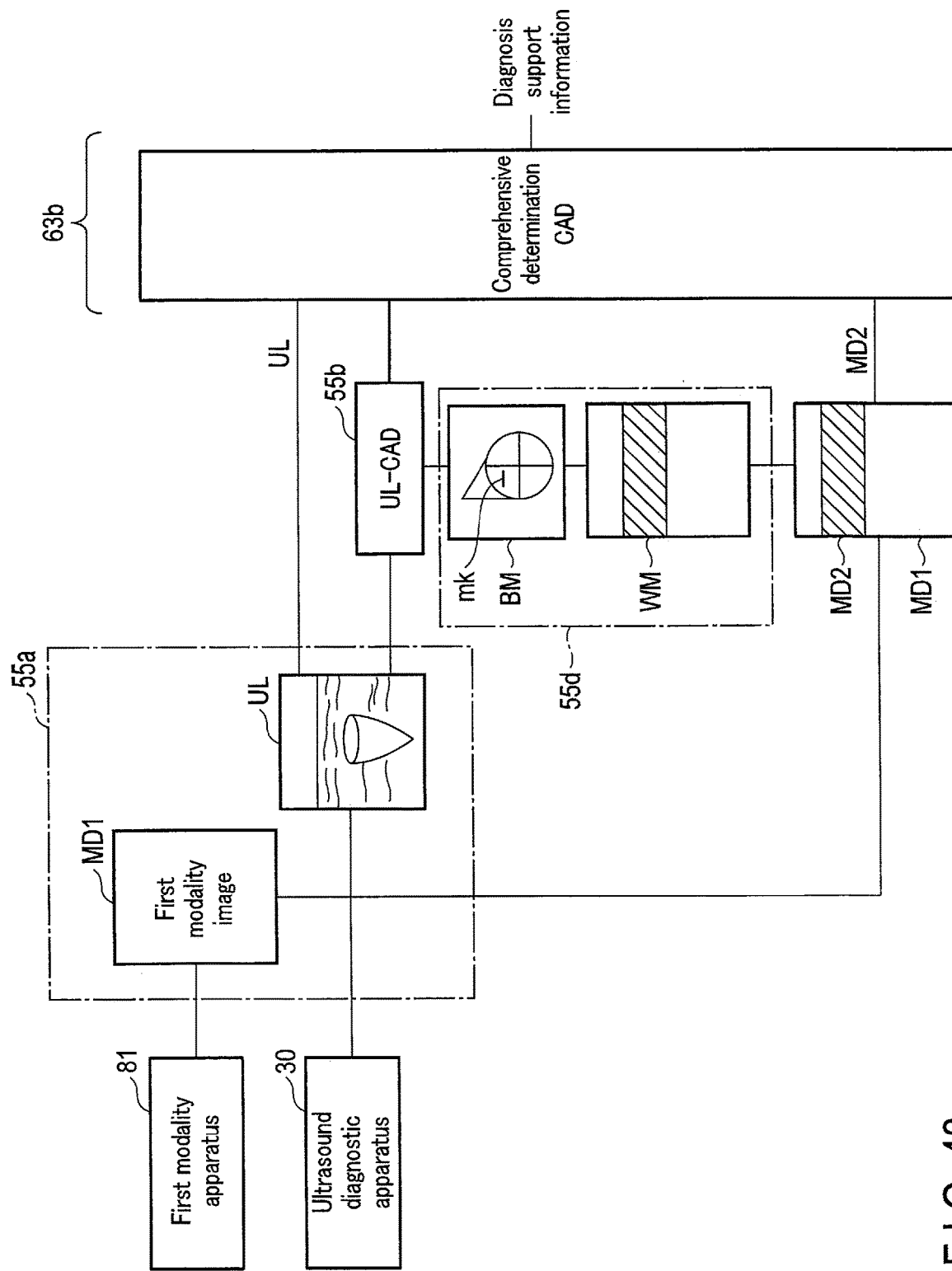
FIG. 43 is a schematic diagram showing, as one modification applicable to each of the foregoing embodiments and modifications, a process from acquisition of a first modality image and an ultrasound image up to generation of diagnosis support information.

With such use of, for example, an MRI apparatus and MRI images in place of the mammography apparatus 1 and the mammograms, the diagnosis can be endowed with an enhanced accuracy. To be more specific, MRI images are for use in instances such as thorough examinations to determine a benign or a malignant state of a site that is suspected of being malignant upon a health checkup, examinations to determine an excision range prior to surgery, and so on. MRI images are generally used to support mammography inspection and ultrasound inspection in health checkups. In this relation, for capturing an image of breast cancer, MRI imaging with a contrast medium is performed so that an MRI image showing a contrast for the breast cancer is obtained. However, MRI images also let mammary glands appear with high brightness, and as such, the interpretation based only on MRI images might not enable diagnosis of a lesion. To cope with this, an ultrasound image and an MRI image can be comprehensively interpreted so that diagnosis with high accuracy is achieved. For example, as shown in FIG. 43, which is a modification of FIG. 6, the locating information for a region of interest in an ultrasound image UL is acquired based on a body mark BM obtained from the ultrasound inspection and in the coordinate system having the center at the nipple. Also, the nipple is detected in a first modality image MD1 (e.g., a 3D MRI image (volume data)) obtained by a first modality apparatus 81 as an MRI apparatus. A second modality image MD2 (slice image) corresponding to the locating information for the ultrasound image UL is acquired from the first modality image MD1. Then, the ultrasound image UL and the second modality image MD2 (e.g., the MRI slice image) are used as inputs of the generation function 63b so that the diagnosis support information can be obtained. According to the example discussed with FIG. 43, assistance for the interpretation in thorough examinations can also be provided. Note that, as in this modified example of FIG. 6, the use of a modality image such as an MRI image as the first modality image in place of the mammogram is applicable also to each of the foregoing embodiments and modifications. Similarly, each of the embodiments and modifications can employ any modality apparatus as the first modality apparatus 81, such as an MRI apparatus, in place of the mammography apparatus 1.

Figure 44:
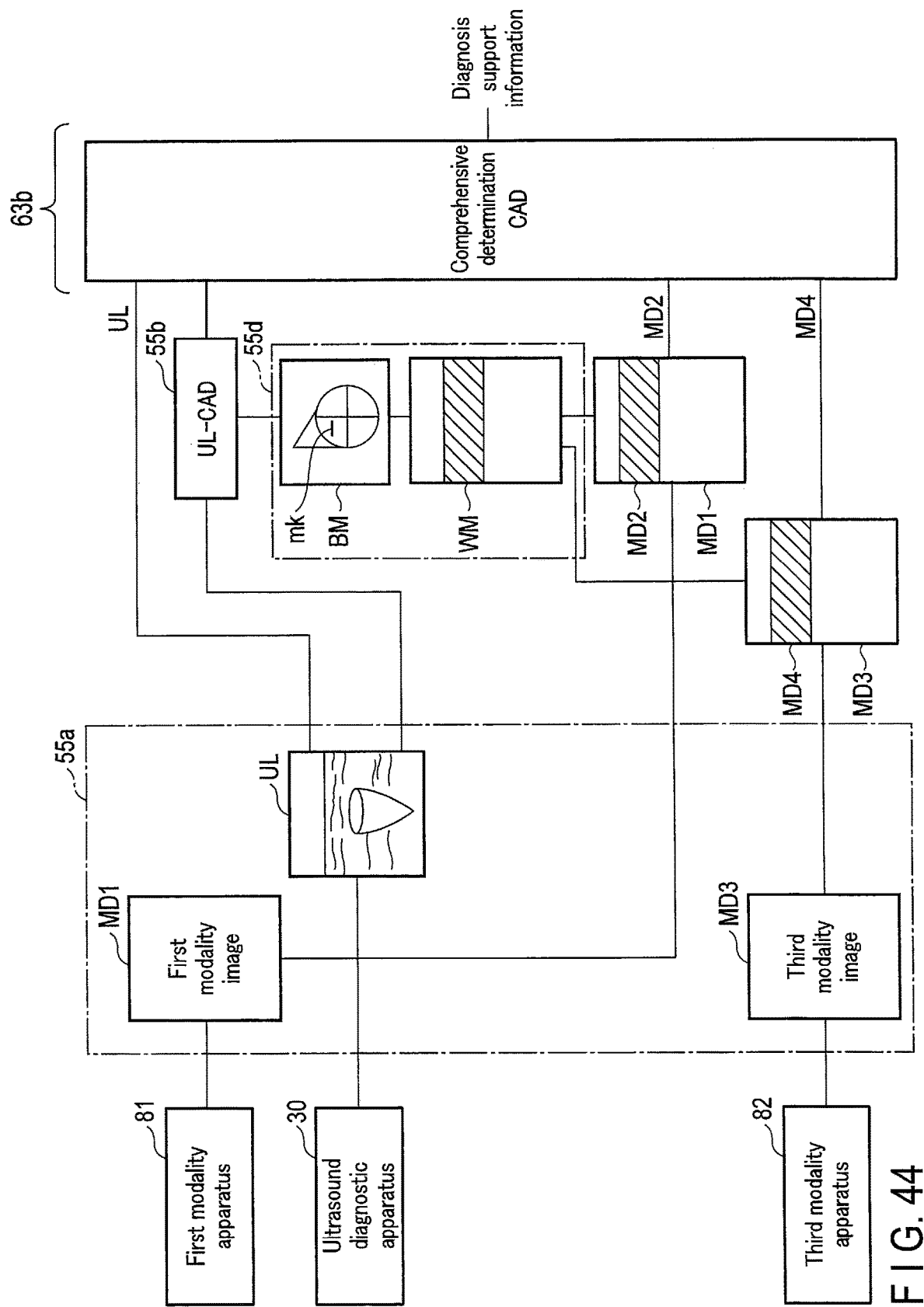
FIG. 44 is a schematic diagram showing, as one modification applicable to each of the foregoing embodiments and modifications, a process from acquisition of a first modality image, a third modality image, and an ultrasound image up to generation of diagnosis support information.

The number of modality images used in addition to the ultrasound image is not limited to one, and may be two or more, for example. As one exemplary implementation, the locating information for a region of interest in an ultrasound image UL is acquired based on a body mark BM obtained from the ultrasound inspection and in the coordinate system having the center at the nipple, as shown in FIG. 44, which is a modification of FIG. 6. Also, the nipple is detected in a first modality image MD1 (e.g., a 3D MRI image (volume data)) obtained by the first modality apparatus 81 as an MRI apparatus. A second modality image MD2 (slice image) corresponding to the locating information for the ultrasound image UL is acquired from the first modality image MD1. Likewise, the nipple is detected in a third modality image MD3 (e.g., a PEM image) obtained by a third modality apparatus 82 as a PEM apparatus. A fourth modality image MD4 (slice image) corresponding to the locating information for the ultrasound image UL is acquired from the third modality image MD3. Since PEM offers an equivalent sensitivity to MRI and a higher specificity than MRI, the use of PEM in thorough examinations can reduce false positives. The sensitivity here is an index indicating the proportion at which a diseased state is not overlooked. The specificity is an index indicating the proportion at which a non-diseased site is not determined to be in a diseased state. The PEM apparatus used here may be a type adapted to hold the breast between two detectors, or a type adapted to surround the breast by three or more detectors while permitting the breast to hang down in the subject's prone posture. In any case, the ultrasound image UL, the second modality image MD2 (e.g., the MRI slice image), and the fourth modality image MD4 (e.g., the PEM slice image) are used as inputs of the generation function 63b so that the diagnosis support information can be obtained. According to the example discussed with FIG. 44, the interpretation in thorough examinations can be assisted. Note that, as in the modified example of FIG. 6, the use of multiple modality images in addition to the ultrasound image is applicable also to each of the foregoing embodiments and modifications. Moreover, the image constituting such multiple modality images is not limited to an MRI image or a PEM image as explained with reference to FIG. 44. For example, a PET image or a CT image acquired from a PET-CT apparatus may be used for the multiple modality images.

It is not always required to use images such as an ultrasound image, a modality image, etc. in the comprehensive determination CAD. For example, a configuration as shown in FIG. 45, which is a modification of FIG. 17 or FIG. 22, may be adopted where the generation function 63b generates the diagnosis support information without using the ultrasound image UL or the first modality image MD1. According to FIG. 45, the generation function 63b generates the diagnosis support information based on the result, i.e., a first result, of computer-aided detection with the ultrasound image UL performed by the UL-CAD function 55b (first result acquirer), the result, i.e., a second result, of computer-aided detection with the first modality image MD1 performed by the MD-CAD function 55g (second result acquirer), and the weight map WM (locating information). In this case, the generation function 63b is one example of the generation processor for generating the diagnosis support information for the subject based on inputs including the result of computer-aided detection performed with the ultrasound image UL, the result of computer-aided detection performed with the first modality image MD1, and the imaging position for the ultrasound image UL. The UL-CAD function 55b here is one example of a first result acquirer for acquiring a first result of computer-aided detection with the ultrasound image of the subject. The UL-CAD function 55b may perform the computer-aided detection with the ultrasound image to acquire the first result. The "first result" may simply be called "result". The MD-CAD function 55g here is one example of a second result acquirer for acquiring a second result of computer-aided detection with the first modality image of the subject that differs from an ultrasound image. The MD-CAD function 55g may perform the computer-aided detection with the first modality image to acquire the second result. The "second result" may simply be called "result". In this manner as well, comprehensive interpretation of a modality image and an ultrasound image is enabled and the diagnosis can be assisted.

Figure 46:
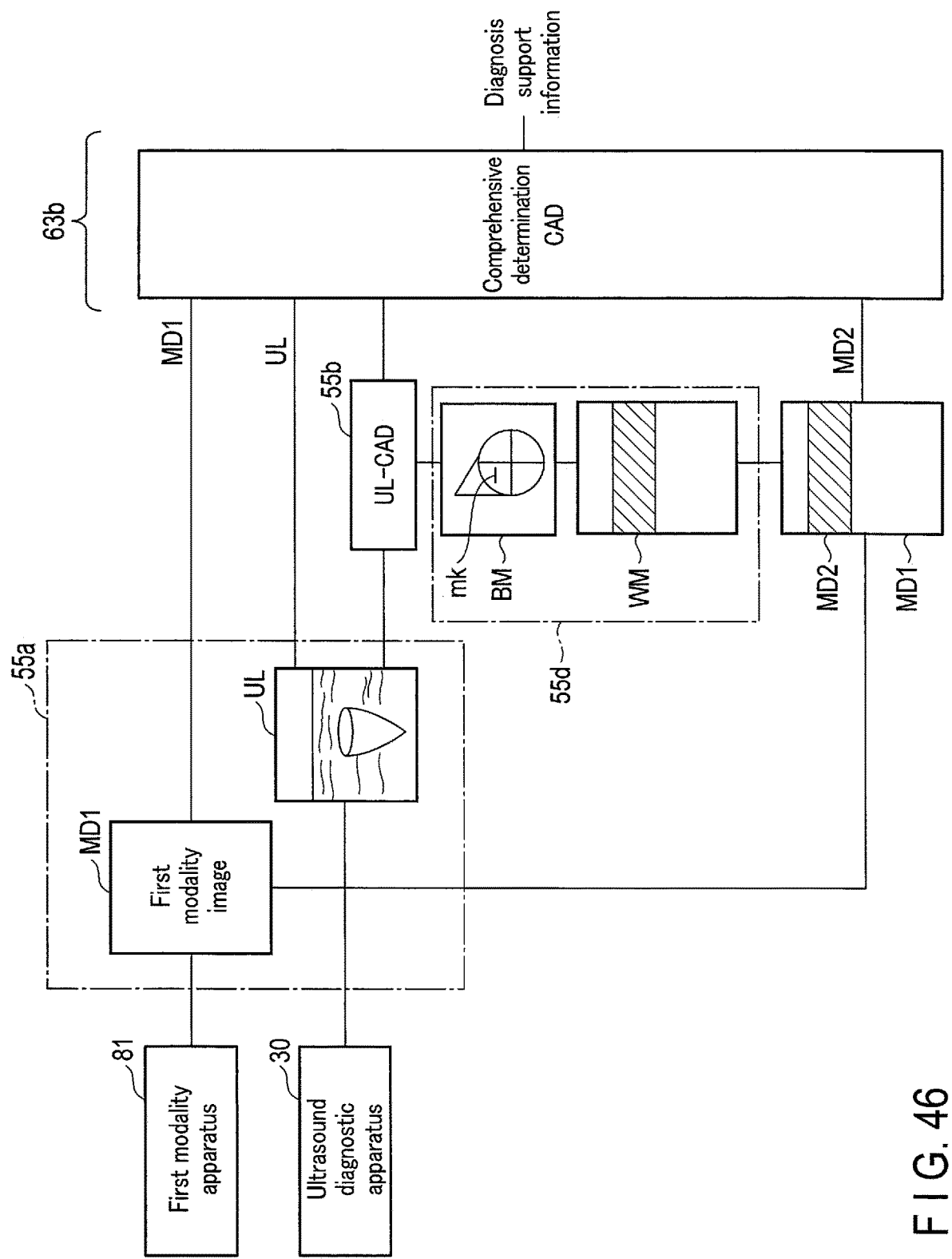
FIG. 46 is a schematic diagram showing, as one modification applicable to each of the foregoing embodiments and modifications, a process from acquisition of a first modality image and an ultrasound image up to generation of diagnosis support information.

When each of the foregoing embodiments and modifications is furnished with the UL-CAD function 55b (first detection processor) for performing computer-aided detection with the ultrasound image UL as shown in, for example, FIG. 46, the generation function 63b (generation processor) may operate in the following manner.

That is, the generation function 63b may generate the diagnosis support information for the subject based on the result of computer-aided detection with the ultrasound image UL performed by the UL-CAD function 55b, the information (e.g., weight map WM) representing the imaging position for the ultrasound image UL, the first modality image MD1, and the ultrasound image UL.

Figure 47:
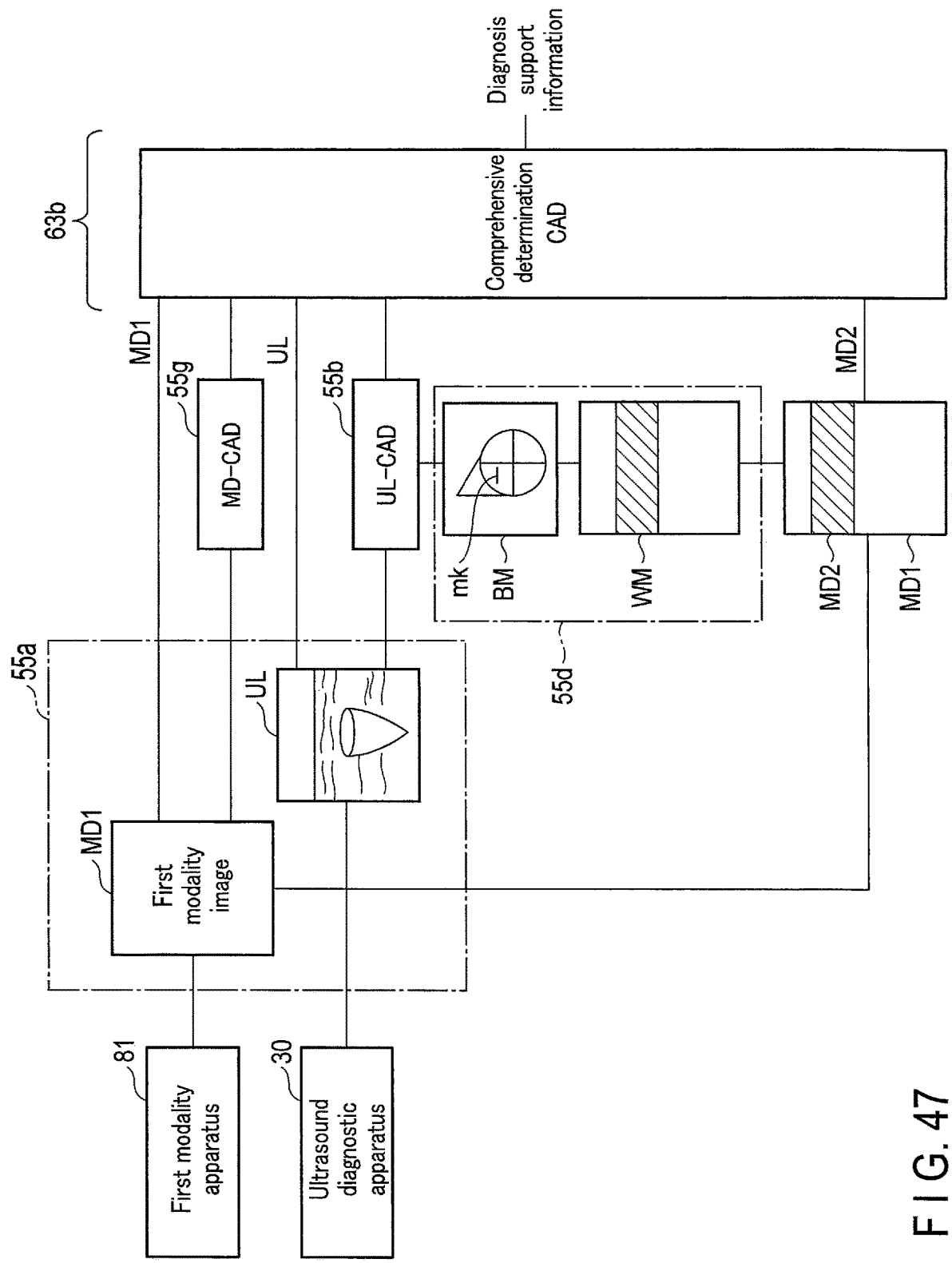
FIG. 47 is a schematic diagram showing, as one modification applicable to each of the foregoing embodiments and modifications, a process from acquisition of a first modality image and an ultrasound image up to generation of diagnosis support information.

Also, when the UL-CAD function 55b (first detection processor) for performing computer-aided detection with the ultrasound image UL and the MD-CAD function 55g (second detection processor) for performing computer-aided detection with the first modality image MD1 are provided as shown in, for example, FIG. 47, the generation function 63b (generation processor) may operate in the following manner.

That is, the generation function 63b may generate the diagnosis support information for the subject based on inputs including the result of computer-aided detection performed with the ultrasound image UL, the result of computer-aided detection performed with the first modality image MD1, and the imaging position for the ultrasound image UL. The generation function 63b may also generate the diagnosis support information for the subject based on inputs including the result of computer-aided detection performed with the ultrasound image UL, the result of computer-aided detection performed with the first modality image MD1, the imaging position for the ultrasound image UL, the ultrasound image UL, and the first modality image MD1. In these cases, the UL-CAD function 55b, the MD-CAD function 55g, and the generation function 63b constitute one example of the generator that includes the first detection processor, the second detection processor, and the generation processor.

Further, when an MD2 generation function 55j (image generator) for generating the second modality image MD2 by processing the first modality image based on the imaging position of the ultrasound image UL, the UL-CAD function 55b (first detection processor) for performing computer-aided detection with the ultrasound image UL, and an MD-CAD function 55h (second detection processor) for performing computer-aided detection with the second modality image MD2 are provided as shown in, for example, FIG. 48, the generation function 63b (generation processor) may operate in the following manner.

Figure 49:
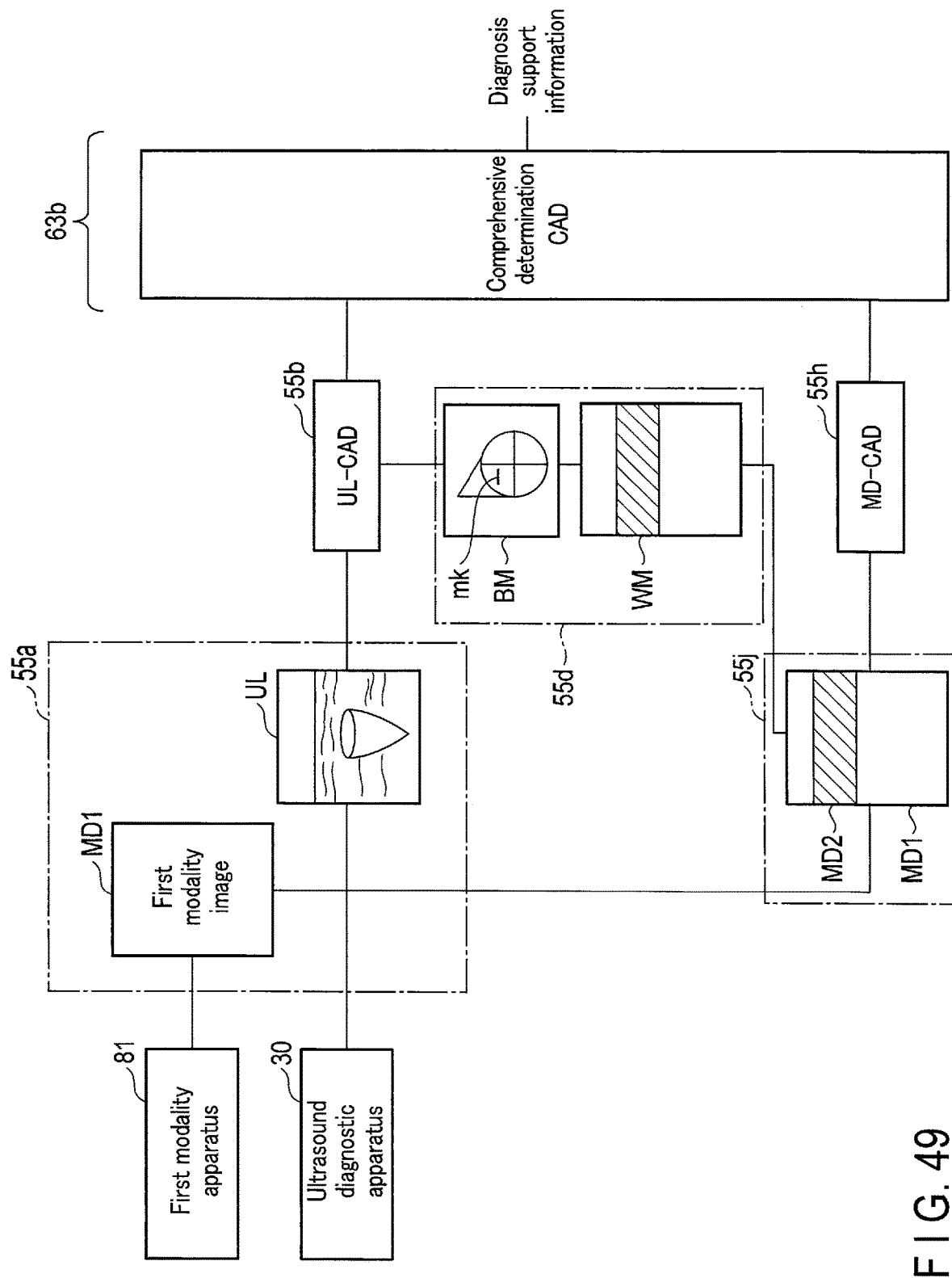
FIG. 49 is a schematic diagram showing, as one modification applicable to each of the foregoing embodiments and modifications, a process from acquisition of a first modality image and an ultrasound image up to generation of diagnosis support information.

That is, the generation function 63b may generate the diagnosis support information for the subject based on, as shown in FIG. 49, inputs including the result of computer-aided detection performed with the ultrasound image UL and the result of computer-aided detection performed with the second modality image MD2. The generation function 63b may also generate the diagnosis support information for the subject based on, as shown in FIG. 50, inputs including the result of computer-aided detection performed with the ultrasound image UL, the result of computer-aided detection performed with the second modality image MD2, the ultrasound image UL, and the second modality image MD2. In these cases, the MD2 generation function 55j, UL-CAD function 55b, the MD-CAD function 55h, and the generation function 63b constitute one example of the generator that includes the image generator, the first detection processor, the second detection processor, and the generation processor.

According to at least one embodiment described above, an ultrasound image of a subject is acquired, a first modality image of the subject is acquired, an imaging position for the ultrasound image is acquired, and based on the ultrasound image, the imaging position for the ultrasound image, and the first modality image, diagnosis support information for the subject is generated.

Therefore, the modality image and the ultrasound image are comprehensively interpreted so that the diagnosis can be assisted.

The term "processor" used herein refers to, for example, a central processing unit (CPU) or a graphics processing unit (GPU), or various types of circuitry which may be an application-specific integrated circuit (ASIC), a programmable logic device (such as a simple programmable logic device (SPLD), a complex programmable logic device (CPLD), or a field programmable gate array (FPGA)), and so on. The processor reads programs stored in the storage and executes them to realize the intended functions. The programs may be incorporated directly in circuits of the processor, instead of being stored in the storage. According to such implementation, the processor reads the programs incorporated in its circuits and executes them to realize the functions. The embodiments herein do not limit the processor to a single circuitry-type processor. Multiple independent circuits may be combined and integrated as one processor to realize the intended functions. Furthermore, multiple components or features as given in FIGS. 2, 4, and 18 may be integrated as one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical information processing system, comprising:
    processing circuitry configured to
        acquire an ultrasound image of a subject,
        acquire a first modality image of the subject, the first modality image differing from the ultrasound image, and
        acquire an imaging position for the ultrasound image; and
    a memory storing a trained model,
    wherein the processing circuitry is further configured to
        perform computer-aided detection with the ultrasound image,
        perform computer-aided detection with the first modality image,
        generate diagnosis support information for the subject by inputting, in an inference stage, inference inputs including a result of the computer-aided detection with the ultrasound image, a result of the computer-aided detection with the first modality image, and the imaging position for the ultrasound image to the trained model, and
        when determining that the result of the computer-aided detection with the ultrasound image indicates a diseased state, plot a mark indicative of the imaging position for the ultrasound image on a schematic diagram of a breast of the subject, and specify, on the first modality image, a band-shaped region of interest having a center coincide with a straight line corresponding to a position of the plotted mark and corresponding to an imaging angle of the first modality image, the first modality image being a mammogram, and
        wherein the trained model was previously trained, in a training stage, based on training inputs, different from the inference inputs, including a result of a computer-aided detection with a training ultrasound image, a result of a computer-aided detection with a first training modality image, and a training imaging position for the training ultrasound image, the training ultrasound image, the first training modality image, and the training imaging position being acquired before the training stage.

2. The medical information processing system according to claim 1, wherein the processing circuitry is further configured to generate the diagnosis support information for the subject by inputting the inference inputs to the trained model, the inference inputs further including the ultrasound image and the first modality image, and
    wherein the trained model was previously trained, in the training stage, based on the training inputs, which further include the training ultrasound image and the first training modality image.

3. A medical information processing system, comprising:
    processing circuitry configured to
    acquire an ultrasound image of a subject,
    acquire a first modality image of the subject, the first modality image differing from the ultrasound image, and
    acquire an imaging position for the ultrasound image; and
    a memory storing a trained model,
    wherein the processing circuitry is further configured to
    generate a second modality image by processing the first modality image based on the imaging position for the ultrasound image,
    perform computer-aided detection with the ultrasound image,
    perform computer-aided detection with the second modality image,
    generate diagnosis support information for the subject by inputting, in an inference stage, inference inputs including a result of the computer-aided detection with the ultrasound image and a result of the computer-aided detection with the second modality image to the trained model, and
    when determining that the result of the computer-aided detection with the ultrasound image indicates a diseased state, plot a mark indicative of the imaging position for the ultrasound image on a schematic diagram of a breast of the subject, and specify, on the first modality image, a band-shaped region of interest having a center coincide with a straight line corresponding to a position of the plotted mark and corresponding to an imaging angle of the first modality image, the first modality image being a mammogram, and
    wherein the trained model was previously trained, in a training stage, based on training inputs, different from the inference inputs, including a result of a computer-aided detection with a training ultrasound image and a result of a computer-aided detection with a second training modality image, the training ultrasound image and the second training modality image being acquired before the training stage.

4. The medical information processing system according to claim 3, wherein the processing circuitry is further configured to generate the diagnosis support information for the subject by inputting the inference inputs to the trained model, the inference inputs further including the ultrasound image and the second modality image, and wherein the trained model was previously trained, in the training stage, based on the training inputs, which further include the training ultrasound image and the second training modality image.

\* \* \* \* \*